US012653424B2

(12) United States Patent
Huang et al.

(10) Patent No.: US 12,653,424 B2
(45) Date of Patent: Jun. 16, 2026

(54) PHYSIOLOGICAL SIGNAL MONITORING SYSTEM FOR FAST ASSEMBLY

(71) Applicant: BIONIME CORPORATION, Taichung City (TW)

(72) Inventors: Chun-Mu Huang, Taichung City (TW); Chieh-Hsing Chen, Taichung City (TW)

(73) Assignee: Bionime Corporation, Taichung City (TW)

( * ) Notice: Subject to any disclaimer, the term of this patent is extended or adjusted under 35 U.S.C. 154(b) by 0 days.

(21) Appl. No.: 16/945,203

(22) Filed: Jul. 31, 2020

(65) Prior Publication Data

US 2021/0030319 A1 Feb. 4, 2021

Related U.S. Application Data

(60) Provisional application No. 62/882,140, filed on Aug. 2, 2019.

(30) Foreign Application Priority Data

Jan. 10, 2020 (TW) ................................. 109100992

(51) Int. Cl.
*A61B 5/1455* (2006.01)
*A61B 5/00* (2006.01)
(Continued)

(52) U.S. Cl.
CPC ........ *A61B 5/14503* (2013.01); *A61B 5/0002* (2013.01); *A61B 5/150305* (2013.01);
(Continued)

(58) Field of Classification Search
CPC ............ A61B 5/14532; A61B 5/14546; A61B 5/14865; A61B 5/6833; A61B 2560/063;
(Continued)

(56) References Cited

U.S. PATENT DOCUMENTS 3,556,334 A * 1/1971 Howard ............... B65D 41/185
215/302
3,883,036 A * 5/1975 Mahaffy ............ B65D 21/0219
220/781
(Continued)

FOREIGN PATENT DOCUMENTS

CN 101107025 A 1/2008
CN 105581781 A 5/2016
(Continued)

OTHER PUBLICATIONS

European Search Report dated Oct. 8, 2020 cited in application EP 20188962.
(Continued)

*Primary Examiner* — Marjan Fardanesh
(74) *Attorney, Agent, or Firm* — Perkins Coie LLP; Viola Kung; Gautam Thatte

(57) ABSTRACT

An implantation device for prompt subcutaneous implantation of a sensor to measure a physiological signal of an analyte in a biofluid of a living body is disclosed. The implantation device includes a housing, an implantation module, a detachable module and a bottom cover. The housing has a bottom opening. The implantation module includes an implanting device and a needle extracting device. The detachable module includes the sensor detachably engaged with the implantation module; and a base configured to mount the sensor thereon. The bottom cover is detachably coupled to the bottom opening so that the housing and the bottom cover together form an accommodating space. The implantation module and the detachable module are accommodated in the accommodating space. The bottom cover has an operating portion configured to bear a force, and a supporting portion is formed on the opposite end of the operating portion.

20 Claims, 55 Drawing Sheets

(51) Int. Cl.

| | |
|---|---|
| *A61B 5/145* | (2006.01) |
| *A61B 5/15* | (2006.01) |
| *A61B 17/34* | (2006.01) |
| *B65D 81/26* | (2006.01) |
| *A61B 5/1486* | (2006.01) |
| *A61B 50/30* | (2016.01) |

(52) U.S. Cl.
CPC ...... *A61B 5/150503* (2013.01); *A61B 5/6833* (2013.01); *A61B 5/6848* (2013.01); *A61B 5/6849* (2013.01); *A61B 17/3468* (2013.01); *B65D 81/266* (2013.01); *A61B 5/1451* (2013.01); *A61B 5/14532* (2013.01); *A61B 5/14865* (2013.01); *A61B 50/30* (2016.02); *A61B 2050/3004* (2016.02); *A61B 2560/0443* (2013.01); *A61B 2560/045* (2013.01); *A61B 2560/063* (2013.01); *A61B 2562/16* (2013.01); *A61B 2562/242* (2013.01)

(58) Field of Classification Search
CPC .......... A61B 5/1451; A61B 2560/0412; A61B 5/6848–6849; A61B 5/150259; A61B 5/150351; A61B 5/15107–15111; A61B 5/15117; A61B 5/1513; A61B 5/15144; A61B 5/14503; A61B 5/1473–14735; A61B 17/3468; A61B 2562/16; A61B 2050/005; A61B 2050/006; A61B 2050/0065–0066; A61B 2050/0082–0083; A61M 5/14248–14252; A61M 5/158; A61M 2005/1583–1585; A61M 5/1723; A61M 2230/201; A61M 2005/14252–14256; A61M 2005/14268; A61M 2005/14284; B65D 43/162; B65D 53/02; B65D 2543/00092; B65D 2543/00296; B65D 2543/00527–00537; B65D 2543/00629; B65D 2543/00685; B65D 2543/0074; B65D 2543/00796; B65D 2543/00972; B65D 41/16–165; B65D 41/22–225; B65D 43/021; B65D 43/06; B65D 43/08; B65D 43/12; B65D 2543/00435; B65D 2543/00564; B65D 2543/00592; B65D 2543/0062; B65D 2543/00648; B65D 2543/00731; B65D 2543/00759; B65D 2543/00842; B65D 2543/00888; B65D 2543/00907–00916; B65D 2543/00944; G01N 33/48778
USPC ...................... 220/378, 780, 789, 790, 791
See application file for complete search history.

(56) References Cited

U.S. PATENT DOCUMENTS

| | | | |
|---|---|---|---|
| 6,093,172 | A | 7/2000 | Funderburk et al. |
| 6,484,046 | B1 | 11/2002 | Say et al. |
| 7,381,184 | B2 | 6/2008 | Funderburk et al. |
| 8,280,475 | B2 | 10/2012 | Brister et al. |
| 8,439,838 | B2 | 5/2013 | Mogensen et al. |
| 8,696,570 | B2 | 4/2014 | Yodfat et al. |
| 8,870,822 | B2 | 10/2014 | Thalmann et al. |
| 9,186,098 | B2 | 11/2015 | Lee et al. |
| 10,278,732 | B2 | 5/2019 | Schoonmaker et al. |
| 10,413,183 | B2 | 9/2019 | Antonio et al. |
| 2009/0216103 | A1 | 8/2009 | Brister et al. |
| 2011/0288574 | A1* | 11/2011 | Curry .............. A61B 5/150022<br>606/185 |
| 2012/0095406 | A1* | 4/2012 | Gyrn .................... A61M 5/158<br>604/164.08 |
| 2012/0303043 | A1* | 11/2012 | Donnay ............... A61B 5/6849<br>606/129 |
| 2013/0150691 | A1* | 6/2013 | Pace .................. A61B 5/15087<br>600/347 |
| 2017/0000349 | A1 | 1/2017 | Krief et al. |
| 2017/0042457 | A1 | 2/2017 | Pace et al. |
| 2017/0188912 | A1 | 7/2017 | Halac et al. |
| 2017/0290533 | A1* | 10/2017 | Antonio .............. A61B 5/0022 |
| 2018/0235520 | A1 | 8/2018 | Rao et al. |
| 2018/0271414 | A1 | 9/2018 | Deck et al. |
| 2018/0360493 | A1* | 12/2018 | Baker .................. A61B 5/6849 |
| 2018/0368772 | A1 | 12/2018 | Gray et al. |
| 2019/0031422 | A1* | 1/2019 | Lai .......................... B01L 3/508 |
| 2019/0092536 | A1* | 3/2019 | Freedman ........ G01N 33/48778 |
| 2019/0223768 | A1 | 7/2019 | Muller et al. |
| 2019/0365297 | A1 | 12/2019 | Stafford |
| 2020/0178899 | A1* | 6/2020 | Chae .................. A61B 5/68335 |
| 2020/0290785 | A1* | 9/2020 | Emery .................. B65D 85/10 |
| 2020/0337642 | A1* | 10/2020 | Garai ..................... H05K 1/144 |
| 2021/0228156 | A1 | 7/2021 | Kouge et al. |

FOREIGN PATENT DOCUMENTS

| | | | | |
|---|---|---|---|---|
| CN | 107072532 | A | 8/2017 | |
| CN | 108344771 | A | 7/2018 | |
| CN | 109069005 | A | 12/2018 | |
| CN | 109924952 | A | 6/2019 | |
| JP | H07209986 | A | 8/1995 | |
| WO | WO-9610522 | A2 * | 4/1996 | ............. B65D 41/18 |
| WO | 2004002845 | A1 | 1/2004 | |
| WO | 2005051170 | A2 | 6/2005 | |

OTHER PUBLICATIONS

International Search Report dated Oct. 28, 2020 cited in PCT/CN2020/106618.

* cited by examiner

100

10(11)

80

50

圖17

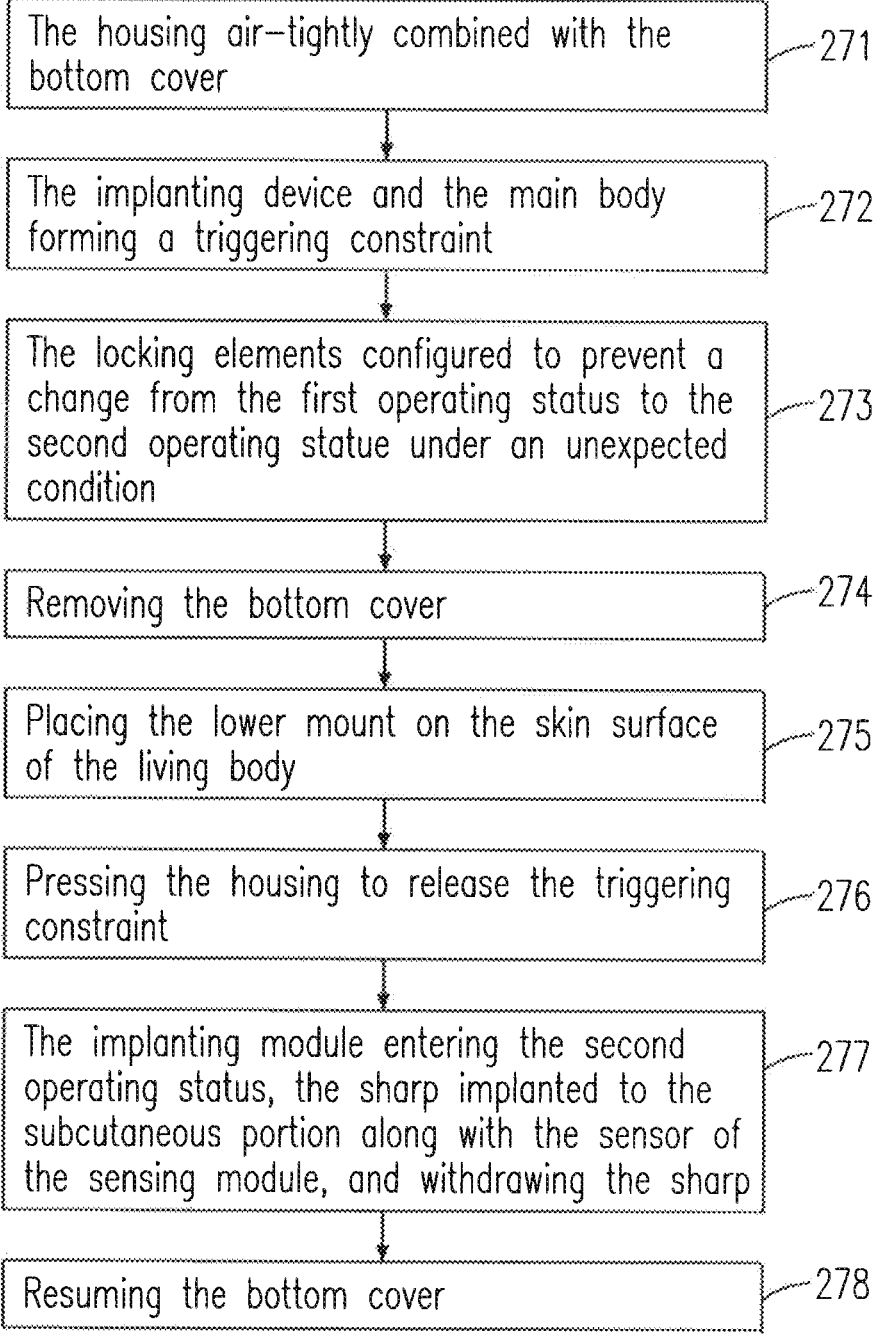

| | |
|---|---|
| The housing air-tightly combined with the bottom cover | 271 |
| The implanting device and the main body forming a triggering constraint | 272 |
| The locking elements configured to prevent a change from the first operating status to the second operating statue under an unexpected condition | 273 |
| Removing the bottom cover | 274 |
| Placing the lower mount on the skin surface of the living body | 275 |
| Pressing the housing to release the triggering constraint | 276 |
| The implanting module entering the second operating status, the sharp implanted to the subcutaneous portion along with the sensor of the sensing module, and withdrawing the sharp | 277 |
| Resuming the bottom cover | 278 |

PHYSIOLOGICAL SIGNAL MONITORING SYSTEM FOR FAST ASSEMBLY

PRIORITY

The application claims the benefit of U.S. Provisional Patent Application No. 62/882,140 filed on Aug. 2, 2019 and Taiwan Patent Application No. 109100992 filed on Jan. 10, 2020, which are fully incorporated by reference as if fully set forth.

FIELD OF THE INVENTION

The present invention is related to a container, and more particularly to a container for carrying sensor and its operating method.

BACKGROUND OF THE INVENTION

Chronic diseases such as diabetes or chronic cardiovascular diseases are more common than ever in the world due to the life style of people living in urban areas. Because of this, certain physiological parameters of those patients with chronic disease need to be routinely monitored to effectively control their condition so as to avoid deterioration and provide timely treatment.

However, much of the physiological data needs to be obtained through in vivo methods. In addition, it is necessary to obtain multiple items of measurement data each day in order to effectively do the monitoring. In order to avoid the patient's discomfort caused by multiple blood draws or body fluid extraction, some skilled people in the art tend to use a small sensing element implanted in the subcutaneous tissue for a relatively long time to match the signal processing component for fixing to the skin surface, which can be used for days. There is no need to remove, and data such as blood glucose, blood fat, cholesterol concentration or other measurements that provide physiological parameters can be collected and analyzed at any time to provide immediate physiological data monitoring. Similar concepts can also be applicable for implanting electronic devices such as chips into the skin of animals.

This type of physiological parameter measurement device, due to the difficulty of the manufacturing process, is traditionally made by separately assembling the sensor and an implanter. The sensor has reagents such as enzymes and needs to be placed in the body. The reagents need to be moisture-proof and sterilized during manufacture, but the implanters do not need these procedures.

According to conventional methods, such as the device and method disclosed in U.S. Pat. No. 9,693,713, the sensor is sealed in a container provided with a desiccant to isolate the source of pollution and maintain a dry sanitary condition. If the container cannot achieve the required sterilization condition, the container may further be stored in a blister shell. Before performing a physiological test, the user may tear off the blister shell, open the airtight container, assemble the sensor at the bottom of an implanter, and finally use the implant to place the sensor into the skin. Although the manufacturing process of such devices is relatively simple, the separate production processes of the two devices increases the manufacturing cost. For users, the implanter and the sensor must be assembled together before using, which is inconvenient and troublesome. Besides, in the descriptions of the specification of US20170188912 and U.S. Pat. No. 8,764,657B2, the implanter are opened by circulating manners, which have an issue of time consuming for it usually take at least one round, typically two to three rounds, to fully open it.

In addition, during the sensor implantation process, it can be basically divided into two steps: needle implantation and needle extraction. If any of these steps cannot be completed quickly, or if the steps are not coherent, it may cause pain or discomfort to the user.

Therefore, some issues, such as how to reduce the manufacturing process steps of the sensor and implanter while enhancing the user's convenience, effectively maintaining the dry condition of the physiological parameter sensor before implantation, and allowing the implantation in a hygienic and painless way are technical problems to be solved.

SUMMARY OF THE INVENTION

In accordance with one aspect of the present invention, an implantation device for prompt subcutaneous implantation of a sensor to measure a physiological signal of an analyte in a biofluid of a living body is disclosed. The implantation device includes a housing, an implantation module, a detachable module and a bottom cover. The housing has a bottom opening. The implantation module includes an implanting device and a needle extracting device. The detachable module includes the sensor detachably engaged with the implantation module; and a base configured to mount the sensor thereon. The bottom cover is detachably coupled to the bottom opening so that the housing and the bottom cover together form an accommodating space. The implantation module and the detachable module are accommodated in the accommodating space. The bottom cover has an operating portion configured to bear a force, and a supporting portion is formed on the opposite end of the operating portion. A distance between the operating portion and the supporting portion and the force form an operating moment allowing a user to cause thereby a side detachment between the bottom cover and the housing. After the bottom cover is separated from the bottom opening, the housing is operated to cause the implantation module to release an action force to cause the detachable module to be detached from the implantation module and subcutaneously implanting a portion of the sensor to measure the physiological signal.

In accordance with another aspect of the present invention, a physiological signal monitoring system for fast assembly and measuring a physiological signal of an analyte in a living body is provided. The physiological signal monitoring system comprises an implantation device and a transmitter. The implantation device includes a housing having a bottom opening, an implantation module including an implanting device and a needle extracting device, a detachable module including a sensor and a base, and a bottom cover. The sensor is detachably partially implanted into the living body. The base is for disposing the sensor thereon after the sensor is partially implanted into the living body. The bottom cover is detachably coupled to the bottom opening so that the housing and the bottom cover together form an accommodating space. The transmitter is coupled with the base after the sensor is partially implanted into the living body for transmitting the physiological signal that is measured by the sensor, wherein the bottom cover has an operating portion configured to bear a force, and a supporting portion is formed on an opposite end of the operating portion, a distance between the operating portion and the supporting portion and the force form an operating moment, after a side detachment between the bottom cover and the housing is initiated by the operating moment, the bottom cover is departed from the bottom opening, and the housing is put under an operating condition to operate the implantation module to cause the detachable module to be detached from the implantation module and subcutaneously implanting a portion of the sensor to measure the physiological signal.

In accordance with a further aspect of the present invention, a physiological signal monitoring system for fast assembly and measuring a physiological signal of a living body having a skin surface is provided. The physiological signal monitoring system comprises a housing having a bottom opening, a mechanism module disposed in the housing, a sensor module detachably disposed in the mechanism module to be attached on the skin surface, and a bottom cover detachably coupled with the bottom opening so that the housing and the bottom cover together form an accommodating space, wherein the mechanism module and the sensor module are accommodated in the accommodating space, the bottom cover has an operating portion configured to bear a force, and a supporting portion is formed on the opposite end of the operating portion, a distance between the exertion portion and the supporting portion and the force form an operating moment, and after a side detachment between the bottom cover and the housing is initiated via the operating moment, which causes the bottom cover to be removed from the bottom opening, the housing is put under an operating condition to cause the sensor module to be attached on the skin surface for measuring the physiological signal.

The novel design in the present invention can fully satisfy the requirements of reducing manufacturing cost. Thus, the present invention has utility for industry.

The objectives and advantages of the present invention will become more readily apparent to those ordinarily skilled in the art after reviewing the following detailed descriptions and accompanying drawings, in which:

BRIEF DESCRIPTION OF THE DRAWINGS

FIG. 27 is a schematic operation flow diagram of the air-tight and desiccating container according to the present invention;

DETAILED DESCRIPTION OF THE PREFERRED EMBODIMENT

Figure 1:
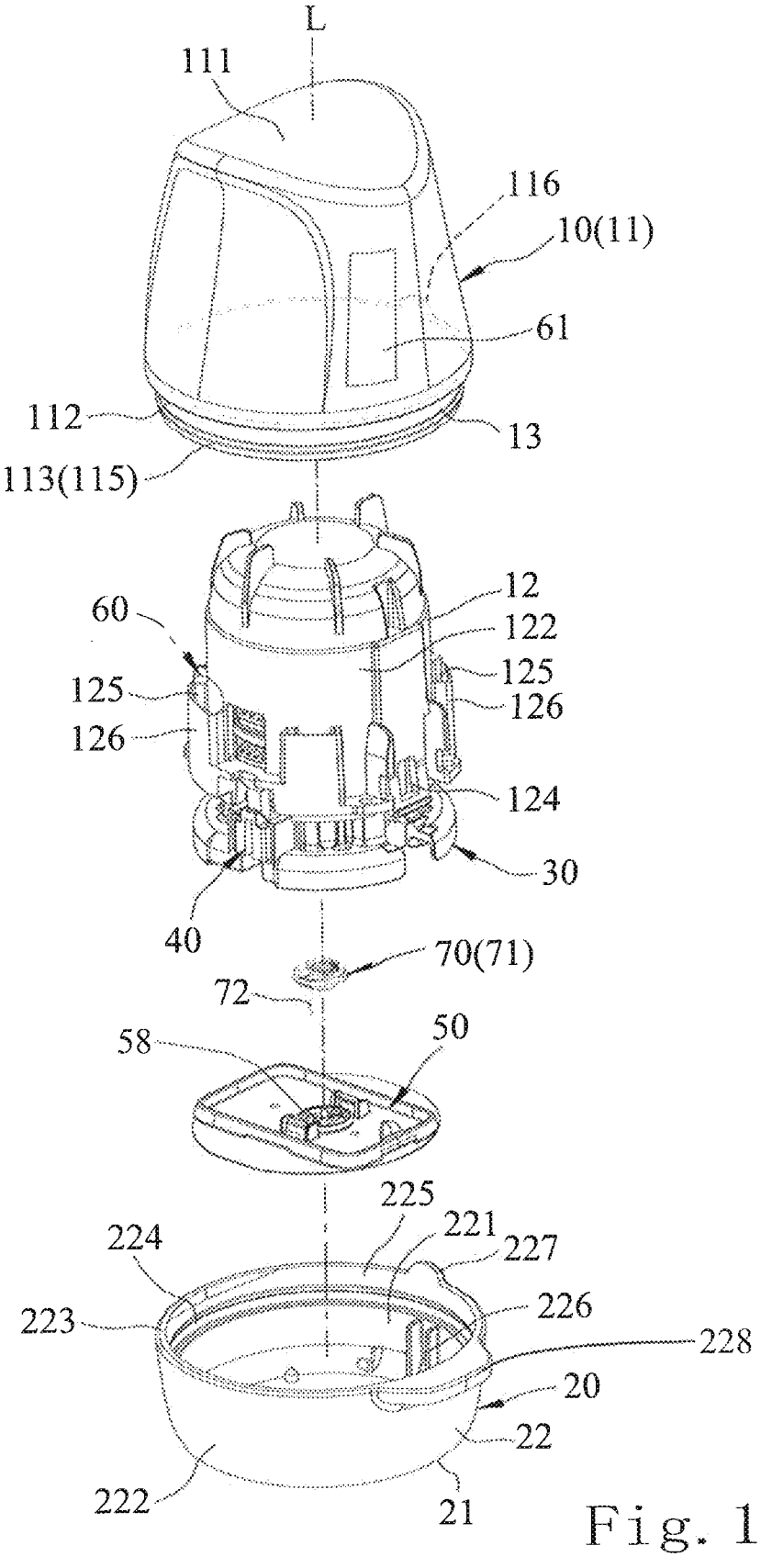
FIG. 1 is an assembly diagram of the air-tight and desiccating container for carrying a sensor and implanting the sensor into a subcutaneous portion of a living body according to an embodiment of the present invention.

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

The present invention of air-tight and desiccating container incorporates the implanting device with the sensing device, and maintains a dry environment for the devices. Please refer to FIGS. 1-10. According to FIG. 1, the desiccating container 100 is formed therein an air-tight space due to the air-tight joint maintained by the housing 11 and the bottom cover 20. The casing assembly 10 includes the housing 11, the lining piece 12 disposed inside the housing 11 and the leak-proof ring 13 which is selectively added and disposed around the housing 11. The air-tight space commonly formed by the housing 11 and the bottom cover 20 is for accommodating other elements such as the implanting module 30, the lower mount base 50, the sensor assembly 70 and the desiccating element 60. The lower mount base 50 and the sensor assembly 70 will be separated from the desiccating container 100 after the completion of the implanting process and compose a form of a module to be disposed on the skin surface of the living body that a sensor needs to be implanted thereinto. Therefore, the combination of the lower mount base 50 and the sensor assembly 70 can be considered as a detachable module. It can be understood, according to the illustrations in FIGS. 3 and 4, that the lower mount base 50 and the sensor assembly 70 are separately disposed at different locations in the state of storage and to be implanted.

Referring to FIGS. 1-4, the shape of the housing 11 is like a cup, and a top wall 111 is located at the cup-bottom like portion. There is a bottom opening on the lower surface 112 opposite to the top wall 111 along the axis L. According to the present embodiment, a first joint portion to be jointly connected to the bottom cover 20 is defined on the bottom opening of the housing 11. The first joint portion is coupled to the bottom cover 20 through, but not limited to, a sleeving engagement (hard interfering). The housing 11 further includes a matching portion 116 having a concave shape. In one embodiment, to allow a person to observe the desiccating condition of the desiccating element 60, a desiccation indicator 61 such as a cobalt-containing humidity indicator or a cobalt-free humidity indicator, can be disposed at the location of the housing 11 or the bottom cover 20 which is made of transparent or translucent material. Another example for the desiccation indicator 61 is a printed layer of a zeolite-containing resin, which can be judged by absorbing moisture to make the resin layer transparent. The desiccation indicator 61 can be used by users to observe the dryness in the container so as to avoid using abnormal products.

The lining piece 12 has a shape of a hollow cylindrical cup, and is sleeved in the housing 11. The lining piece 12 is in close contact with the inner surface 117 of the housing 11, and has an inner periphery surface 121 that can define the accommodating space 14 for accommodating the implantation module 30, an outer peripheral surface 122 opposite to the inner peripheral surface 121, a pair of actuating portions 123 protruding from the inner peripheral surface 121, a pair of locking portions 124 disposed along the axis L from a side of the actuating portions 123 respectively and a plurality of slot seats 126 protruding from the outer peripheral surface 122 and defining the containing grooves 125 with the outer peripheral surface 112 respectively. The locking portions 124 have through holes communicating the outer peripheral surface 122 with the inner peripheral surface 121. The containing groove 125 can be used to place the desiccant 60.

Figure 32:
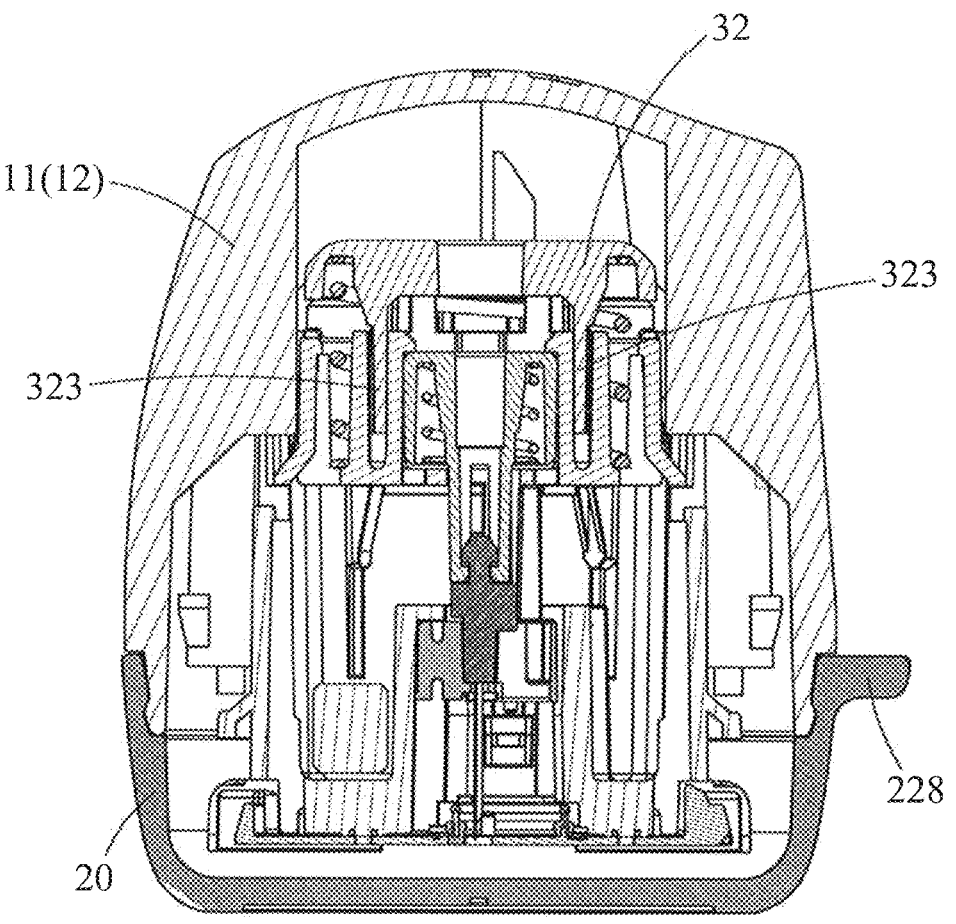
FIG. 32 is a schematic sectional view taken along the x-x direction of one of the embodiments shown in FIG. 2B.
Figure 33:
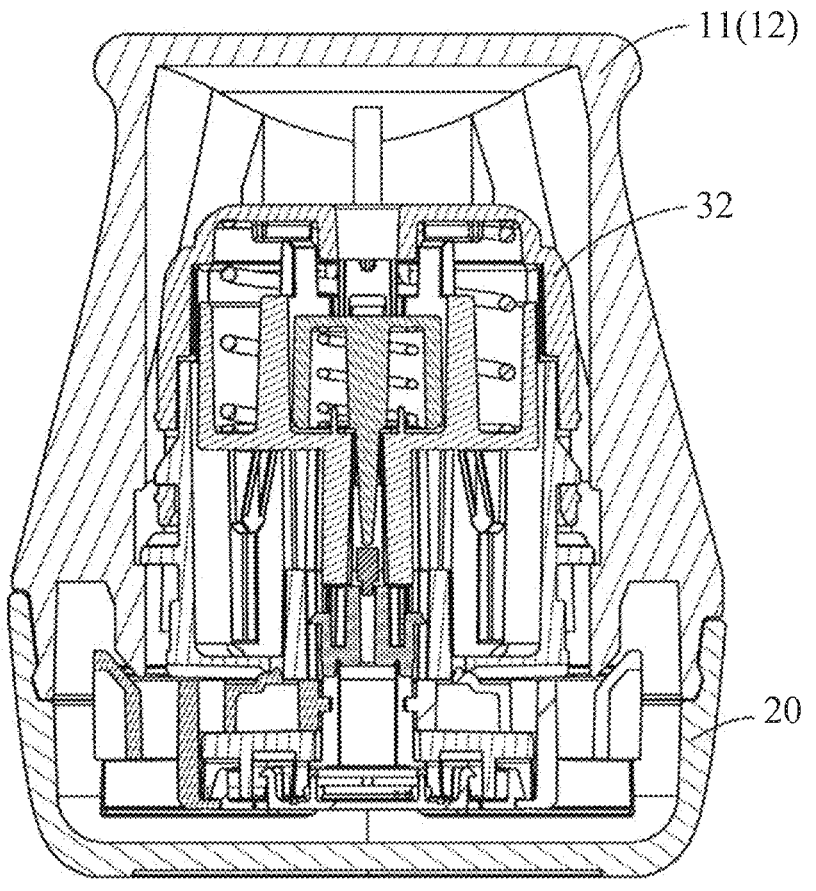
FIG. 33 is a schematic sectional view taken along the y-y direction of one of the embodiments shown in FIG. 2B.

Since the lining piece 12 and the casing 11 are closely fitted via a plurality of mating portions 127, the relative positions of the two can be unchanged. The gap formed between the lining piece 12 and the casing 11 due to the existing of the plurality of mating portions 127 on the top surface of the lining piece 12 can be furnished with a desiccant 60. In this embodiment, the lining piece 12 may define a desiccant accommodating space on the top of the lining piece 12 and at least one of a plurality of containing grooves 125 extending from the side wall of the lining piece 12. In another embodiment, the inner peripheral surface 121 of the lining piece 12 may also include a desiccant accommodating space (not shown). According to another embodiment of the present invention, as shown in FIGS. 32 and 33, the lining piece 12 can be regarded as a part of the housing 11 or vice versa, which means that the lining piece 12 and the housing 11 can be independent components or the two components can be formed integrally, without departing from the scope of the present invention.

The bottom cover 20 is detachably mounted to the housing 11, and has a chassis portion 21 substantially perpendicular to the axis L and a peripheral wall 22 extending from the periphery of the chassis portion 21. The peripheral wall 22 has an inner side surface 221, an outer side surface 222 opposite to the inner side surface 221, a brim 223 connected between the inner side surface 221 and the outer side surface 222, a ring groove 224 recessed in the inner side surface 221 to which the convex ring 115 can be embedded, a pair of blocking portions 226 protruding from the inner side surface 221, and a slightly semicircular plate-shaped positioning piece 227 protruding from the brim 223. The bottom opening of the housing 11 matches the configuration of the bottom cover 20. The positioning piece 227 can be nested in the matching portion 116. The matching between the positioning piece 227 and the matching portion 116 provides a user with the function of foolproof alignment when operating to open and close the container. In addition, when the internal components of the desiccating container have a directional requirement, the combination of the matching portion 116 and the positioning piece 227 can be used as a set of foolproof alignment, which is beneficial to improve production efficiency. Besides, the matching portion 116 can also be used as a positioning member for the housing 11 to be used as a reference point for estimating the amount of deformation of the opening of the housing 11 to make the opening of the housing a round appearance during injection molding, which helps in the airtight process.

The outer side surface 222 of the bottom cover 20 has an operating portion 228 adjacent to the brim 223 and protruding from the outer side surface 222. The force applying portion 228 makes it easy for the user to open and remove the bottom cover 20. Furthermore, the operating portion 228 is provided to control the opening force to no more than 2 kilogram force (kgf), so that the container can be easily opened and is resistant to negative pressure, and can be quickly disassembled by the user with less effort.

Figure 3:
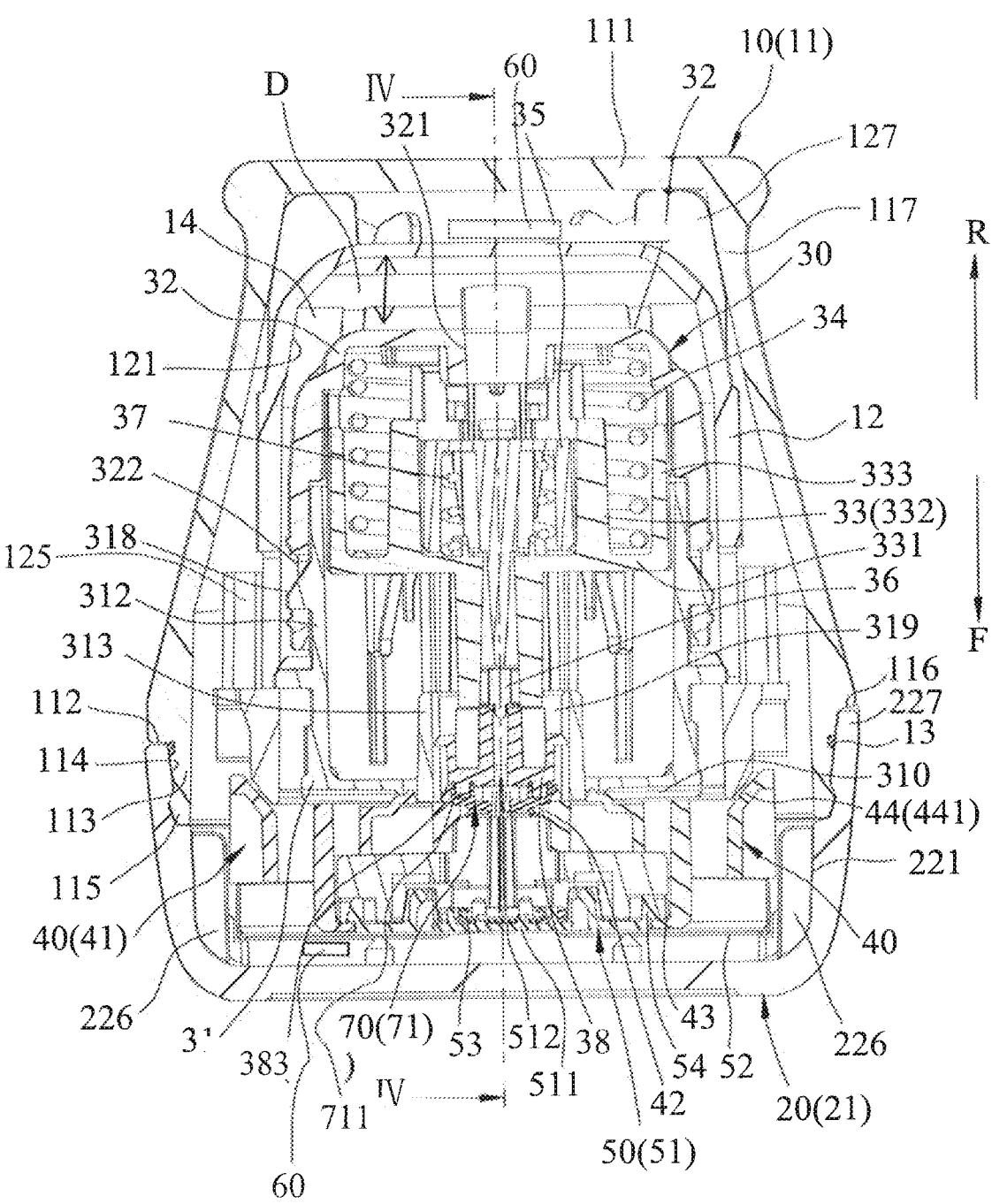
FIG. 3 is a schematic sectional view taken along the x-x direction of one of the embodiments shown in FIG. 2B, illustrating the container in a state of storage and to be implanted.

According to this embodiment, the inner side surface 221 of the bottom cover 20 defines a second joint portion that is to be engaged, but is not limited to other ways, with the first joint portion of the housing 11. In another embodiment, the leak-proof ring 13 formed of an elastic washer with elastic material can also be sleeved on the outer ring surface 114 of the bottom ring portion 113. The leak-proof ring 13 is arranged on one side of the ring groove 224, and can be air-tightly sleeved on the ring portion 225 disposed on the outer side of the leakage preventing ring 13. As shown in FIG. 3, when the housing 11 and the bottom cover 20 are assembled, the leak-proof ring 13 can make the combination of the two at an air-tight condition. According to another embodiment, the ring groove 224 of the bottom cover 20 and the convex ring portion 115 of the housing 11 may also form a joint in an airtight condition. In order to provide an air-tight storage environment for the desiccating container 100, according to another embodiment, the bottom cover 20 may also be implemented in the form of an aluminum foil (not shown), which may also provide a sealing effect.

Results from the negative pressure test for the desiccating container stored in different temperature and humidity environments and was taken out at different times to confirm the airtight function and verify the daily average moisture absorption of the desiccating container was done through the weighing test. According to the experimental results, the moisture absorption in the desiccating and airtight storage container of the present invention is not more than 200 mg per day, or not more than 50 mg per day, or not more than 1 mg per day, or not more than 0.5 mg per day, or not more than 0.3 mg per day, or no more than 0.25 mg per day. In another embodiment, the desiccating and airtight container is allowed to reach a storage condition of relative humidity of 0 to 100% and a temperature of 0 to 45° C., or a storage condition of relative humidity of 0 to 100% and a temperature of 0 to 40° C., or the storage condition with relative humidity of 10 to 90% and temperature of 4 to 30° C., and maintaining a storage period of at least 2 years or at least 1 year, both have good air-tight effects. The present invention is not limited by the embodiments of hard interference pattern disclosed by the examples.

It is worth mentioning that a hinged connection (not shown) can also be provided between the bottom cover 20 and the housing 11 of the desiccating container 100. By utilizing the present invention of can opening design with the convex ring and the ring groove, while operating the desiccating container 100 for the sensor implantation, the housing 11 is more easily pressed against the surface of the biological skin for implantation. Compared with the screw-rotating can opening design, the convex ring and ring groove sleeving design of the present invention makes the manufacturing process simpler and can reduce the probability of production mold wearing out, which is beneficial to improve process yield.

Figure 4:
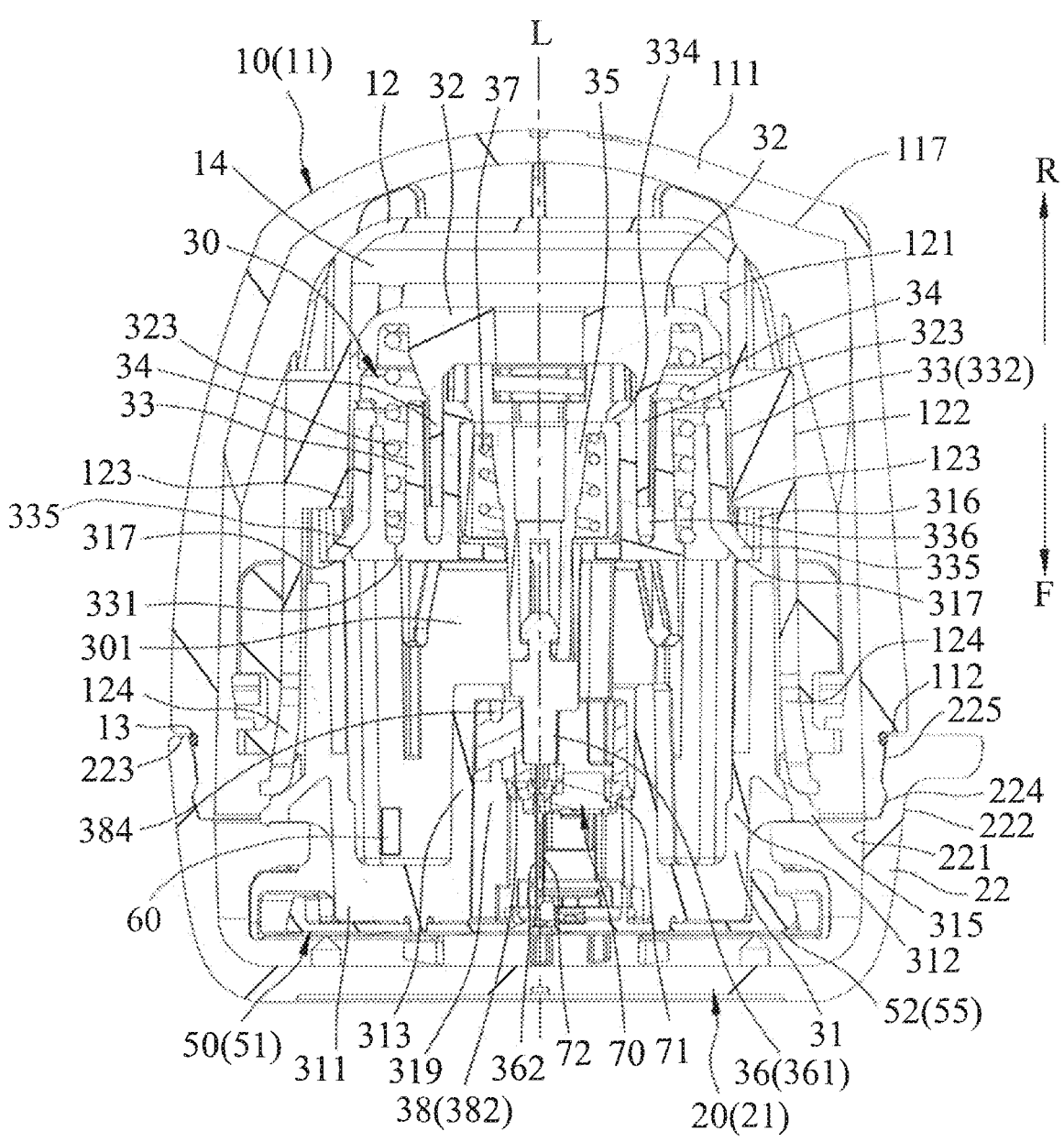
FIG. 4 is a schematic diagram showing a sectional view taken along the line IV-IV of the embodiment illustrated in FIG. 3 or taken along the y-y direction of one of the embodiments in FIG. 2B.
Figure 31:
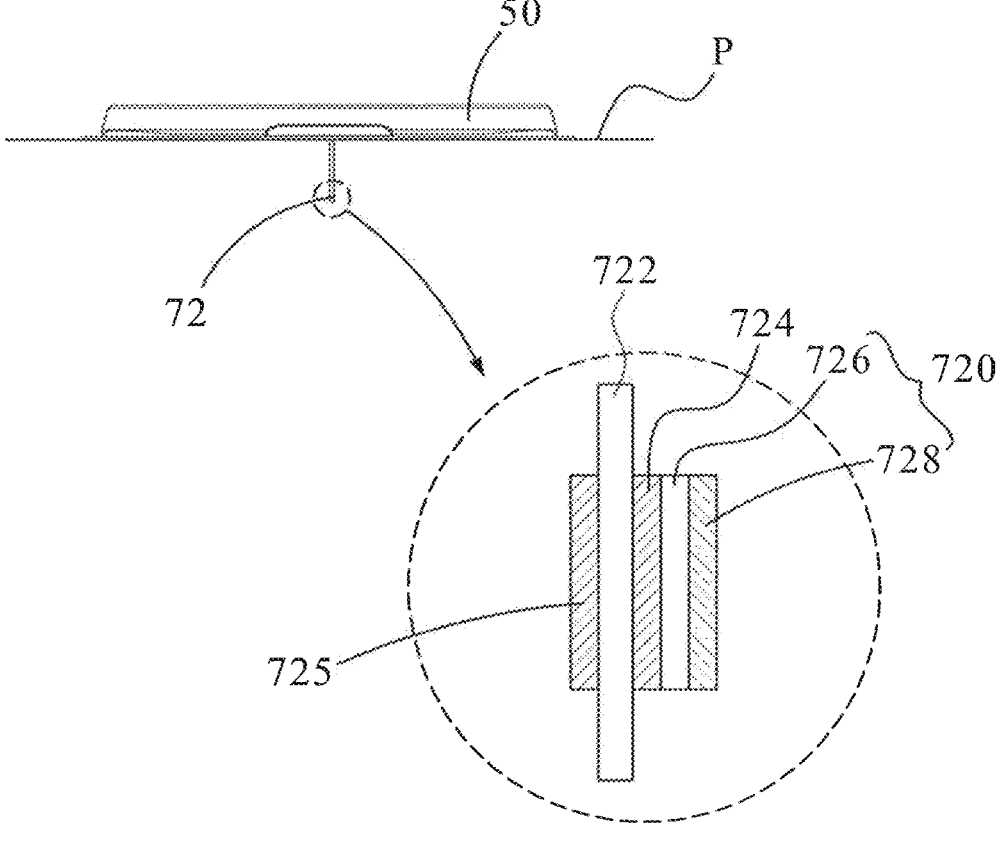
FIG. 31 is a schematic sectional view of the removal module according to the present invention disposed on the surface of a living body.

The sensor assembly 70 includes a sensor 72 as shown in FIGS. 3-4 and 31. The sensor 72 is to be implanted into the cortex P, the subcutaneous portion, of the living body to measure the living body's physiological signals. The sensor assembly 70 includes a sensor base 71 and a sensor 72 which connects to the sensor base 71 and is partially retained in the implantation needle 362. The sensor base 71 has a plurality of recessed engaging portions 711 configured to be engaged with the connecting portions 383 of the auxiliary implantation seat 38. The sensor assembly 70 can also be regarded as a single module. For example, the sensor 72 may include a substrate 722, and at least one working electrode 724 and a reference or counter electrode 725 are disposed on the substrate 722. At least the working electrode 724 has a chemical reagent 720 including at least one analyte-responsive enzyme 726 and polymer membrane layer 728. The chemical reagent 720 is configured to obtain data on certain physiological parameters in the living body, such as glucose concentration or other parameters in interstitial fluid.

The sensor 72 is not limited to other types of electrode arrangement structures. The sensor 72 must be kept airtight and dry while storage and before implantation, so the accommodating space 14 of the airtight desiccating container 100 for carrying the sensor assembly 70 is provided with the desiccant 60 to maintain the long-term stability period of the reagent, such as one or more years. The gaps between the elements in the desiccating container 100 of the present invention can be used as venting holes for the desiccant 60, and communicate with the sensor 72, so that the desiccant 60 maintains a good function for moisture absorption. Notably, in another embodiment, the air-tight container 100 of the present invention does not even need to place a desiccant 60. Under a state of excellent air-tightness, the container interior can have a very low humidity as at the initial production stage, which keeps the sensor away from being affected by humidity and maintains the long-term efficacy of the chemical reagent. Thus, the sensor 72 can have a consistently good accurate performance for one year or two years or even longer, during the storage period.

The desiccant 60 may be disposed at any appropriate position inside the desiccating container 100. As shown in the embodiment illustrated in FIG. 1 or 2A, the desiccant 60 is disposed in the containing groove 125 of the lining piece 12, and the implanting module 30 carrying the sensor assembly 70 is located in the accommodating space 14 inside the lining piece 12. From another perspective, the liner 12 is disposed between the housing 11 and the implanting module 30. Desiccant 60 can also be placed between the plurality of mating portions 127 on the outer peripheral surface 122 of the liner 12. According to another embodiment, as shown in FIGS. 2A and 3-4, the desiccant 60 may be sandwiched between the outer peripheral surface 122 of the lining piece 12 and the housing 11, or disposed on the inner peripheral surface 121. The desiccant 60 may also be disposed at an appropriate position of the implanting module 30 or the bottom cover 20, or the desiccant 60 may be disposed near the sensor assembly 70, or the desiccant 60 may be integrally formed with the sensor base 71. The desiccant 60 can be combined and arranged at different positions according to environmental requirements. The desiccant 60 can be a desiccant-incorporated polymer, a water-absorbing material, a hygroscopic material, a molecular sieve drying sheet, a desiccant-incorporating plastic sheet, or a dry sheet formed by injection molding with internal components of the container 100.

The implanting module 30 is installed in the accommodating space 14, and includes a main body 31 having a hollow cylindrical shape, an main cover 32 connected to the main body 31 and defining a displacement space 301 together with the main body 31, a needle implanting seat 33 movably disposed in the displacement space 301 along the axis L, a first elastic element 34 disposed between the needle implanting seat 33 and the main cover 32 in a pre-compressed manner, a needle extracting seat 35 slidably installed inside the needle implanting seat 33 along the axis L, a needle implanting piece 36 connected to the needle extracting seat 35, and a second elastic element 37 disposed between the needle implanting seat 33 and the needle extracting seat 35 in another pre-compressed manner. The first elastic element 34 is configured to provide the needle implanting seat 33 with elastic force to move away from the main cover 32 along the implanting direction F. The second elastic element 34 is configured to provide the needle extracting seat 35 with elastic force to move along the needle extracting direction R. The components in the implanting module form a driving group to drive the needle implanting piece 36 causing the implanting module 30 to release a force to implant the sensor 72 underneath the skin of a living body.

The main body 31 has a bottom wall 311, a cylinder wall 312 intersecting and connected to the bottom wall 311, a hollow tubular duct 313 protruding from the bottom wall

311, two elastic pieces 314 connected to the cylinder wall 312 and opposite to each other, and a pair of latching portions 315 which can be engaged with the locking portions 124 respectively. The cylinder wall 312 has a pair of slide grooves 310 extending along the axis L, a pair of recessed portions 316, and a pair of stopping portions 317 adjacent to the recessed portions 316, and a pair of buckle ears 318. The duct 313 has a push-out hole 319 which is narrower inward and wider outward. The slide grooves 310 is connected to the pushing holes 319, and the elastic pieces 314 have elasticity that may cause bias relative to the axis L. The latching portions 315 are respectively disposed on the movable ends of the elastic pieces 314.

The main cover 32 has a central hole 321 corresponding to the axis L, a pair of buckle holes 322, which can be buckled on the buckle ears 318 respectively, and a pair of constraint elements 323 disposed along the axis L and opposite to each other.

The needle implanting seat 33 has a flat plate portion 331, an inner cylindrical member 332 intersecting and connected to the flat plate portion 331, an outer cylindrical member 333 intersecting and connecting to the flat plate portion 331 and surrounding the inner cylindrical member 332, a limiting element 334 disposed on the inner tube member 332 for keeping the needle extracting seat 35 at a constant location relative to the needle implanting seat 33, a pair of buckle portions 335 respectively disposed on the outer cylindrical member 333 and detachably sitting on the stopping portions 317, and a pair of limiting grooves 336 extending parallel to the parallel axis L and adjacent to the limiting element 334. The buckle portions 335 are in the shape of springs and have elasticity that may cause bias relative to the axis L.

According to one embodiment of the present invention, the first and the second elastic elements 34, 37 are compressing springs.

According to one embodiment of the present invention, the needle implanting piece 36 has a main body portion 361 and a needle 362 having a hollow shape and connected to the main body portion 361.

Notably, the implanting module 30 further includes a auxiliary implantation seat 38 detachably disposed on the needle-implanting piece 36, and the sensor assembly 70 detachably maintains a position relative to the auxiliary implantation seat 38. The auxiliary implantation seat 38 has a base mount 381, three fins 382 extending outward from the base mount 381 and a plurality of connecting portions 383 protruding from the bottom of the base 381 and having a tenon shape. The fins 382 each have a plurality of recesses 384, and are allowed to be compressed in a radial direction perpendicular to the axis L and have the ability to spring outward after being compressed. Due to the constraint position formed by the auxiliary implantation seat 38 and the main body 31 before the needle is implanted, the left-right deflection and pulling can be avoided when the needle is implanted underneath the skin of the biological body. It improves the stability of the needling and reduces the feeling of pain on the biological body or the patient. The sensor assembly 70 can be detachably carried on the auxiliary implantation seat 38. In other embodiments, the auxiliary implantation seat 38 may also be integrated with other components in the implant module 30 or in sensor assembly 70 (not shown).

The fixing members 40 are respectively installed in the slide grooves 310 of the main body 31, can slide along the slide grooves 310, and each of which has a pushing portion 41 corresponding to the blocking portions 226, a supporting portion 42 opposite to the pushing portion 41, a first hook 43 disposed between the pushing portion 41 and the supporting portion 42, and a guiding portion 44 disposed between the pushing portion 41 and the supporting portion 42 and the guiding portion 44 having a guide slanting surface 441.

The lower mount base 50 is detachably positioned relative to the main body 31. The sensor component positioning portion on the lower mount base 50 includes a groove 78 configured to allow the sensor assembly 70 to be buckled and positioned after detaching from the auxiliary implantation seat 38. The lower mount base 50 has a base mount 51, an adhesive pad 52 fixed to the base mount 51, a group of buckles 53 disposed on the base mount 51, a second hook 54 configured for detachably hooked with the first hooks 43, and a release layer 55 releasably attached to the adhesive pad 52 and can be removed prior to the manufacturing process.

The base mount 51 has a sensor assembly positioning portion 511 for positioning the sensor assembly 70. The sensor assembly positioning portion 511 can be an elastic sheet material with a closed top surface 512 to prevent contamination to the sensor assembly 70. The buckles 53 protrude from the top surface 512 and have an inverted V-shaped cross section, and are elastic at least in one direction.

Figure 38:
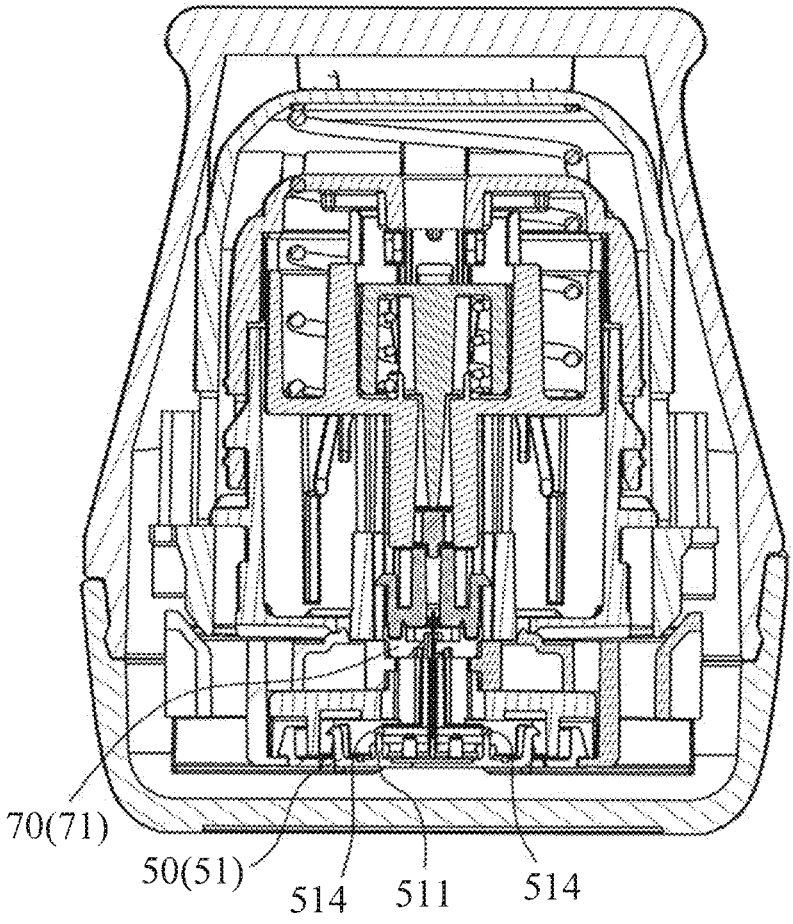
FIG. 38 is a schematic sectional view taken along the x-x direction of one of the embodiments shown in FIG. 2B.
Figure 39:
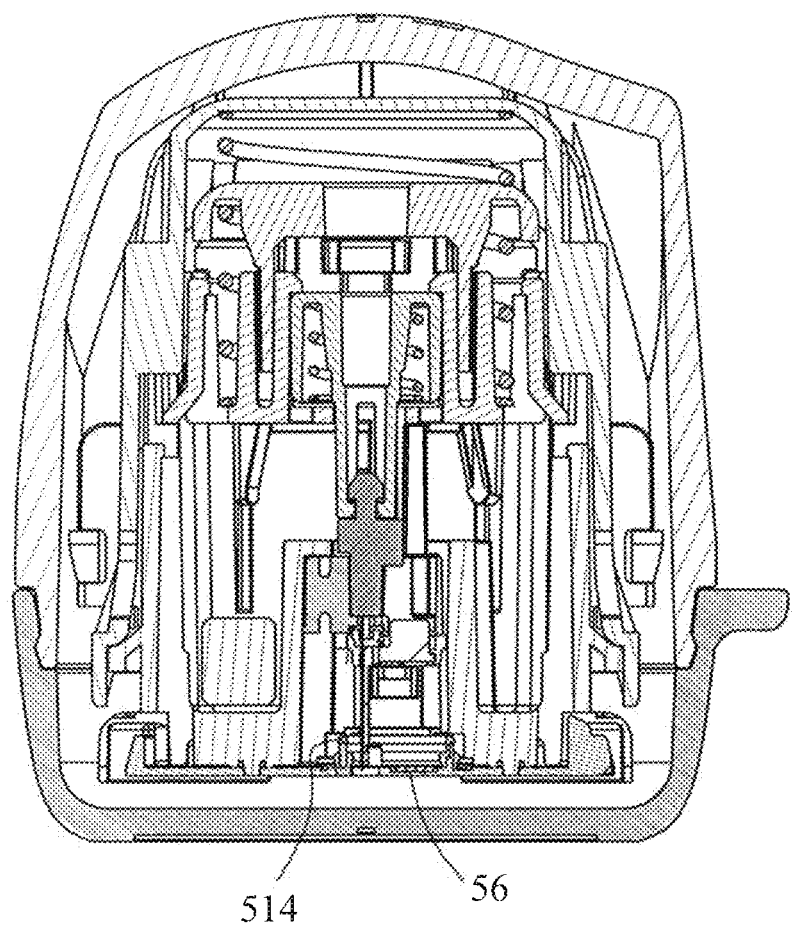
FIG. 39 is a schematic sectional view taken along the y-y direction of one of the embodiments shown in FIG. 2B.
Figure 40:
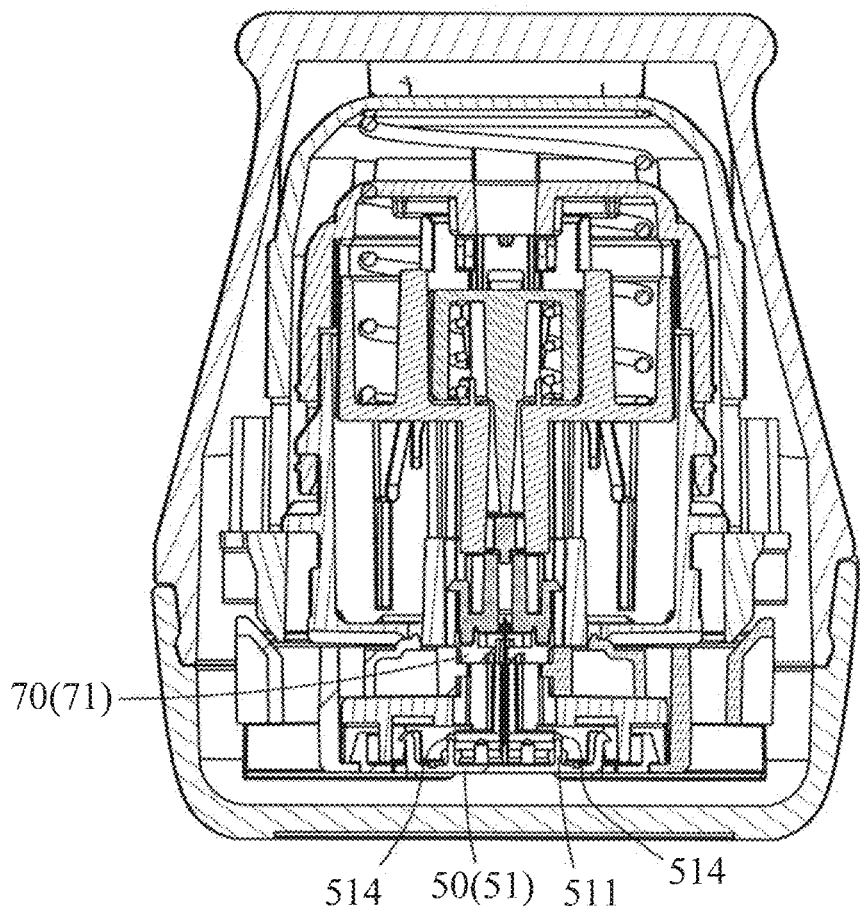
FIG. 40 is a schematic sectional view taken along the x-x direction of one of the embodiments shown in FIG. 2B.
Figure 41:
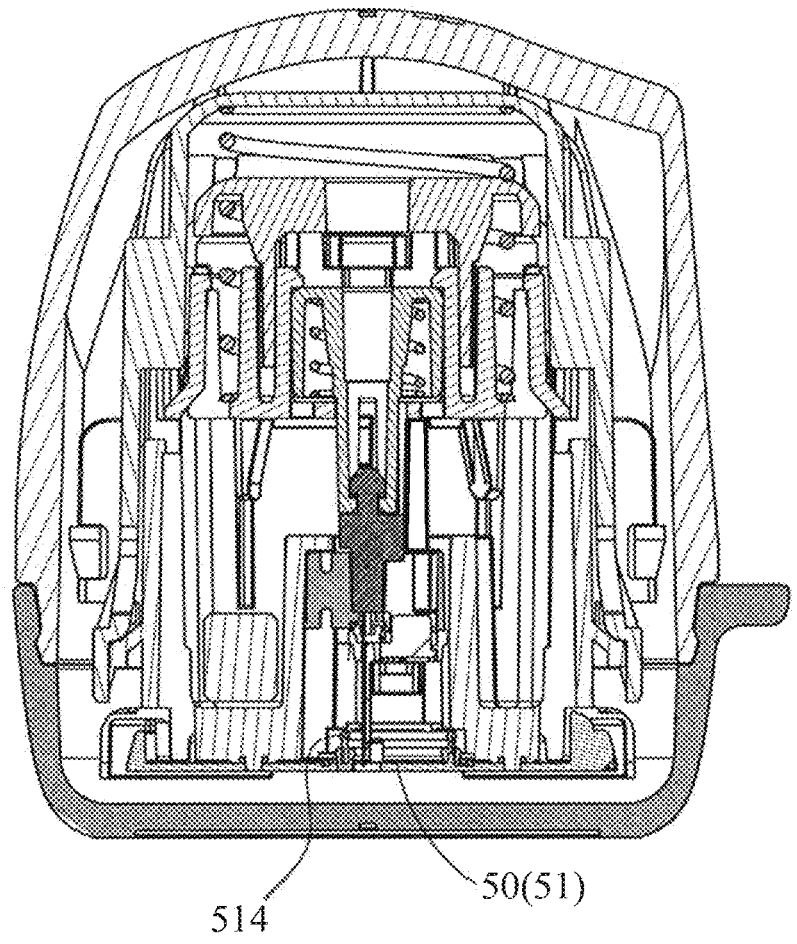
FIG. 41 is a schematic sectional view taken along the y-y direction of one of the embodiments shown in FIG. 2B.

In another embodiment (referring to FIGS. 38-39), the buckles 53 can be replaced with a double-sided sticker 56, the bottom of the sensor base 71 is bonded to the double-sided sticker 56, and the sidewall of the sensor base 71 is sandwiched by the sensor assembly positioning portion 511. In another embodiment (referring to FIGS. 40-41), the sensor assembly positioning portion 511's elastic ring 514 and the sensor base 71 can be press-fitted to cause the sensor assembly 70 to be positioned on the lower mount base 50, and the group of buckles 53 are no longer necessary. In another embodiment, the lower mount base 50 and the sensor assembly 70 may be pre-assembled (not shown).

In order to further describe the effects of the cooperation of the elements of the present invention, the use of technical means, and the expected effects, it will be explained as follows, which is believed that the skilled persons in the art can have a deeper and specific understanding of the present invention.

In the embodiment shown in FIGS. 3 and 4, when the first embodiment of the desiccating and airtight container 100 of the present invention is assembled, the bottom cover 20 is air-tightly closed to the housing 11, in an unused state, the ring groove 224 embedded by the convex ring 115 can be used to air-tightly combine the bottom cover 20 and the housing 11, an air-tight space is formed inside the casing assembly 10 (or the housing 11) and the bottom cover 20, and in combination with the desiccant 60, the purpose of moisture resistance can be achieved so as to ensure the detection accuracy of the sensor 72. In another embodiment, the convex ring 115 may be disposed on the bottom cover 20, and the ring groove 224 is provided on the housing 11.

In the storage state, the position of the needle implanting seat 33 in the displacement space 301 is adjacent to the main cover 32, and the stopping portions 317 of the main body 31 and the buckle portions 335 of the needle implanting seat 33 form a state of constraint. The needle implanting seat 33 is located in an upper position. The first elastic element 34 is pre-compressed between the needle implanting seat 33 and the main cover 32, and contains a releasable elastic force. The constraint elements 323 are respectively inserted in the limiting grooves 336, and are configured to restrict the limiting element 334 from radial deflection. The limiting element 334 is used to generate a latch on the needle extracting seat 35 positioned relative to the needle implanting seat 33, so that the displacement of the needle implanting seat 33 in the implantation direction F is restricted. There is a distance D between the main cover 32 and the lining piece 12.

When the desiccating container 100 is completely assembled and not yet used, the fixing members 40 abut against the bottom cover 20. More specifically, the pushing portions 41 of the fixing members 40 are respectively constrained by the blocking portions 226 of the bottom cover 20. The method of setting of the fixing members 40 can generate a movement restriction for the lining piece 12 to prevent the drying container 100 from false triggering due to accidentally falling and causing the internal components to scatter or malfunction, to ensure the purpose of effective use. Meanwhile, the supporting portions 42 of the fixing members 40 are also used to generate a supporting effect on the sensor base 71 of the sensor assembly 70, and the first hooks 43 are engaged in the second hooks 54, so that the lower mount base 50 is positioned relative to the main body 31.

Figure 5:
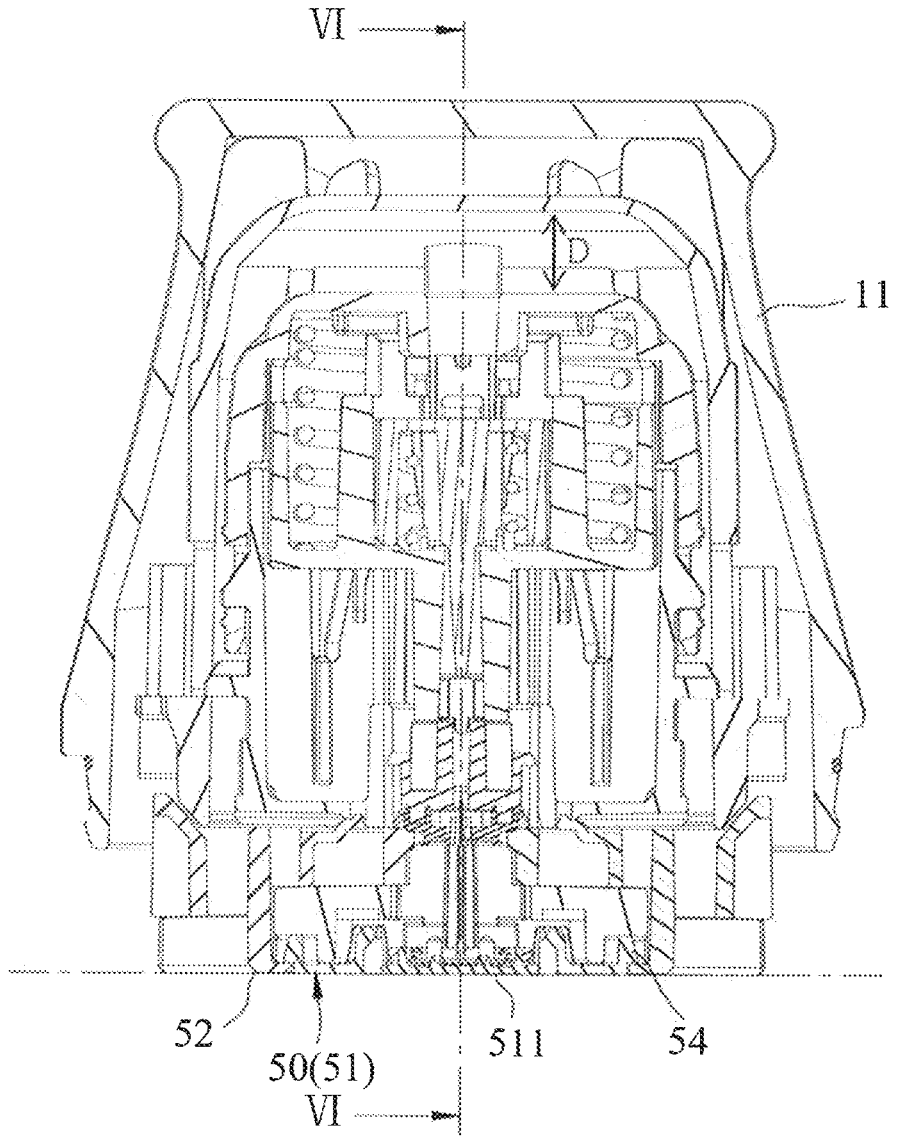
FIG. 5 is a schematic diagram of the embodiment shown in FIG. 1, illustrating that the bottom cover is removed and is at the stage of being prepared for the implanting.
Figure 6:
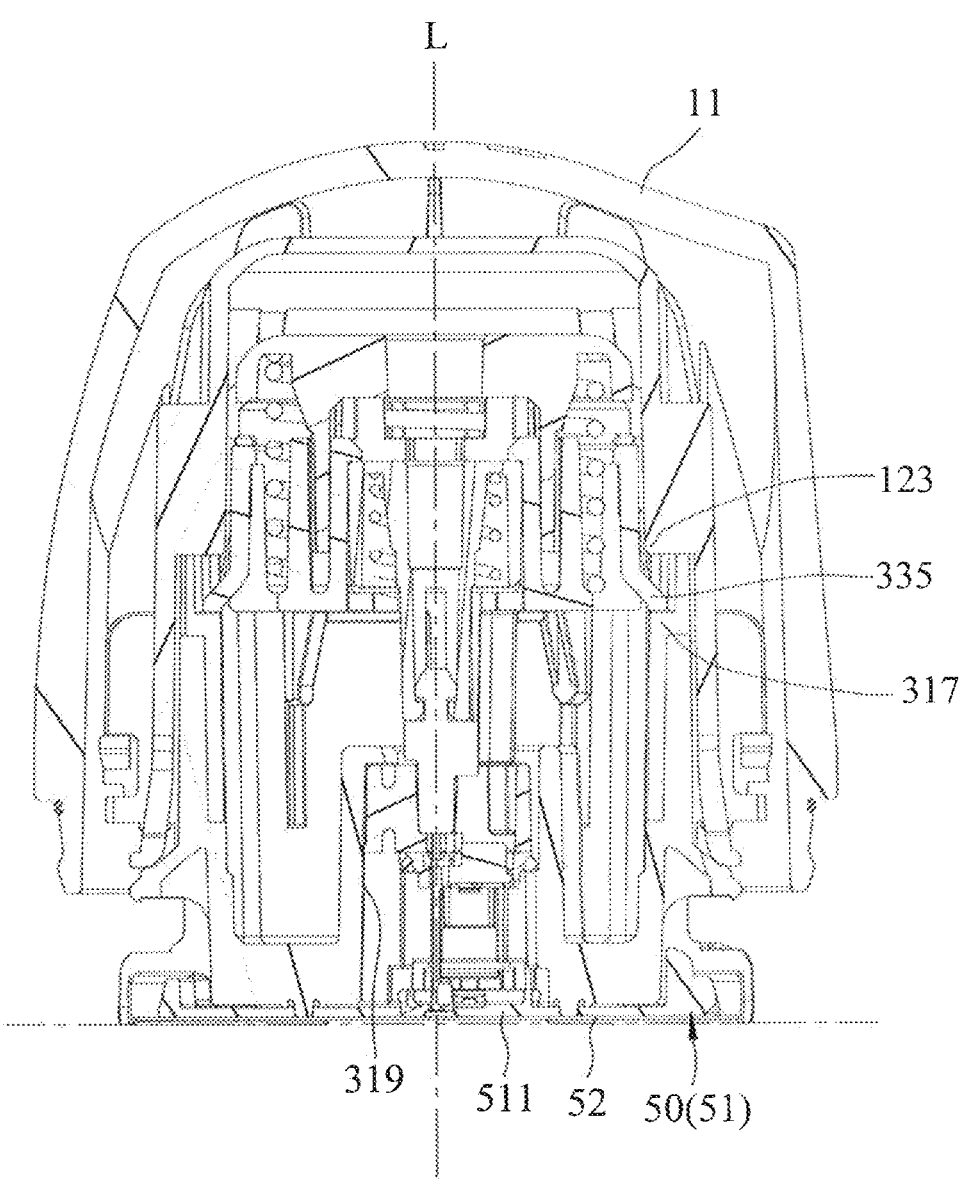
FIG. 6 is a sectional diagram taken along the line VI-VI of the embodiment illustrated in FIG. 5.
Figure 7:
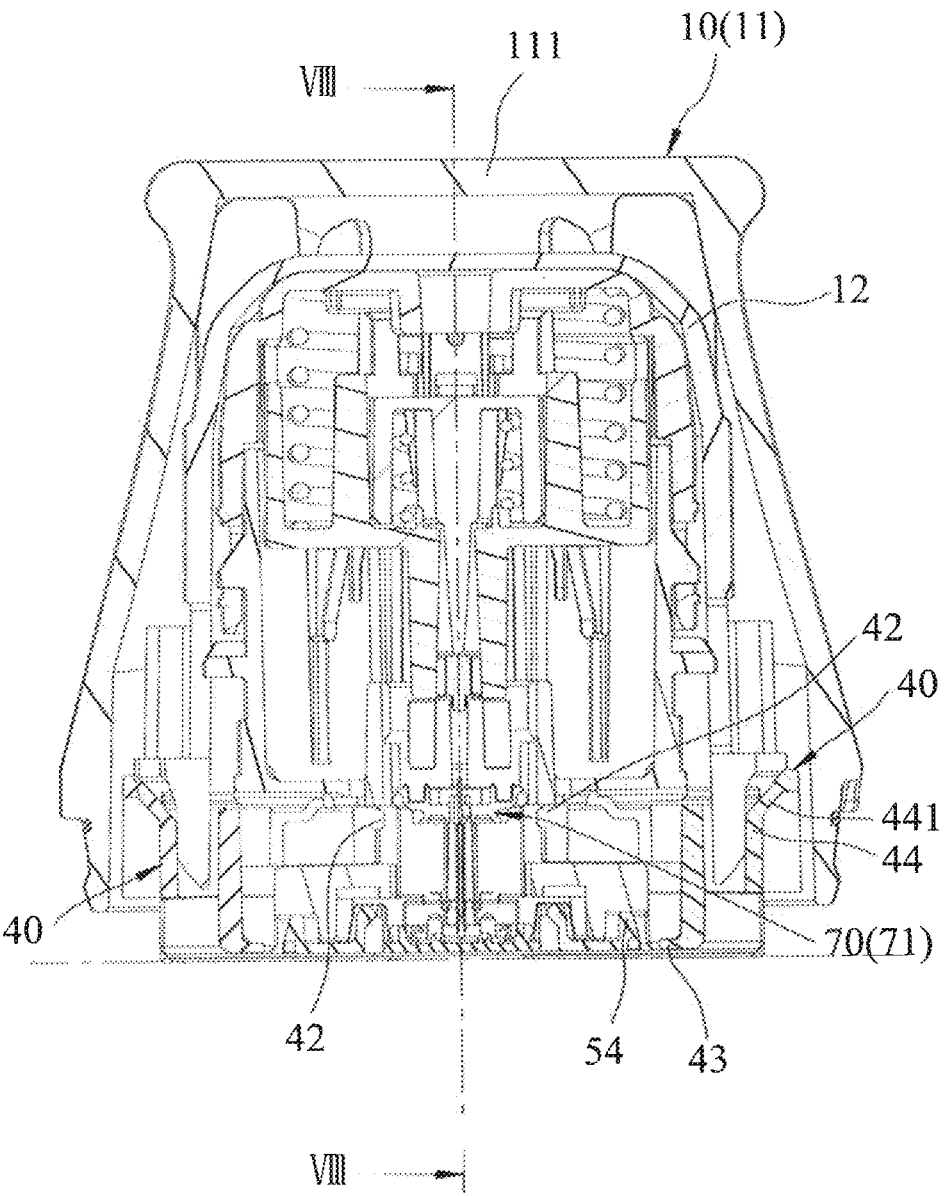
FIG. 7 is a schematic diagram of the embodiment shown in FIG. 1, illustrating that the bottom cover is removed and the implanting may occur in an instant while the needle has not been implanted into the subcutaneous portion.
Figure 8:
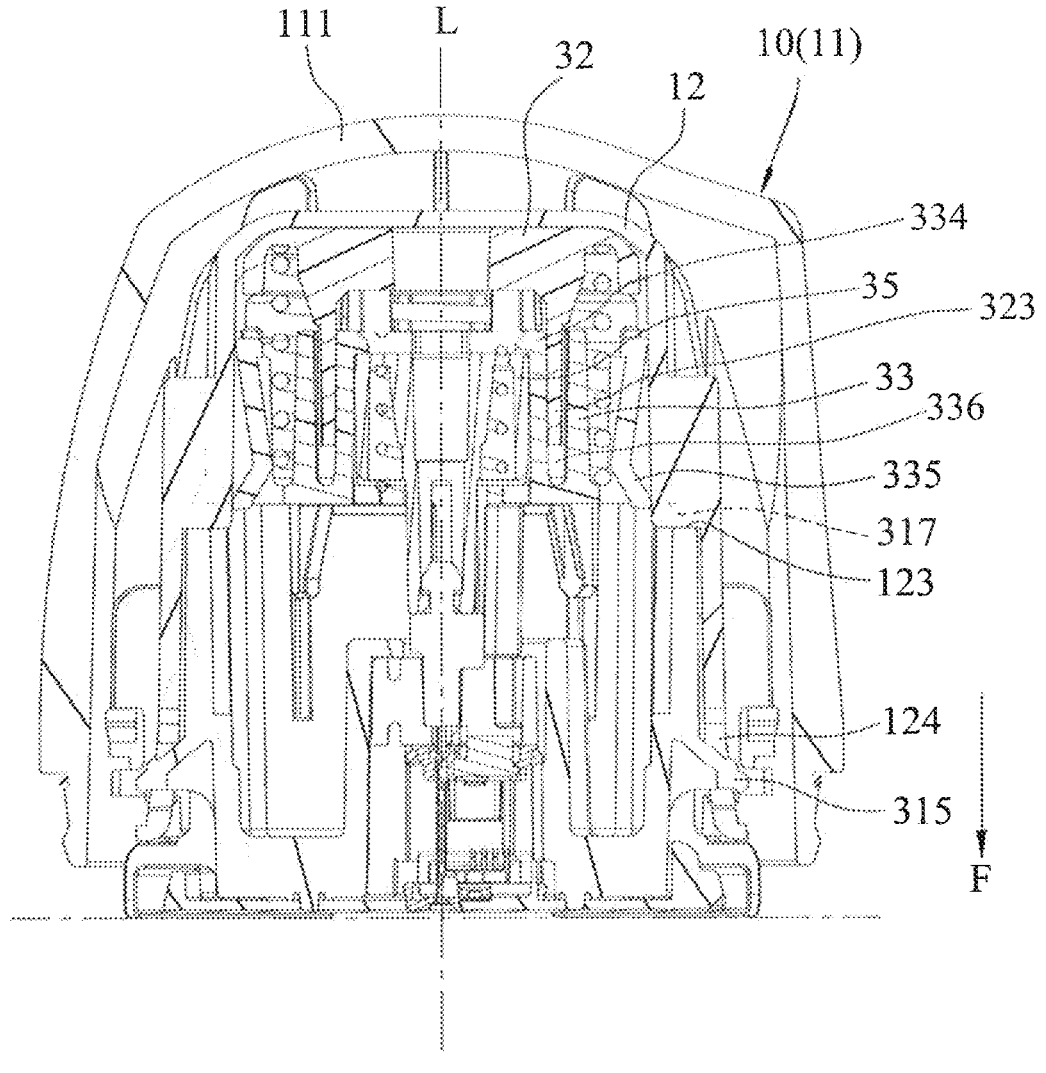
FIG. 8 is a sectional diagram taken along the line VIII-VIII of the embodiment illustrated in FIG. 7.

As shown in FIGS. 5-6, when the bottom cover 20 is removed or opened, and the desiccating container 100 is arranged on the skin surface of the biological body (shown by the dashed line in the horizontal direction), also referring to FIGS. 7-8, the housing 11 can be operated to move the lining piece 12 downward, that is, in the direction toward the skin surface. During the process, the actuating portions 123 of the lining piece 12 push the buckle portion 335 along its inclined surface to finally release the state of constraint between the stopping portion 317 and the buckle portions 335 and cause the first elastic element 34 in the implanting module 30 to automatically release a force to push the needle implanting seat 33 in the implantation direction F so as to implant the sensor 72 into subcutaneous of the living body. When the housing 11 is pressed downward by an external force, the bottom edge of the lining piece 12 will drive the guiding portion 44 of the fixing members 40, and the fixing members 40 will simultaneously move away from the axis L and render the support portions 42 away from the support of the sensor base 71, so that the first hooks 43 are also separated from the second hooks 54 respectively. The use of the guide slanting surfaces 441 can make the movement of the lining piece 12 driving the fixing members 40 quite smooth.

Figure 9:
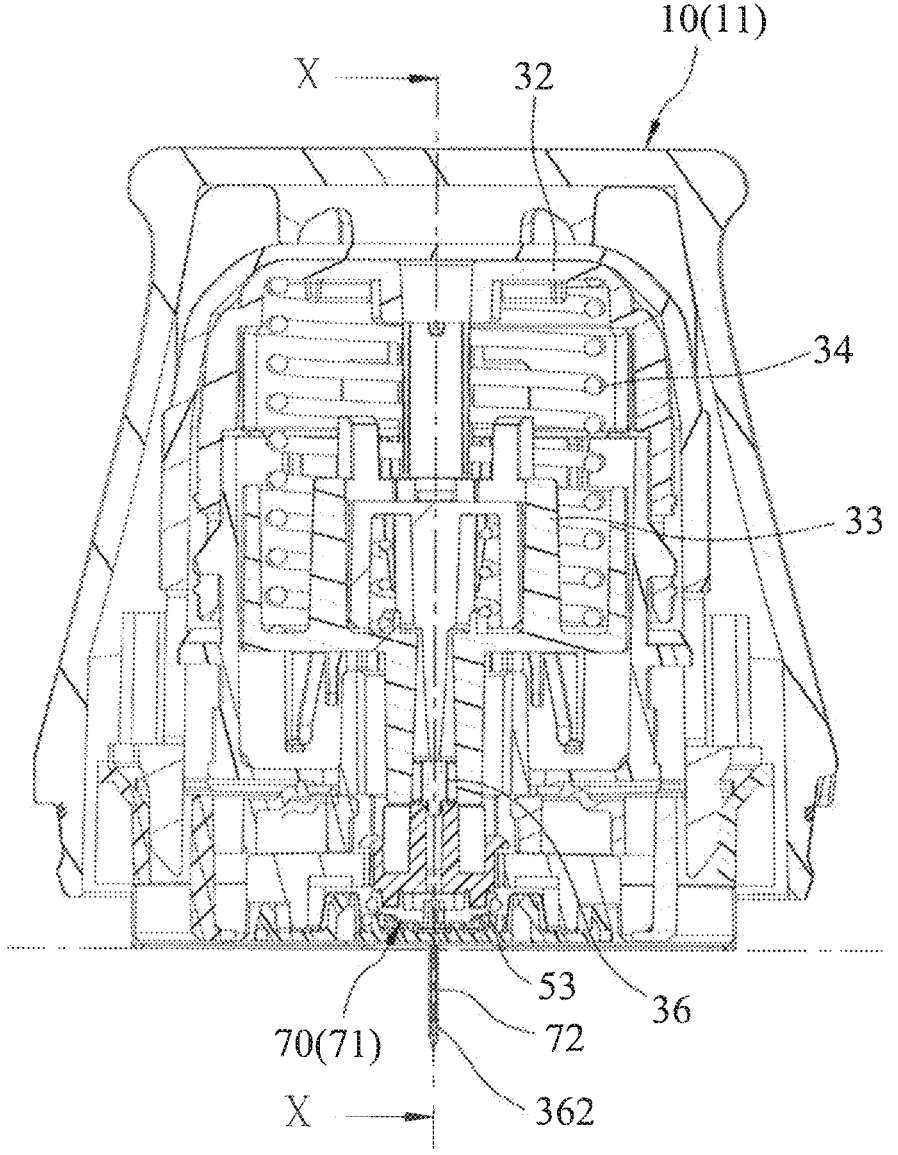
FIG. 9 is a schematic diagram of the embodiment shown in FIG. 1, illustrating that the container is at the stage right after the implanting.
Figure 10:
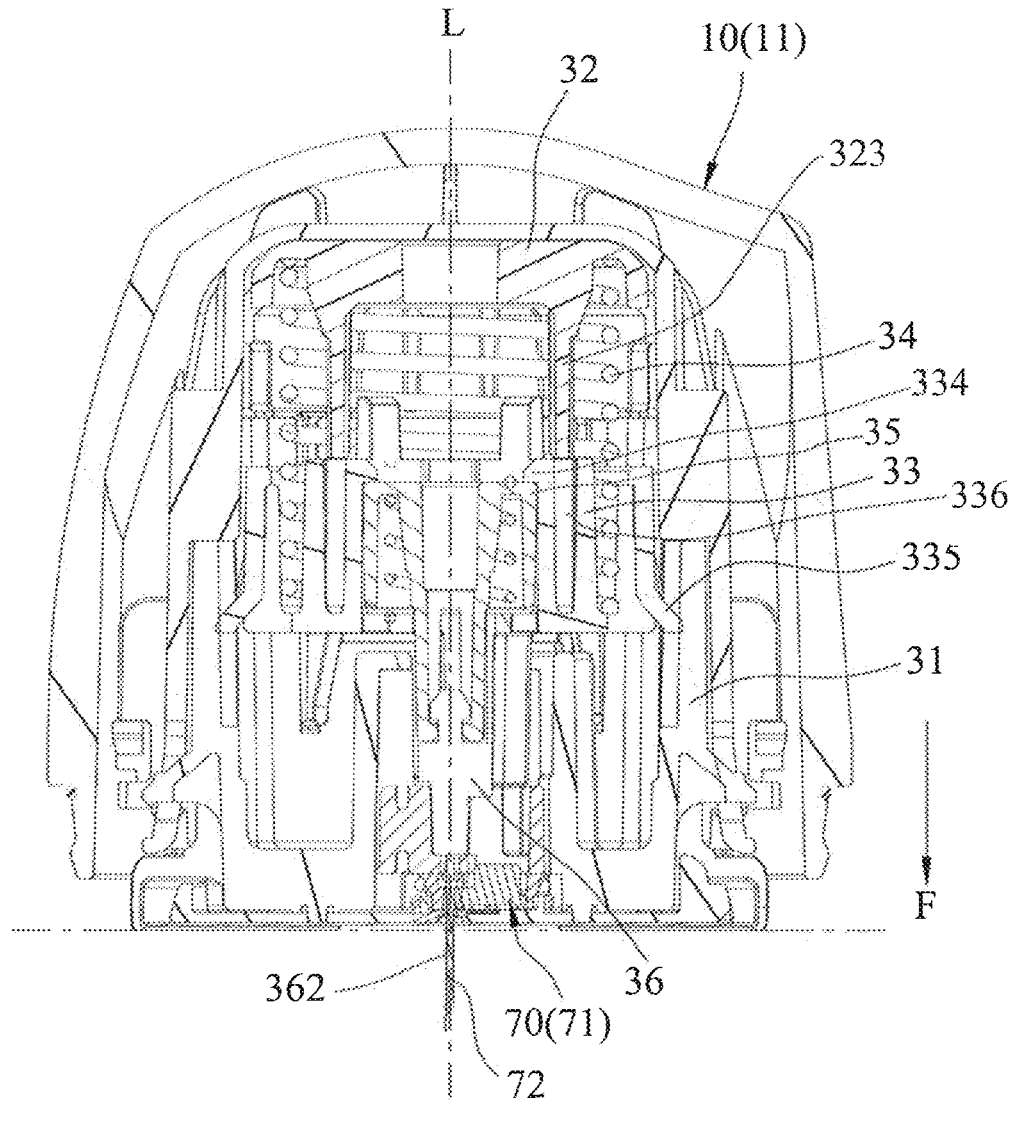
FIG. 10 is a sectional diagram taken along the line X-X of the embodiment illustrated in FIG. 9.

During the implantation process, when the housing 11 is operated to drive the lining piece 12 downward, the distance D between the main cover 32 and the lining piece 12 disappears, and only the actuating portions 123 on the inner peripheral surface 122 of the lining piece 12 slide along the slope of the buckle portion 335, and the external force applied to the housing 11 is not transmitted to the main body 31 down below, so the implanted living body does not feel the external force. And the restoring force of first elastic member (34) is configured not to act cover body (12) during the depression of said cover body (12). After the lining piece 12 being pressed by the user, the actuating portions 123 will be stuck underneath the main body 31, and thus the lining piece 12 cannot be moved upward while the user does not feel any vibration nor noise. As shown in FIGS. 7-8, at this moment, the constraint member 323 of the main cover 32 and the limiting groove 336 of the needle implanting seat 33 are still in a constraint state, and the needle-extracting constraint structure has not been released. As shown in FIGS. 8-10, after the bottom cover 20 is removed or opened and during the implantation process, the lower mount base 50 is separated from the sensor assembly 70, and when the detachable module received the force released by the implanting module 30, the detachment module is activated to detach from the implantation module, so that the sensor assembly 70 is assembled to the lower mount base 50 and the sensor 72 is implanted under the skin of the living body.

Figure 36:
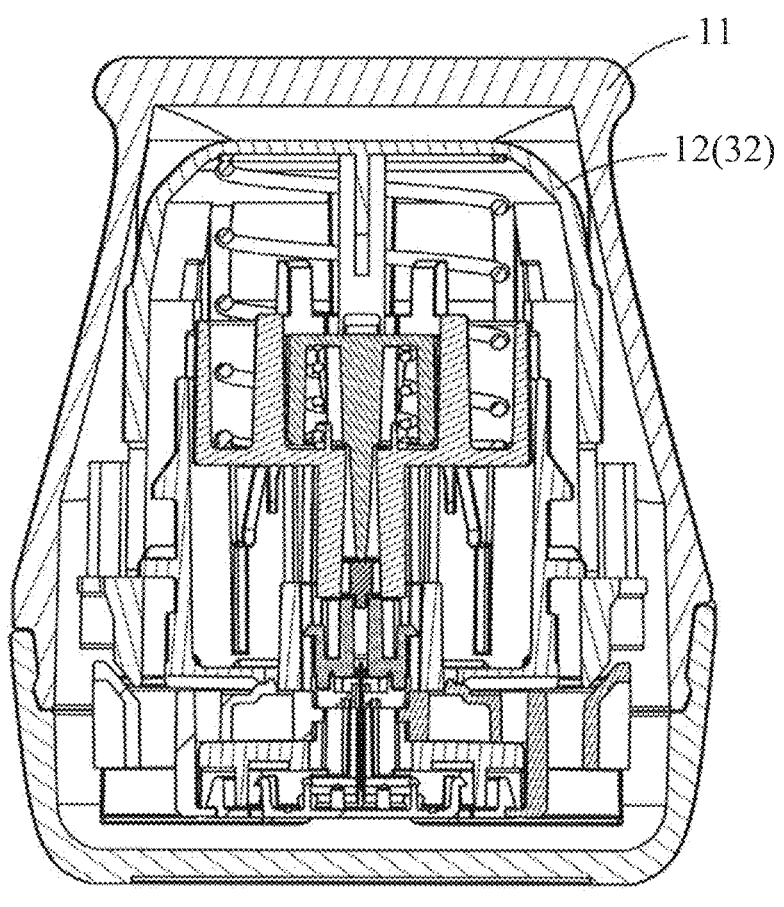
FIG. 36 is a schematic sectional view taken along the x-x direction of one of the embodiments shown in FIG. 2B.
Figure 37:
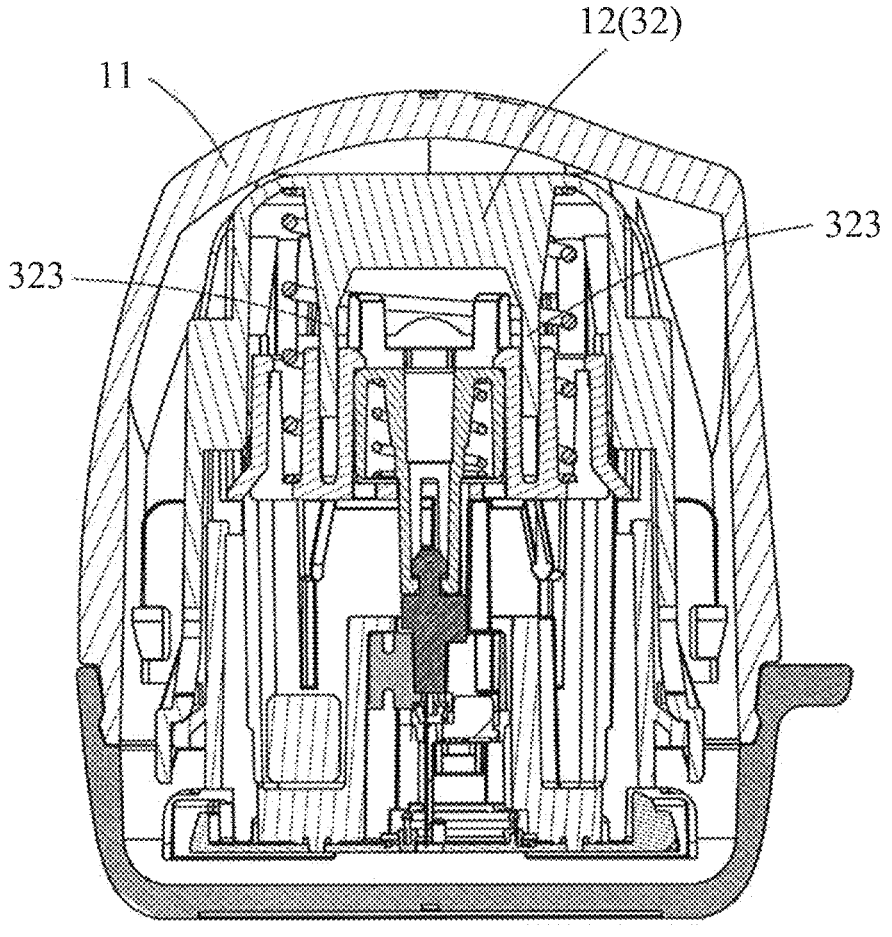
FIG. 37 is a schematic sectional view taken along the y-y direction of one of the embodiments shown in FIG. 2B.

In the embodiments shown in FIGS. 3-10, the main cover 32 in the implanting module 30 is an individual component. Those skilled in the art can combine the devices according to the drawings. For example, according to different embodiments, as shown in FIGS. 36-37, the operation processes of the automatic needle implantation and automatic needle extraction are similar to those of the previous embodiment, and the lining piece 12 can be designed to have the function of the main cover 32, therefore the main cover 32 doesn't need to be held as an individual component, and the main body member 31 and the lining piece 12 are connected to each other. The implanting module 30 includes a main body member 31 connected to the lining piece 12, and the main body member 31 and the lining piece 12 constitutes a displacement space 301.

The main body 31 has a pair of latching portions 315 which can be engaged with each of the locking portions 124 respectively, a needle implanting seat 33 that can detachably form a constraint relative to the lining piece 12 and movable in the displacement space 301 between the main body 31 and the lining piece 12, a first elastic element 34 which is a pre-compressed spring disposed against the needle implanting seat 33 and the lining piece 12 therebetween, a needle extracting seat 35 which is capable of maintaining a constraint relative to the needle implanting seat 33 and a second elastic element 37 which is pre-compressed between the needle implanting seat 33 and the needle extracting seat 35. The inner peripheral surface of the lining piece 12 has at least one actuating portion 123, and the needle implanting seat 33 has a buckle portion 335 which can be driven by the actuating portion 123 and is detachably disposed in the main body 31. By way of the buckle portion 335 of the needle implanting seat 33 resisting the stopping portion 317 of the main body 31, a triggering constraint structure is formed between the needle extracting seat 33 and the main body 31.

Figure 34:
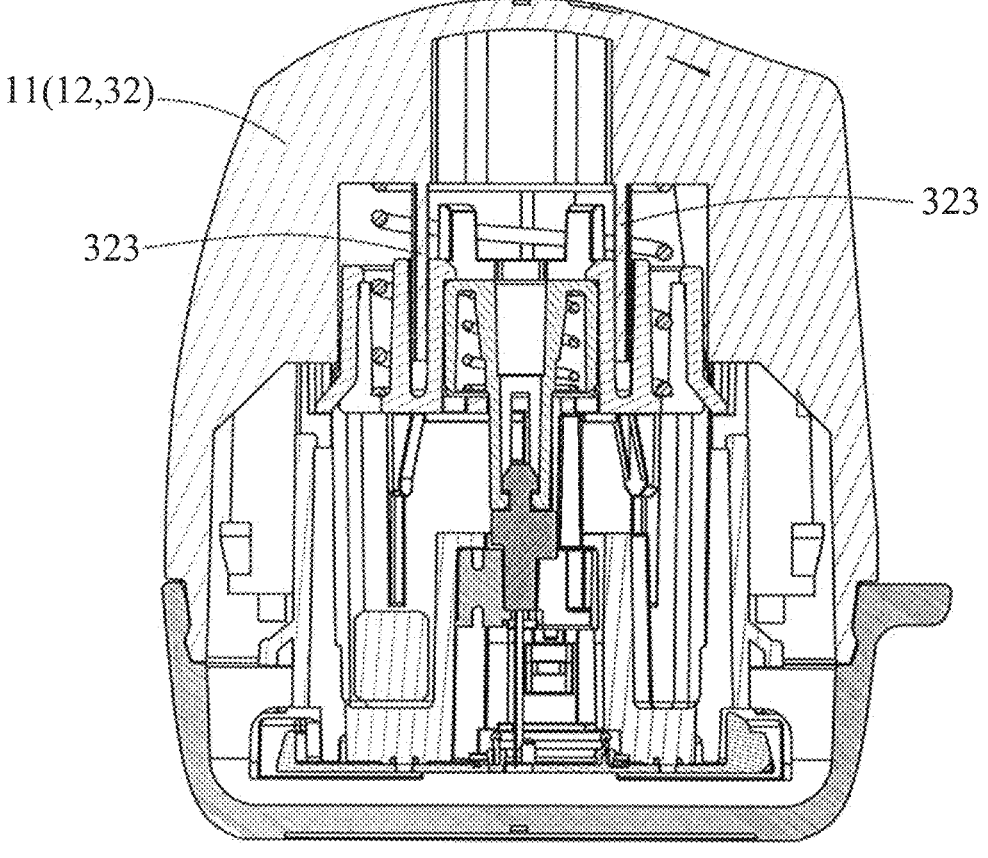
FIG. 34 is a schematic sectional view taken along the x-x direction of one of the embodiments shown in FIG. 2B.
Figure 35:
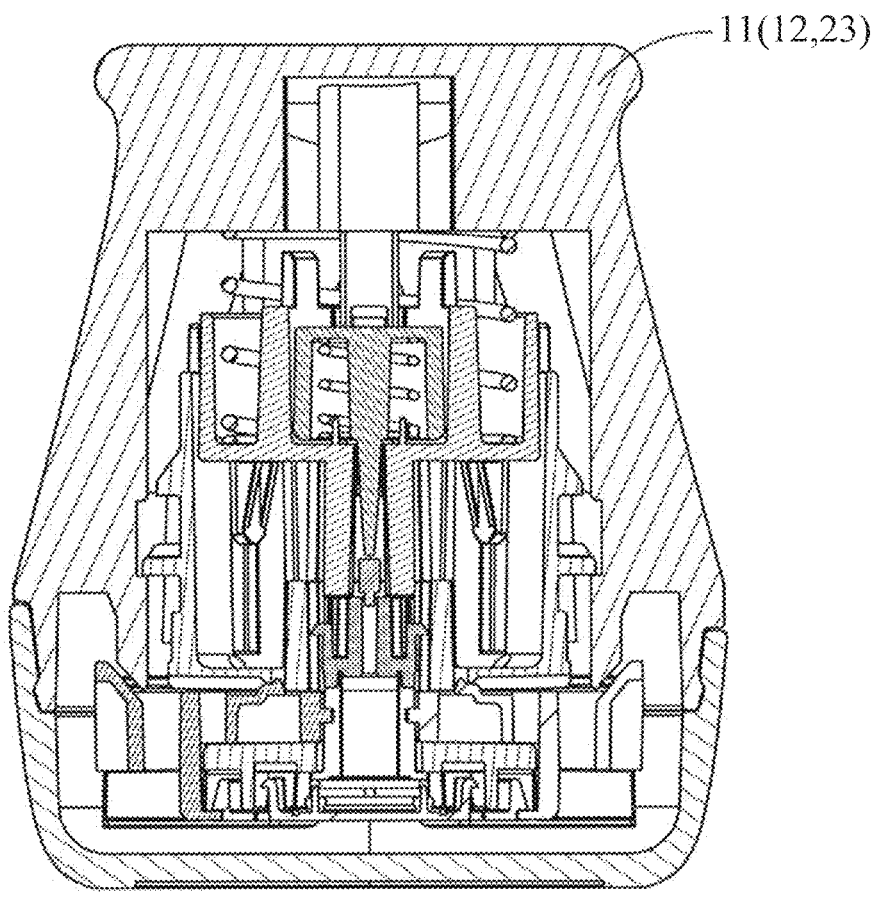
FIG. 35 is a schematic sectional view taken along the y-y direction of one of the embodiments shown in FIG. 2B.

In another embodiment, as shown in FIGS. 34-35, even the separate lining piece 12 and the main cover 32 may not be needed, since the housing 11 has the technical features including the lining piece 12 and the main cover 32. The implanting module includes: a main body 31 coupled to the housing 11 and forming a displacement space 301 with the housing 11, a needle implanting seat 33 that can detachably form a constraint relative to the housing 11 and movable in the displacement space 301 between the main body 31 and the housing 11, a first elastic element 34 which is a pre-compressed spring disposed against the needle implanting seat 33 and the housing 11 therebetween, a needle extracting seat 35 which is capable of maintaining a constraint relative to the needle implanting seat 33 and a second elastic element 37 which is pre-compressed between the needle implanting seat 33 and the needle extracting seat 35.

In another embodiment, as shown in FIGS. 32-33, the housing 11 and the lining piece 12 are integrally formed to constitute a casing assembly 10. The implanting module includes 31: a main body 31 coupled to the casing assembly 10 and forming a displacement space 301 with the casing assembly 10, a needle implanting seat 33 that can detachably form a constraint relative to the casing assembly 10 and movable in the displacement space 301 between the main body 31 and the casing assembly 10, a first elastic element 34 which is a pre-compressed spring disposed against the needle implanting seat 33 and the casing assembly 10 therebetween, a needle extracting seat 35 which is capable of maintaining a constraint relative to the needle implanting seat 33 and a second elastic element 37 which is pre-compressed between the needle implanting seat 33 and the needle extracting seat 35.

Referring to FIGS. 9-10, when the first elastic element 34 in the implanting module 30 releases the force, the needle implanting seat 33 is pushed away from the main cover 32, and the constraint of the constraint elements 323 of the main cover 32 in the limiting groove 336 of the needle implanting seat 33 is automatically released. At this moment, while the housing 11 is pressed down, the needle extracting seat 35 maintains at a position relative to the needle implanting seat 33 due to the limiting element 334.

Figure 11:
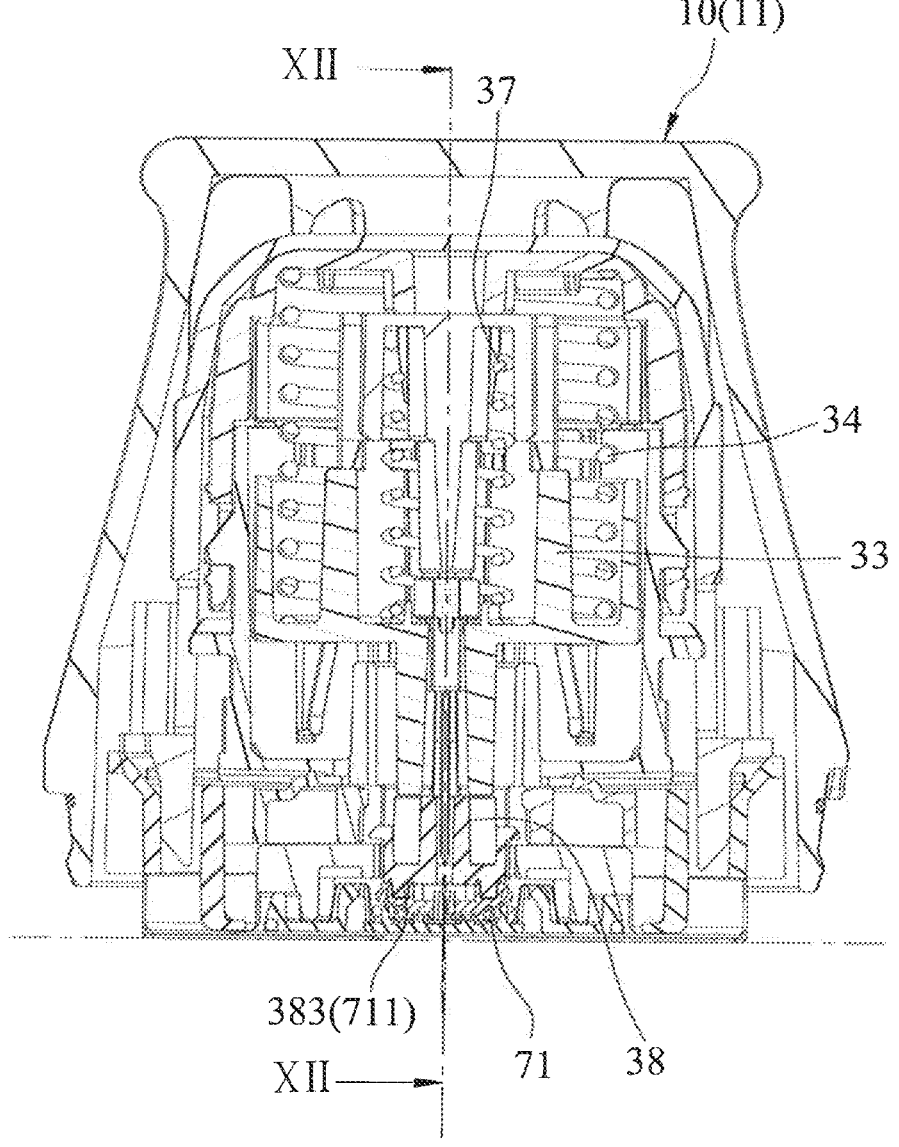
FIG. 11 is a schematic diagram of the embodiment shown in FIG. 1, illustrating the stage of needle extraction after the implanting.
Figure 12:
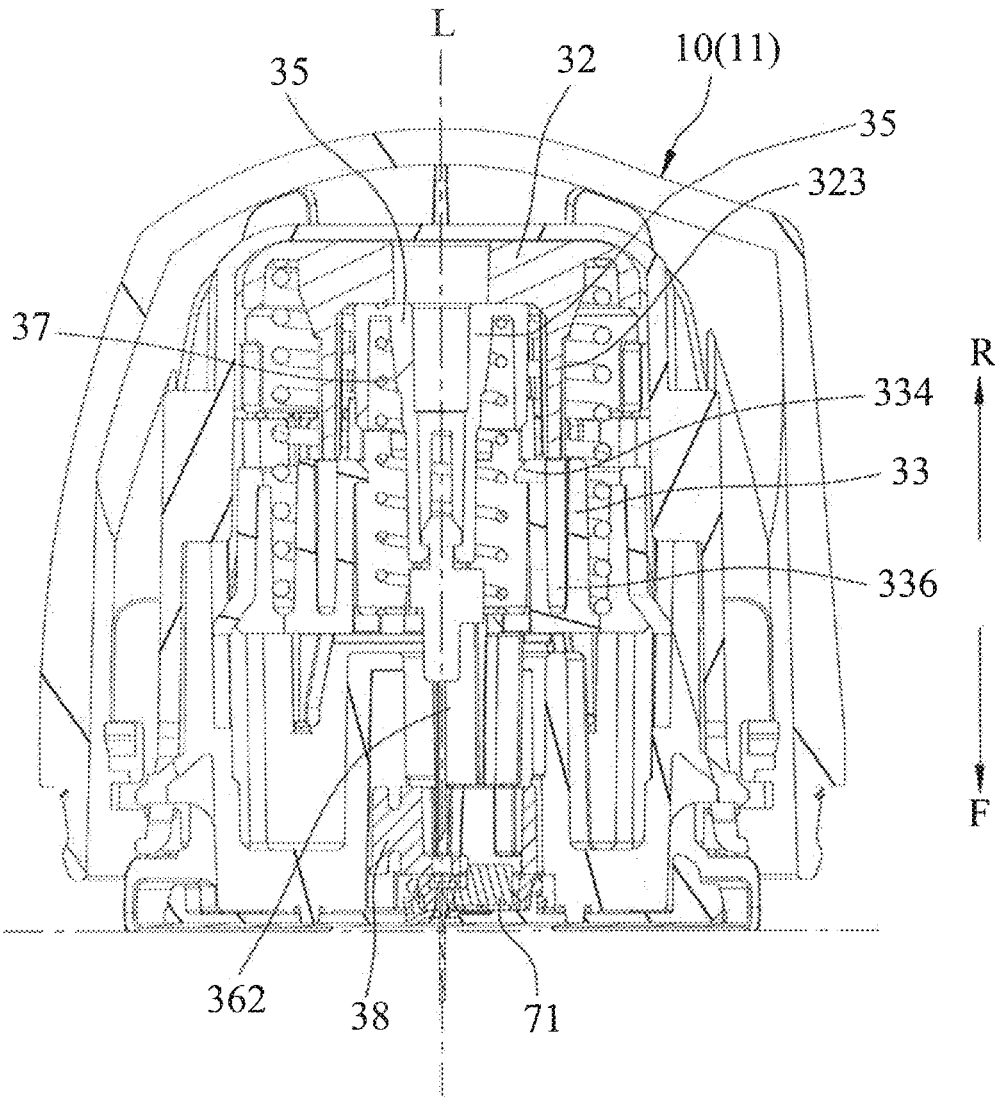
FIG. 12 is a sectional diagram taken along the line XII-XII of the embodiment illustrated in FIG. 11.

Referring to FIGS. 11-12, because of the detachment of the constraint element 323, the limiting element 334 that initially held the needle extracting seat 35 at the position relative to the needle implanting seat 33 can no longer keep itself in the initially position and deviates in the direction of the limiting groove 336, so that the needle extracting seat 35 is released from the restriction of the needle implanting seat 33 and the constraint on the movement of the needle extracting seat 35 in the withdrawal direction R is released. Therefore, the second elastic element 37 spring-loaded between the needle implanting seat 33 and the needle extracting seat 35 may release its elastic force and make the needle extracting seat 35 moving in the needle extraction direction R at this moment, so that the needle 362 which has just completed the implantation procedure can be withdrawn immediately to complete continuous implanting and extracting operation.

The first and second elastic elements 34, 37 can be made of helical springs or pneumatic/pneumatic elements for examples. Because the needle implantation and needle extraction are completed through the instantaneous elasticity release of the two pre-compressed elastic elements 34, 37, the present invention of implanting a sensor from an implantation device stored in container into a subcutaneous by using an automatic mechanism can complete the needle implantation and needle extraction operation in a very short time, which does not make the implanted person feel uncomfortable, even the living body have yet a painful feeling when finishing the implantation process. The user does not feel the reaction force of the first elastic element 34 when pressing the housing 11, thus the smoothness of the automatic needle implantation and withdrawal process is improved, and the time for completing the automatic needle implantation and the automatic needle withdrawal operation is no more than 100 milliseconds (ms), or no more than 50 ms, or no more than 8 ms, 6 ms, 4 ms or even 2 ms.

Figure 13:
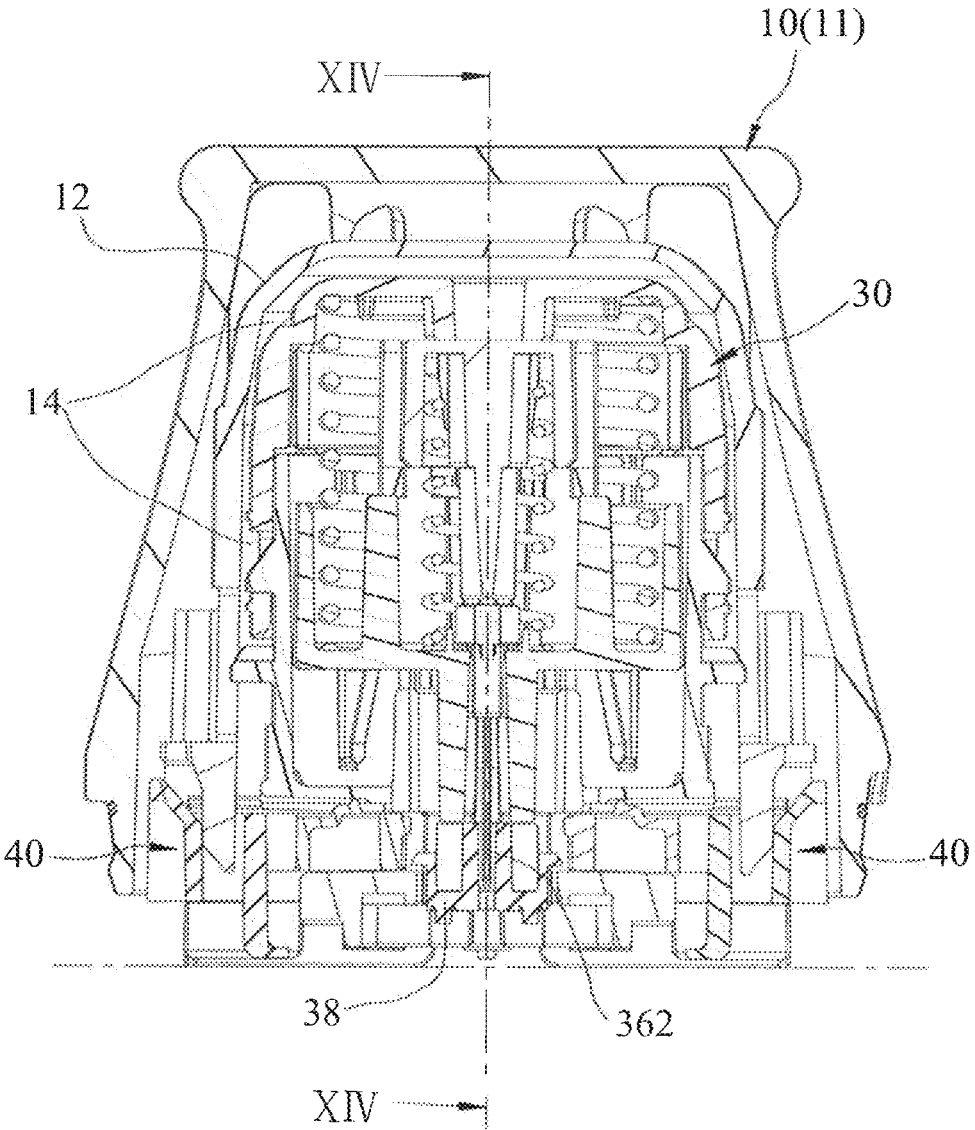
FIG. 13 is a schematic diagram of the embodiment shown in FIG. 1, illustrating the stage when the implanting is completed.
Figure 14:
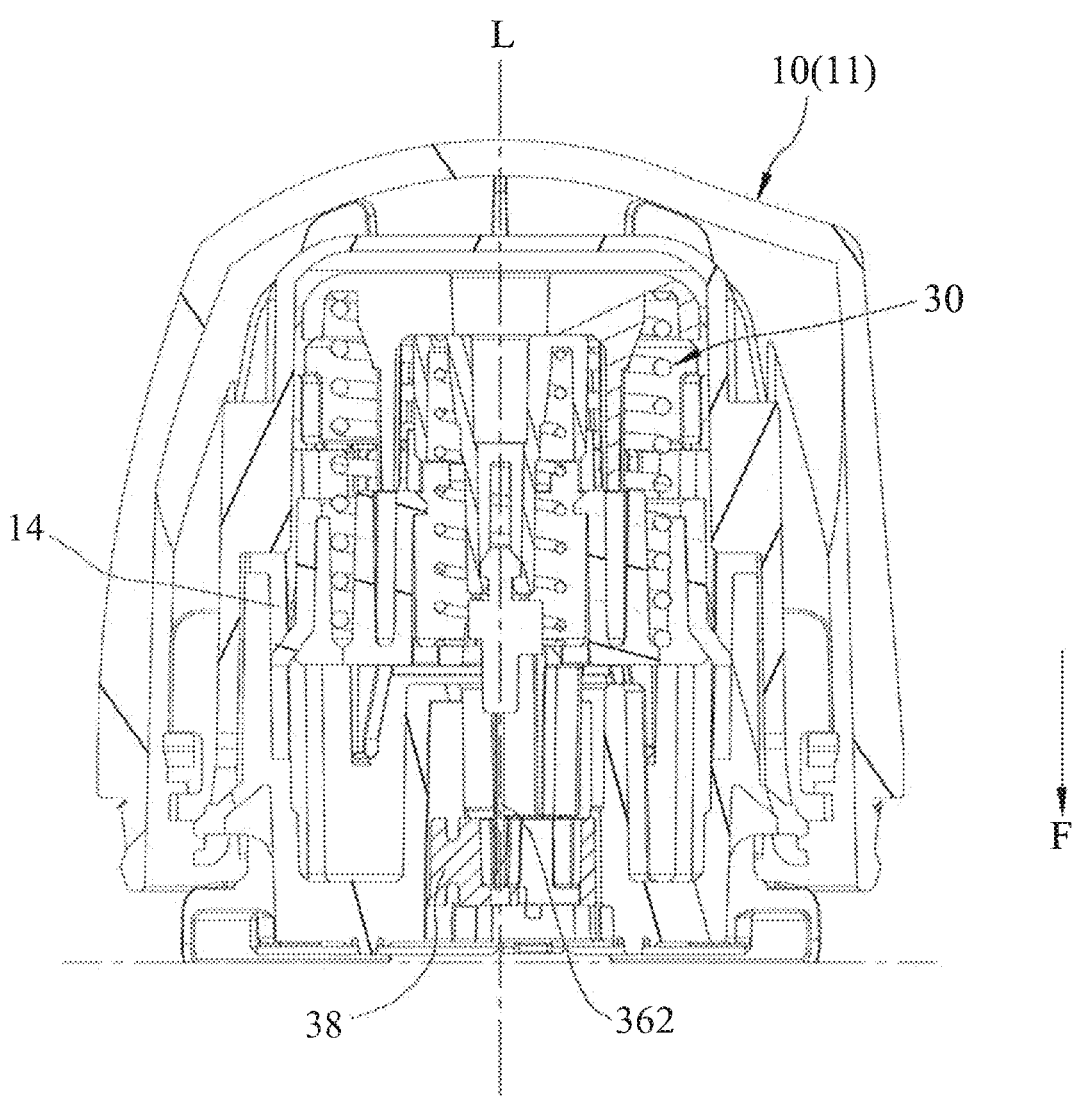
FIG. 14 is a sectional diagram taken along the line XIV-XIV of the embodiment illustrated in FIG. 11.

In addition, according to the present invention, after the external force is applied to the top wall 111 of the housing 11, the actions such as unlocking, implanting the needle and extracting the needle can be continuously completed. During the operation, the user can complete the implantation without releasing hand from the housing 11, the implanting device is functioned by means of elastic needle implantation, rather than relying on the user's hand to press it down. Therefore, the implantation device of the present invention can effectively solve the problem that the conventional method will affect the smoothness of the implantation and needle extraction due to the user's operation poor proficiency. FIGS. 13-14 show that the needle 362 is completely withdrawn back into the accommodating space 14 of the lining piece 12 after the needle extraction process, and more clearly inside the auxiliary implantation seat 38 to prevent the sharp needle 362 from being exposed outside the bottom opening to cause an accident.

Figure 15:
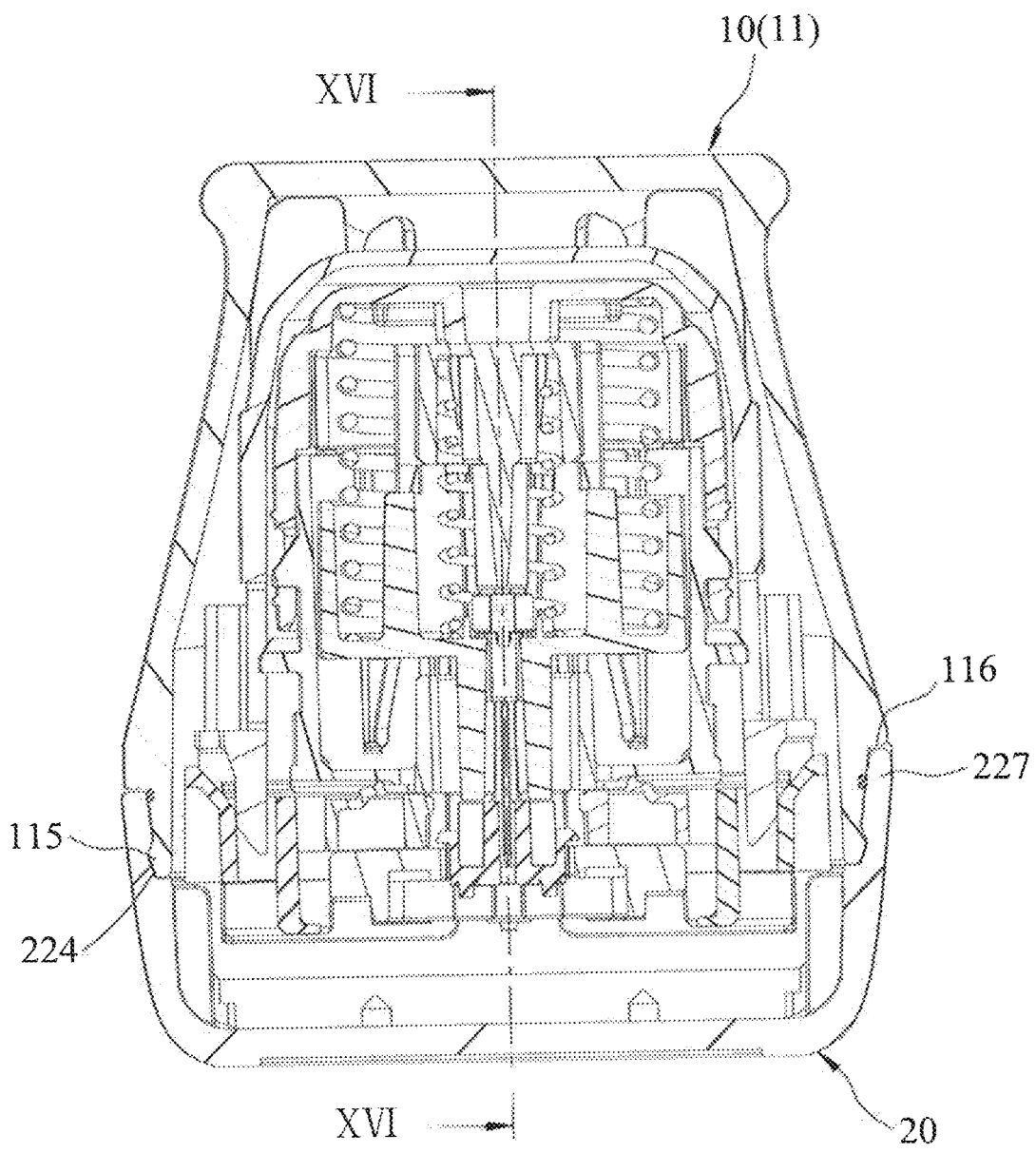
FIG. 15 is a schematic diagram of the embodiment shown in FIG. 1, illustrating that the bottom is restored.
Figure 16:
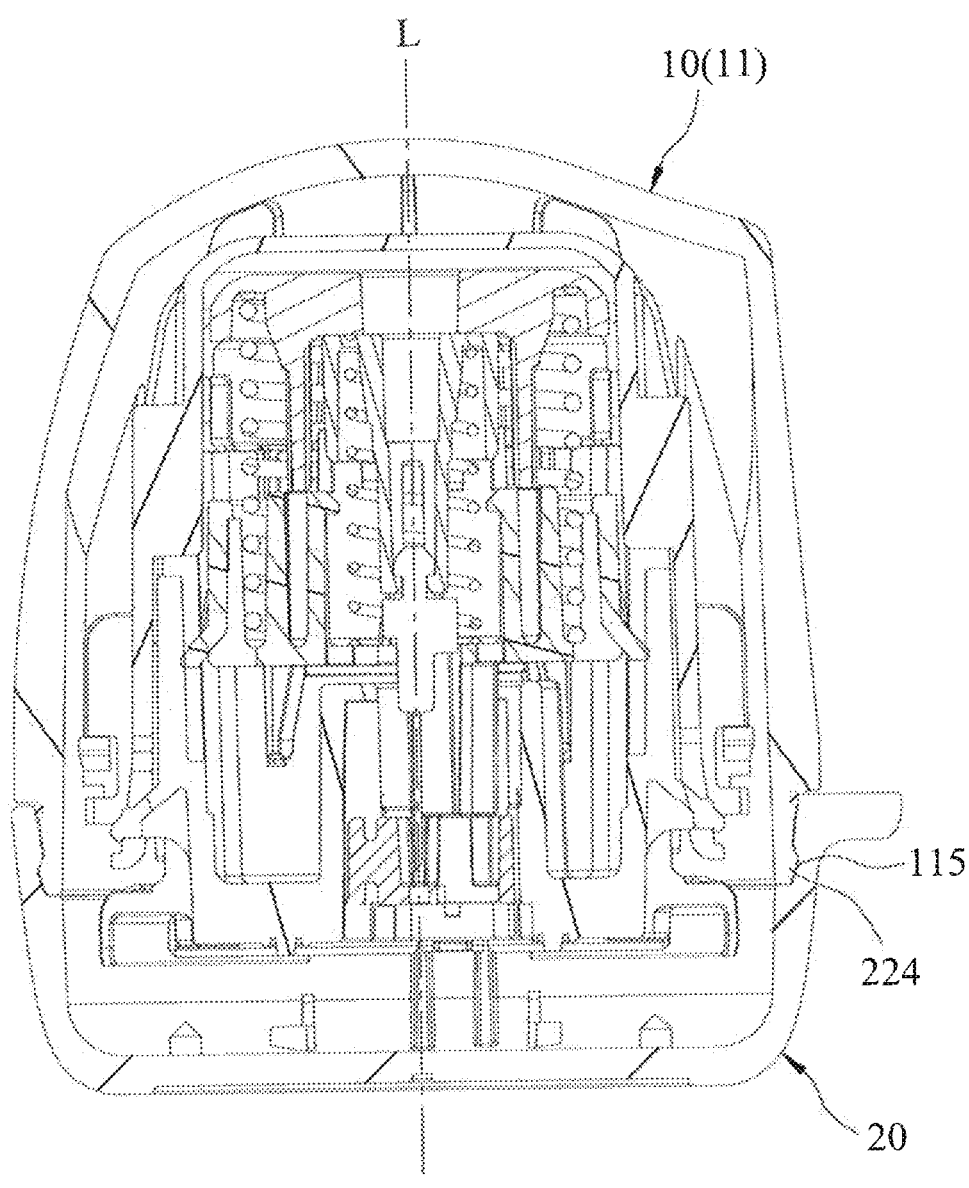
FIG. 16 is a sectional diagram taken along the line XVI-XVI of the embodiment illustrated in FIG. 15.

FIGS. 15-16 shows how the bottom cover 20 is re-coupled after use. After the implantation is completed, the user can easily combine the bottom cover 20 and the housing 11 with the aid of the positioning piece 227 on the bottom cover 20 and the matching portion 116 at the bottom opening of the housing 11 to achieve the purpose of accurate alignment and foolproof. In addition, the desiccating and airtight storage device 100 can be used as a waste storage means. The used lower base mount 50 can be detached and stored in the original desiccating and airtight storage device 100, allowing the user to discard in accordance with medical waste disposal requirement.

Figure 17:
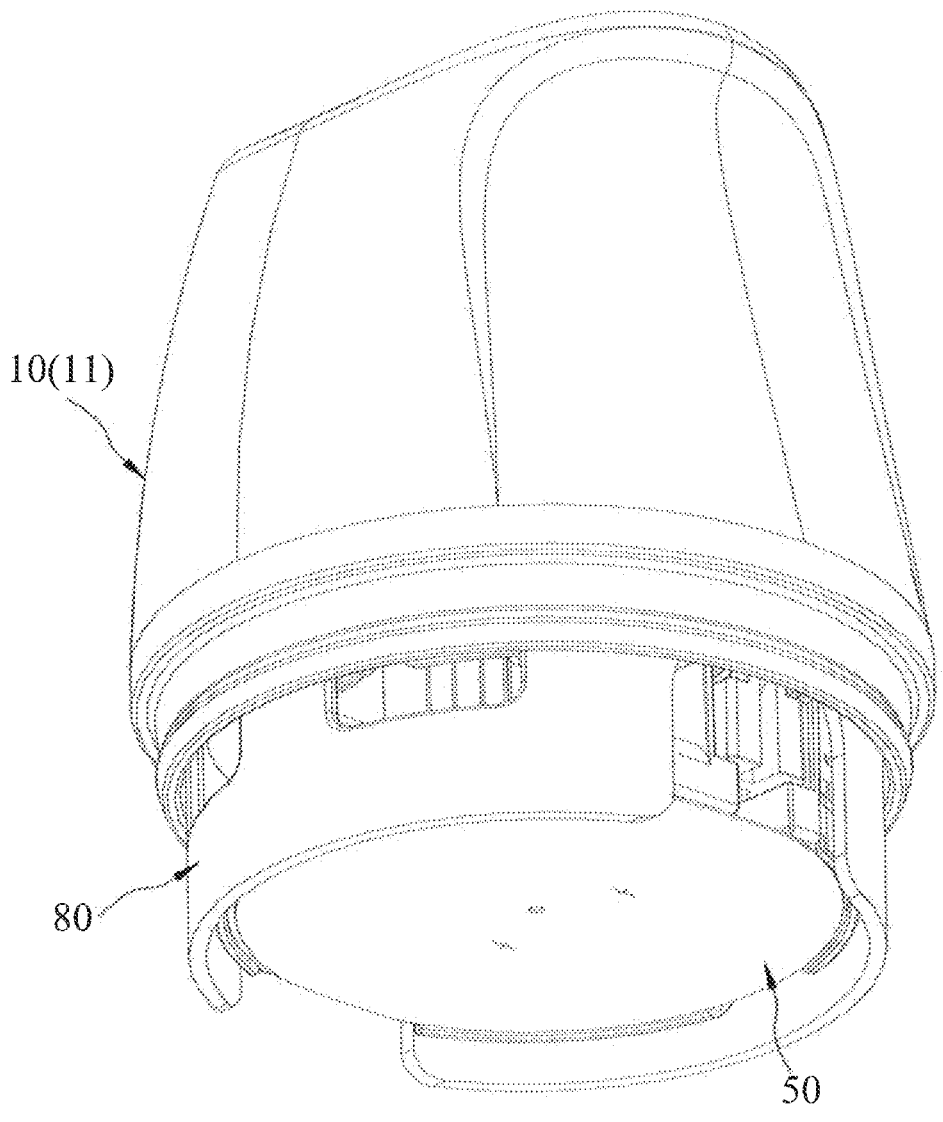
FIG. 17 is a partially assembled perspective view of another embodiment of the air-tight and desiccating container of the present invention.
Figure 18:
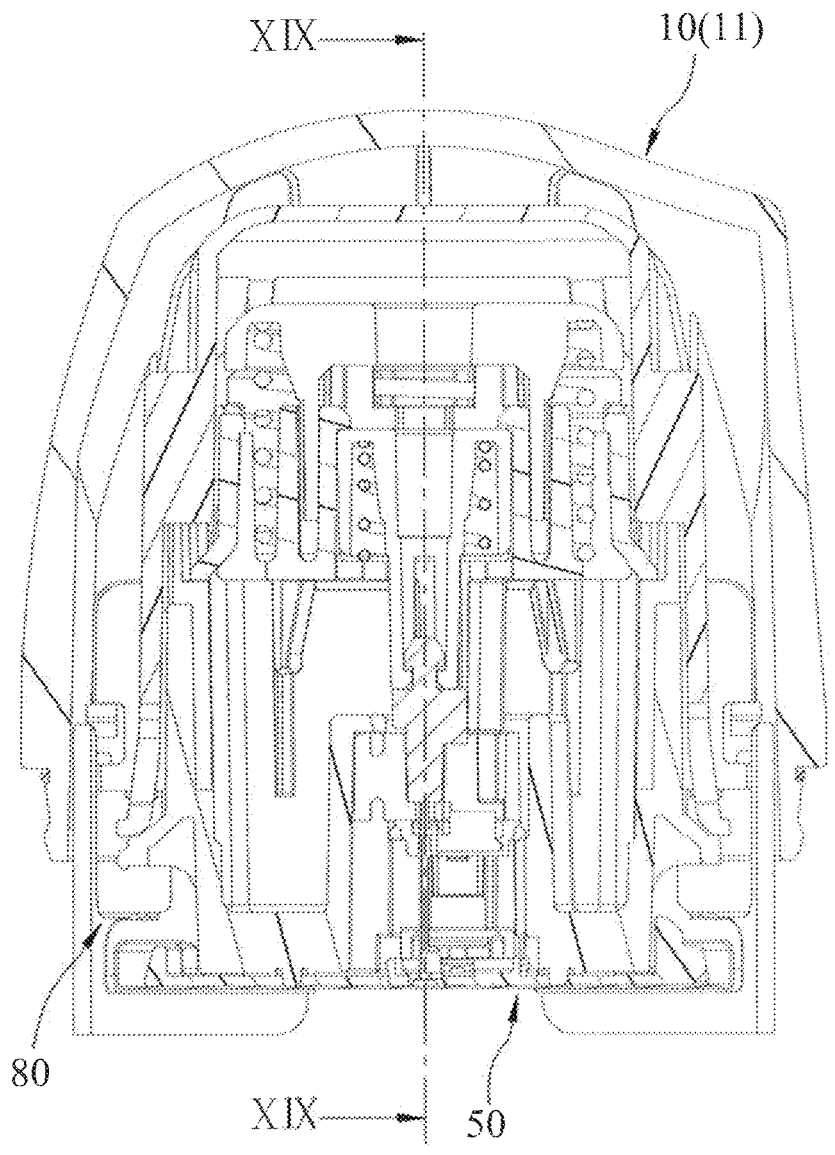
FIG. 18 is a schematic diagram of the embodiment shown in FIG. 17, illustrating the stage of being prepared for the implanting.
Figure 19:
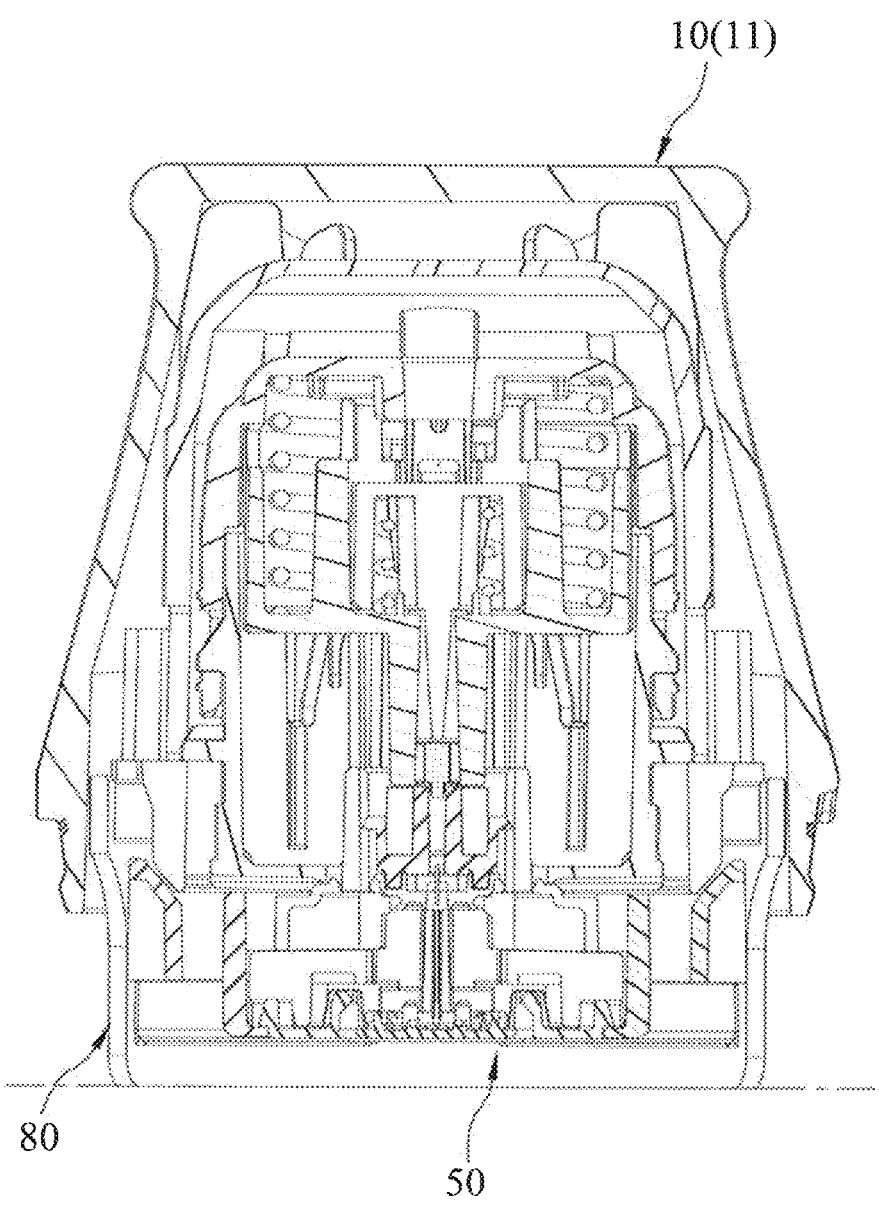
FIG. 19 is a sectional diagram taken along the line XIX-XIX of the embodiment illustrated in FIG. 18.
Figure 20:
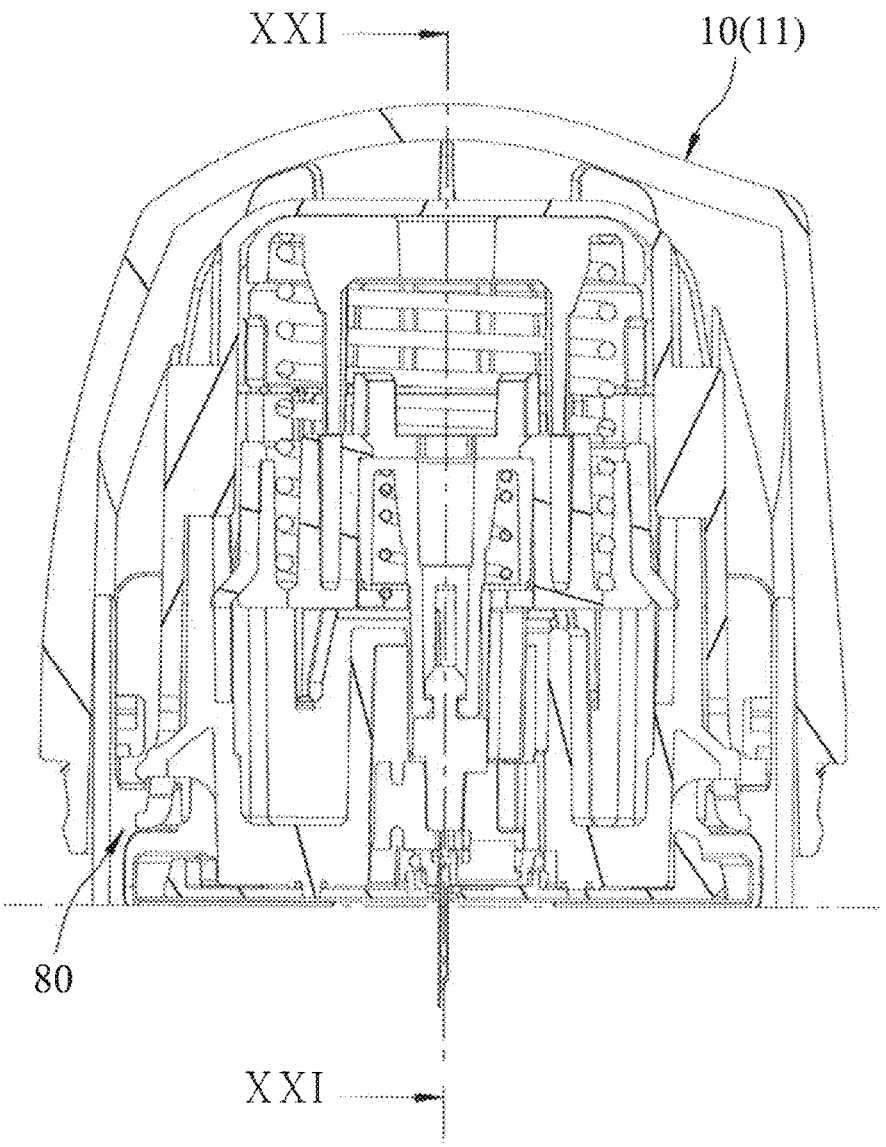
FIG. 20 is a schematic diagram of the embodiment shown in FIG. 17, illustrating an instance during the implanting.
Figure 21:
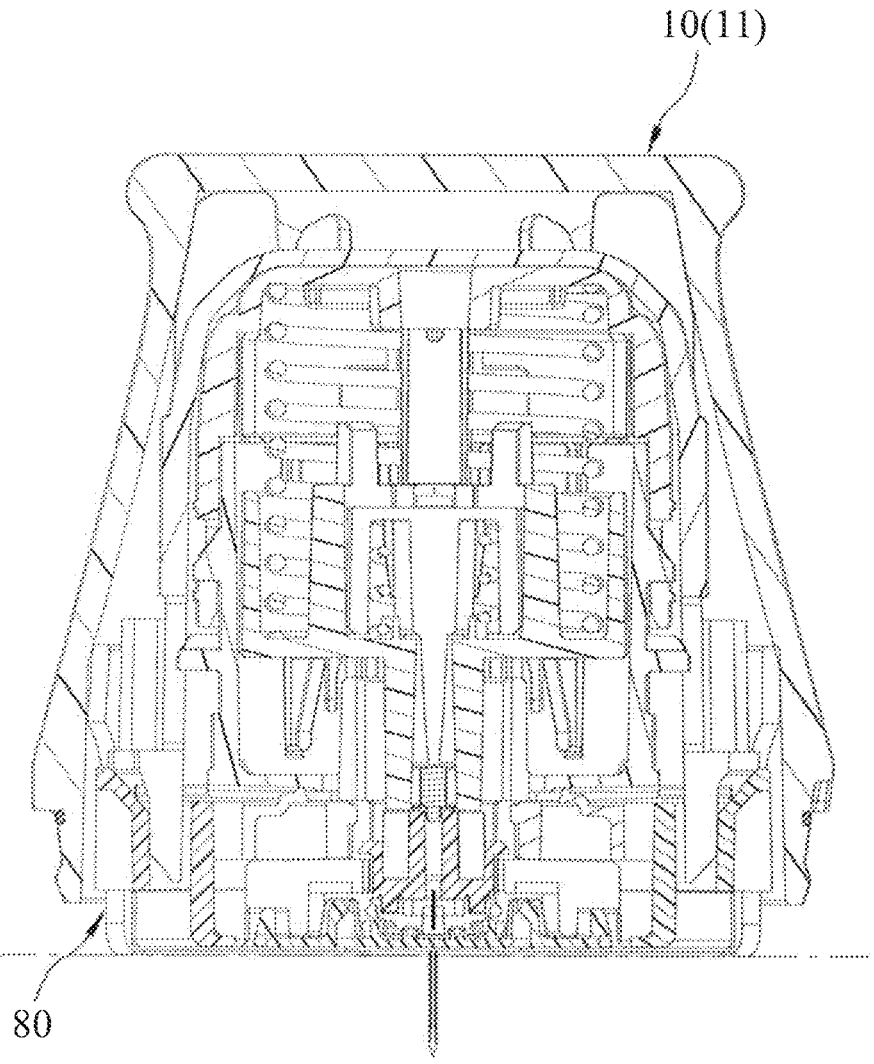
FIG. 21 is a sectional diagram taken along the line XXI-XXI of the embodiment illustrated in FIG. 20.

As shown in FIGS. 17-19, another embodiment of the desiccating and airtight container according to the present invention is different from the first embodiment in that a protective ring 80 is added thereon, and the protective ring 80 is sleeved on the bottom of the casing 11. The lower base mount 50 is disposed on the inner side of the bottom edge of the protective ring 80 before the implantation operation, so when the bottom edge of the protective ring 80 abuts against the skin surface of the living body, the lower base mount 50 will not contact the skin surface. The user can move the implantation device to the position to be implanted, then the triggering action of pressing down the casing assembly 10 (or the housing 11) is performed (as shown in FIGS. 20 and 21), and the housing is pressed down. After the implantation, the protective ring 80 can be retracted relative to the casing assembly 10 (or the housing 11) by applying a force, and the lower base mount 50 is then adhered to the skin surface. Therefore, with the aid of the protective ring 80 of this embodiment, it can be adjusted to the required skin position before the needle implantation operation is performed, which is quite convenient in use.

Figure 22:
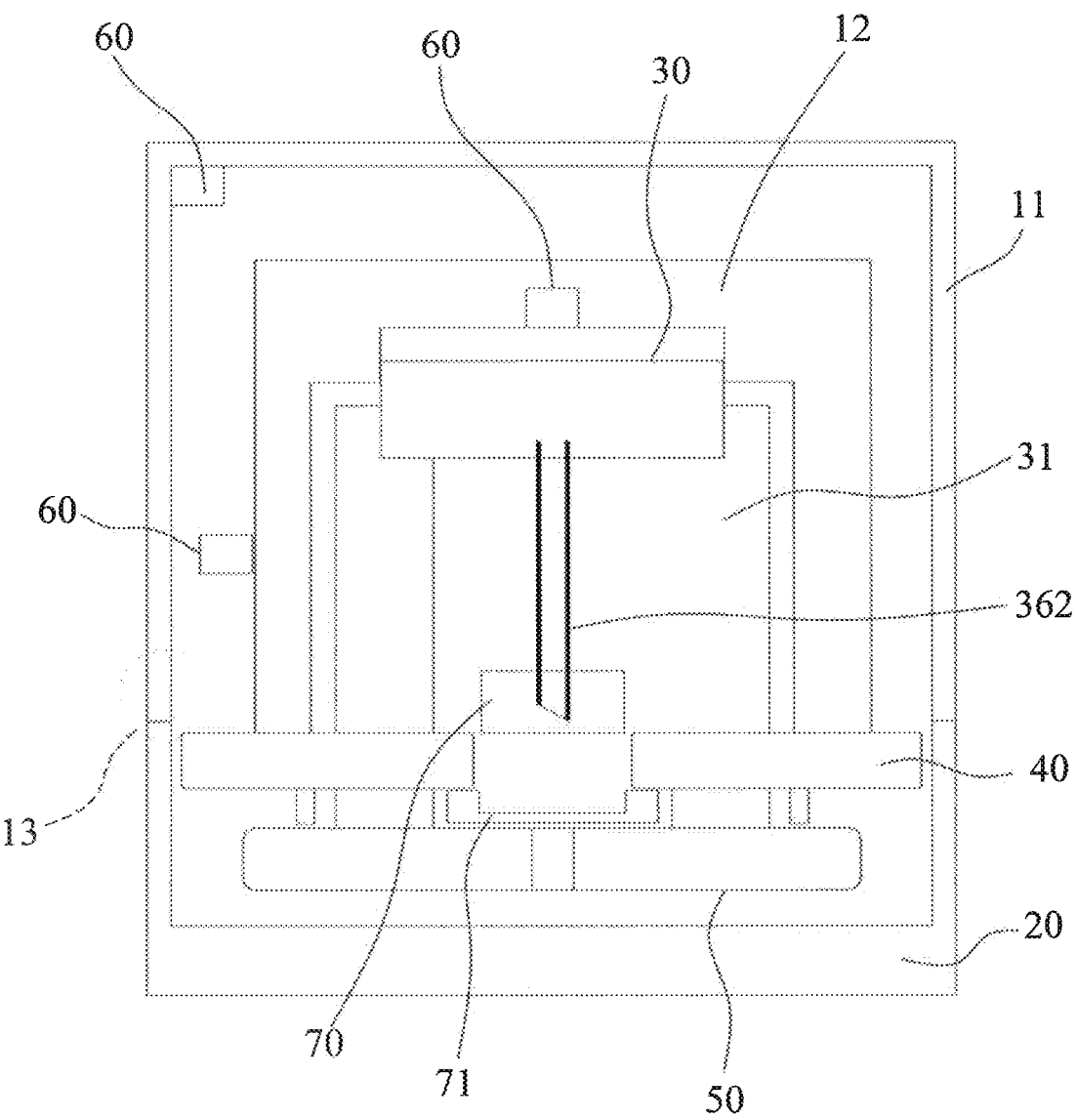
FIG. 22 is a schematic diagram showing the air-tight and desiccating container according to another embodiment of the present invention.
Figure 23:
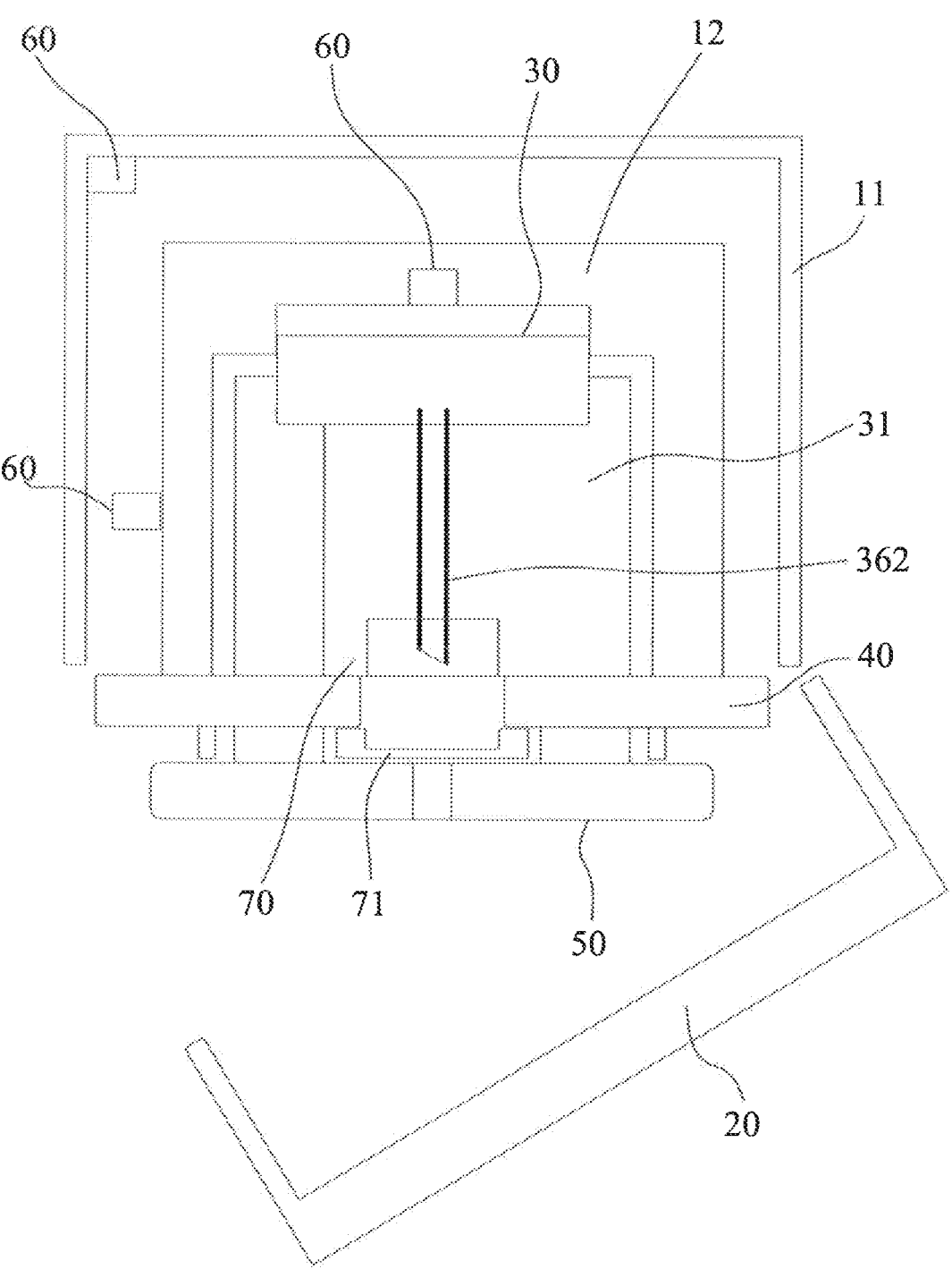
FIG. 23 is a schematic diagram of the embodiment shown in FIG. 17, illustrating that the bottom cover is removed and is at the stage of being prepared for the implanting.
Figure 24:
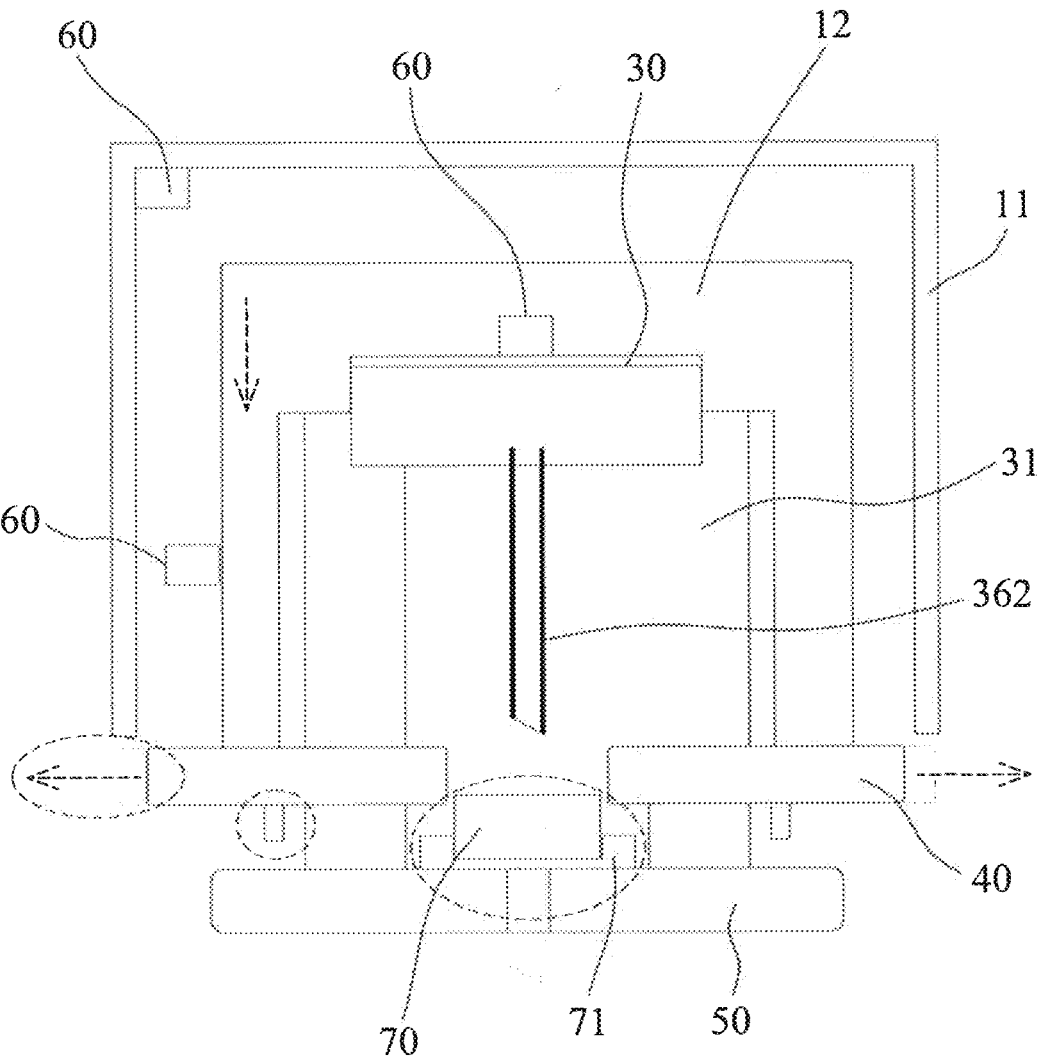
FIG. 24 is a schematic diagram of the embodiment shown in FIG. 17, illustrating the implanting operation.
Figure 25:
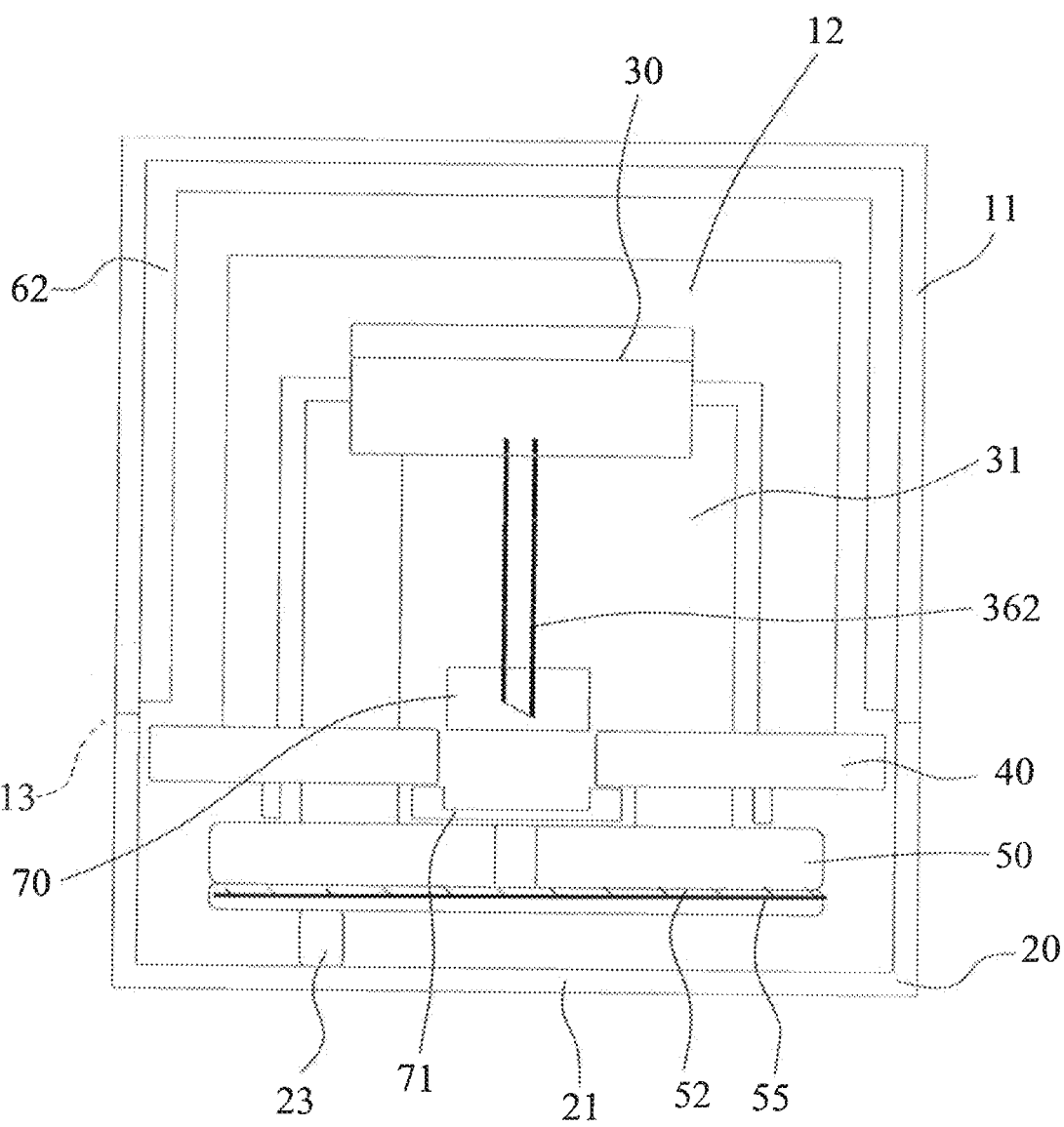
FIG. 25 is a schematic diagram of the embodiment shown in FIG. 17, illustrating the stage before removing the bottom cover.

Referring to FIGS. 22-26 (for the convenience of explanation, FIGS. 22-26 are only shown in simplified draws), the desiccating container 100 of the present invention, which integrates with the implantation device and the sensor, has a housing 11 and a bottom cover 20 jointly form an air-tight combination structure with an air-tight condition inside, and the desiccant 60 can be disposed at any appropriate position inside the desiccating container. In addition, in an embodiment, the desiccant is disposed on the inner peripheral surface of the housing 11 or the outer peripheral surface of the lining piece 12. At least one component related to the peripheral surfaces or the implanting module 30 is integrally formed with the desiccant 60, or configured with a containing space for he desiccant 60 to be placed (as shown in FIGS. 22 and 23), or the sensor assembly 70 has a desiccant 60 (not shown), or as shown in FIG. 25, a desiccant layer 62 is formed on the inner peripheral surface of the housing 11 or the bottom cover 20 or an accommodating space is arranged for the desiccant 60 to be placed (not shown), which keeps the inside of the desiccating container dry and prevent the sensor assembly 70 from getting wet, especially to prevent the chemical reagent 20 on the sensor 72 from deliquesced (as shown in FIG. 31) to ensure the detection accuracy of the sensor 72. The chemical reagent 720 comprises, for example, at least one analyte-responsive enzyme 726 and a polymer film layer 728.

Figure 26:
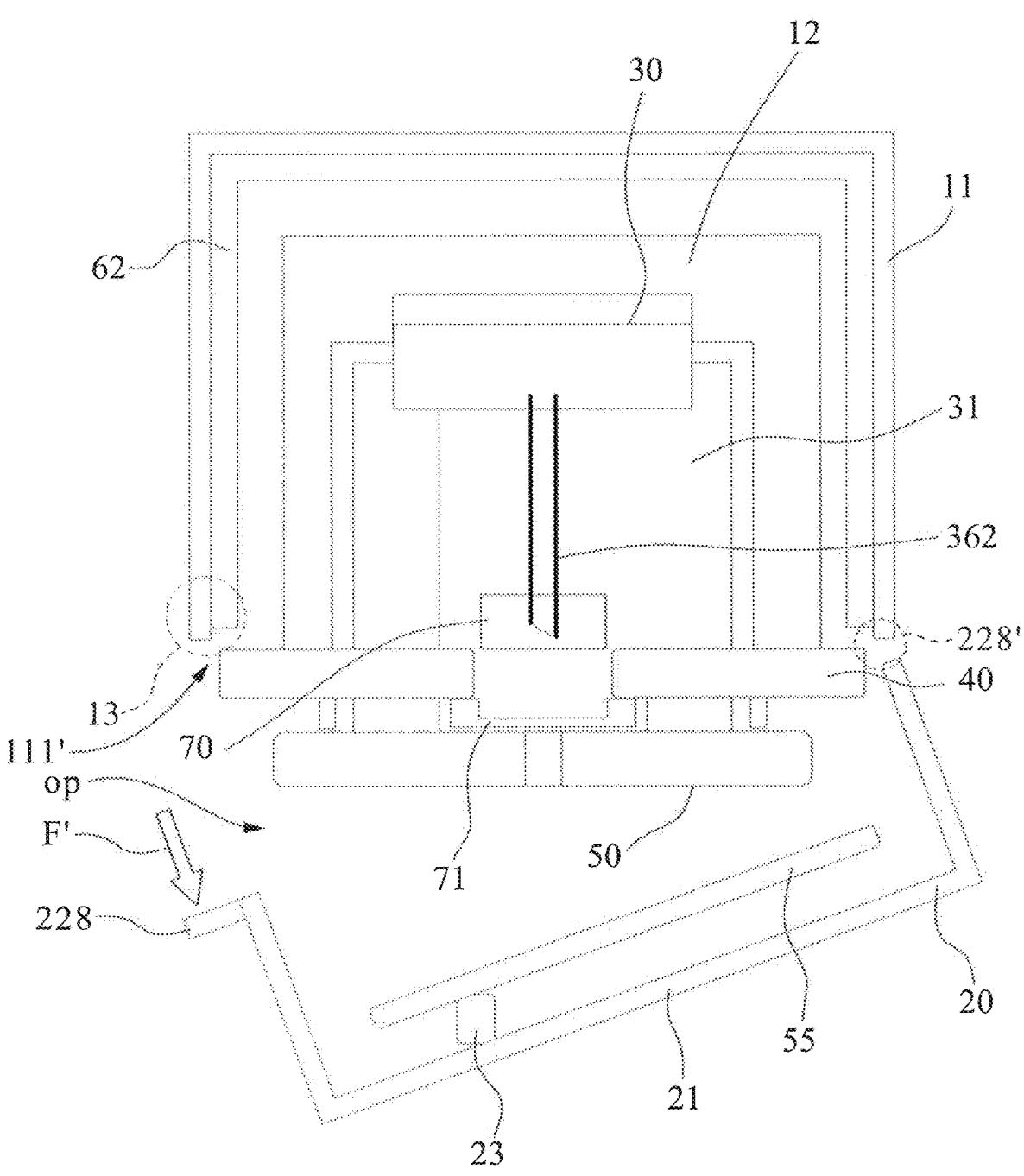
FIG. 26 is a schematic diagram of using a tear-off element to remove a release layer when the bottom cover of the embodiment shown in FIG. 17 is removed.

In another embodiment, as shown in FIGS. 25 and 26, the lower base mount 50 further has a tearing element 23 attached to the chassis portion 21. The tearing element 23 is connected to a release layer 55 which is on the adhesive pad 52. When the container is opened (that is, the bottom cover 20 is removed), the release layer 55 can be torn away along with the tearing element 23, so that the user can tear off the release layer 55 and expose the adhesive pad 52 right before the implantation, which helps to improve adhesion of the adhesive pad 52 to the skin.

In another embodiment, the sensor 72 may be designed to have a certain rigidity, so it is not necessary to be equipped with the needle implant member 36, and the implant module 30 does not need to include the needle extraction device.

In addition, referring to FIG. 27, the operating method of the implantation device according to the present invention can be described as follows:

As shown in FIGS. 3 and 4, the housing 11 is combined with the bottom cover 20 to form the accommodating space 14 therein. The implanting module 30 is disposed inside the accommodating space 14. The needle implanting seat 33 and the main body forms a triggering constraint state. The bottom cover 20 constrains the fixing members 40 to prevent a change from the first operating status (the storage, not implanting status) to the second operating status (the implanting status) under unexpected conditions such as accidental falling and dropping down to the ground.

As shown in FIGS. 5 and 6, the user can remove the bottom cover 20 from the bottom of the housing 11 to release the constraint to the fixing members 40, and place the lower base mount 50 on the skin surface of the living body. In some embodiments, the bottom cover 20 is not removed but opened from the housing during the implantation process.

As shown in FIGS. 7-12, the user can press the housing 11 to release the triggering constraint and cause the implanting module 30 to enter the second operating status from the first operating status. When the implanting module 30 enters the second operating status, the sensor assembly 70 is positioned on the lower base mount 50 and the needle (or sharp) 362 is implanted to the subcutaneous portion, completing the needle implantation process. As shown in FIGS. 13 and 14, during the needle extraction process, the implanting module 30 moves toward the location at the first operating status, and thus the needle 362 is withdrawn back inside the housing 11 without exposing to the outside.

As shown in FIGS. 15 and 16, the bottom cover 20 is re-coupled back to join the housing 11.

Notably, in the assembly sequence of the components of the present invention, the first elastic element 34, the needle extracting seat 35, the second elastic element 37, and the needle implanting seat 33 are previously installed between the main cover 32 and the main body 31, the needle implanting piece 36 is finally put on the auxiliary implantation seat 38 and the sensor assembly 70 therebetween. The needle implanting piece 36 is used to couple to the needle extracting seat 35, whereby the sensor assembly 70 and the implant module 30 forming a clutch design, which can not only greatly improve the assembly yield, but also effectively reduce the cost of the sensor assembly 70.

Figure 2A:
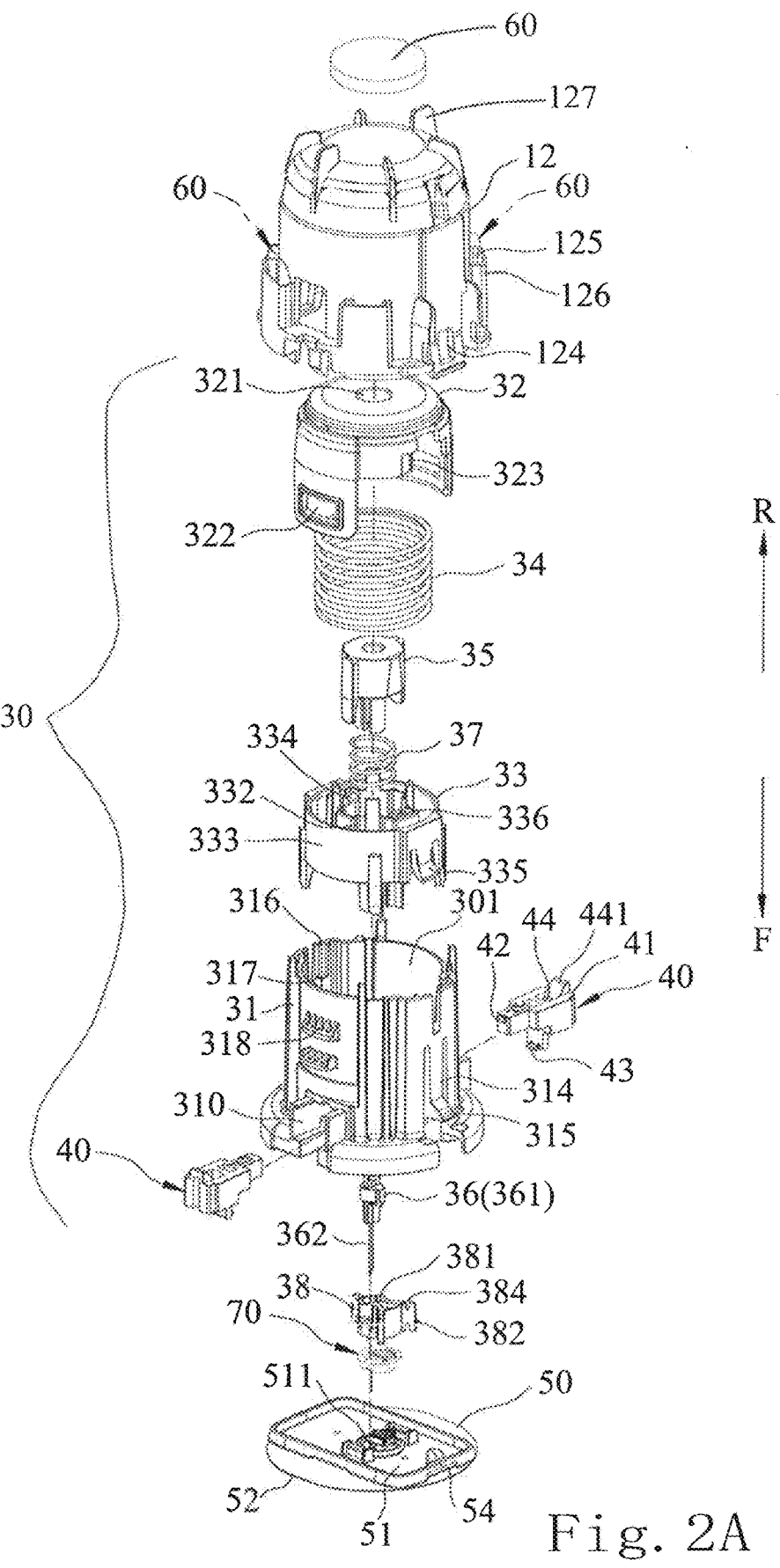
FIG. 2A is an assembly diagram showing more details of some elements according to the embodiment in FIG. 1.
Figure 28A:
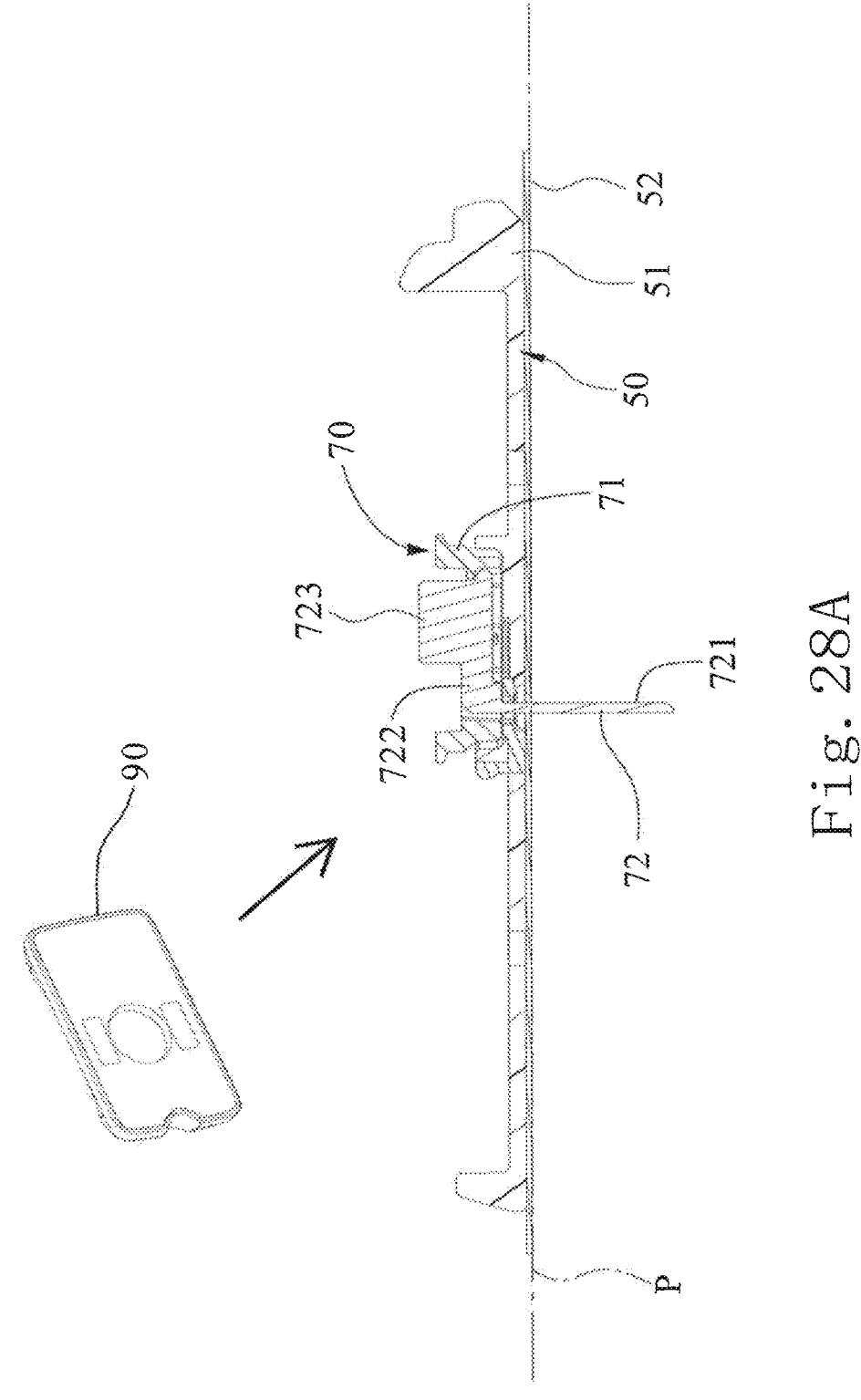
FIG. 28A is a schematic diagram showing the top cover not covering on the base assembly when the needle implanting operation is completed and the sensor is implanted into the subcutaneous portion in the first embodiment.

The assembly method of the desiccating container 100 of the present invention is shown in FIGS. 1 and 28A/B-29. After the components in the implantation module 30 are assembled, the housing 11 is set on the implantation module 30. At this time, the sensor assembly 70 has been pre-clamped inside the implanting module 30 through the auxiliary implantation seat 38, and finally the bottom cover 20 is combined with the housing 11. In other words, the present invention does not require the operation of grasping the sensor assembly 70 onto the lower base mount 50 by the implanting module 30. Basically, the above-mentioned assembly method of the desiccating container 100 is assembled at the factory end, but it is not limited to be assembled by a medical staff or a user by splitting and implanting the module 30. When the user wants to use the apparatus, he or she only needs to easily operate the implantation device, such as pressing the drying container. The sensor assembly 70 on the base 50 is setting through the implantation process, and the adhesive pad 52 of the base 50 will stick the lower base mount 50 to the skin surface.

Figure 28B:
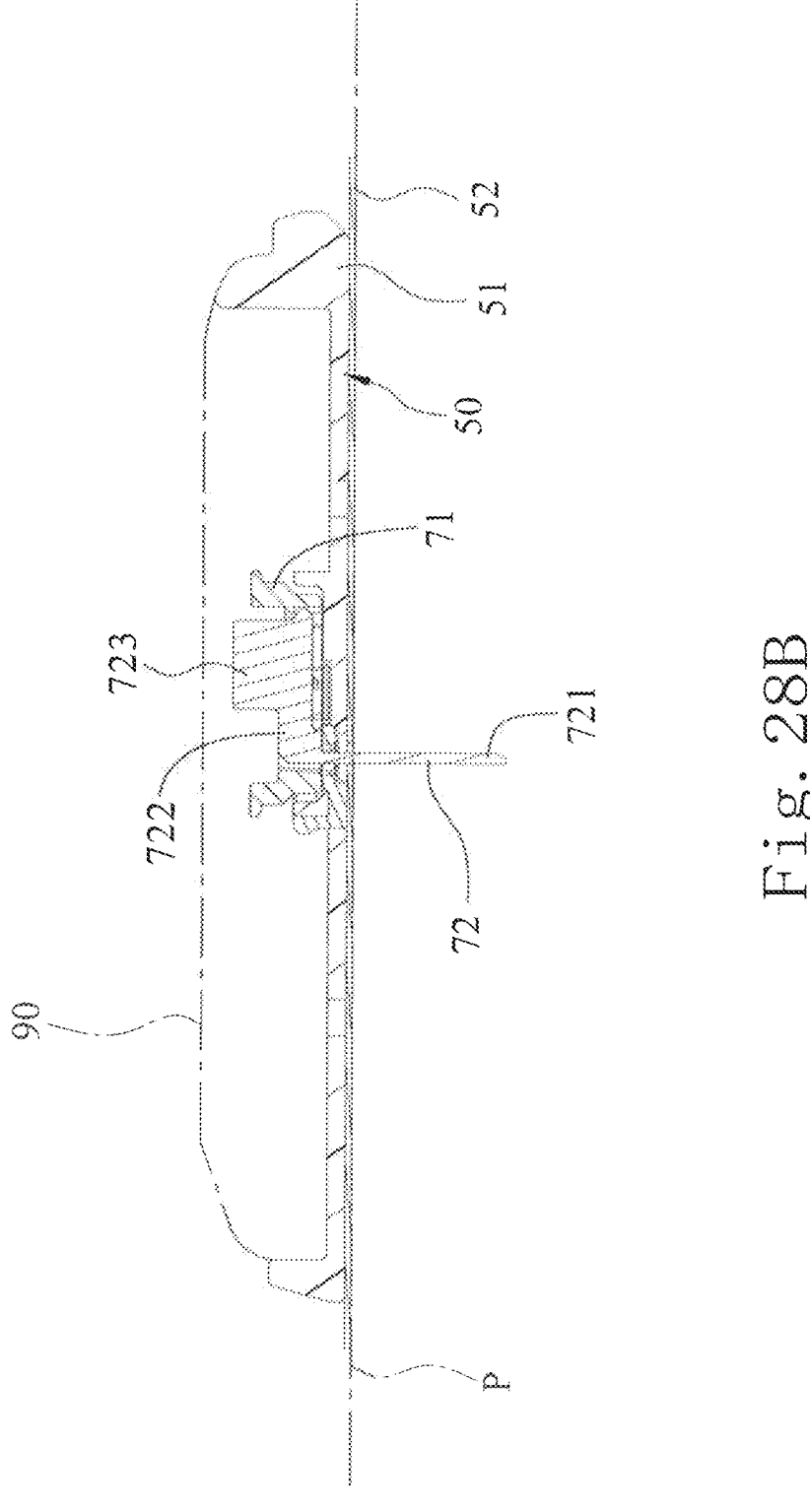
FIG. 28B is a schematic diagram showing the top cover covering on the base assembly after the needle implanting operation is completed and the sensor has been implanted into the subcutaneous portion in the first embodiment.

FIGS. 28A and 28B show that after the sensor 72 is implanted under the skin surface P of the living body, the sensor assembly 70 and the base 50 that are simultaneously disposed on the skin surface P of the living body need to be equipped with the transmitter 90 to work. The transmitter 90 is used to process the physiological signals measured by the sensor 72 and allow the signals to be transmitted to the outside. FIG. 28A shows that the transmitter 90 is not installed on the lower base mount 50, and the outline of the upper dotted line in FIG. 28B shows the transmitter 90 which is installed on the lower base mount 50 in the form of an upper cover. The signals detected by the sensing end 721 is forwarded to the transmitter 90 via the signal output end 723, and then transmitted outward by the transmitter 90. In order to reduce the number of components to be implanted during the implantation process and also reduce the loading of the desiccating container, the detachable module of the present invention does not include a transmitter. The separately arranged the transmitter 90 and the sensor assembly 70 are to ensure the electronic parts are not damaged by the sterilization process, so the production yield of the device can be improved.

Figure 2B:
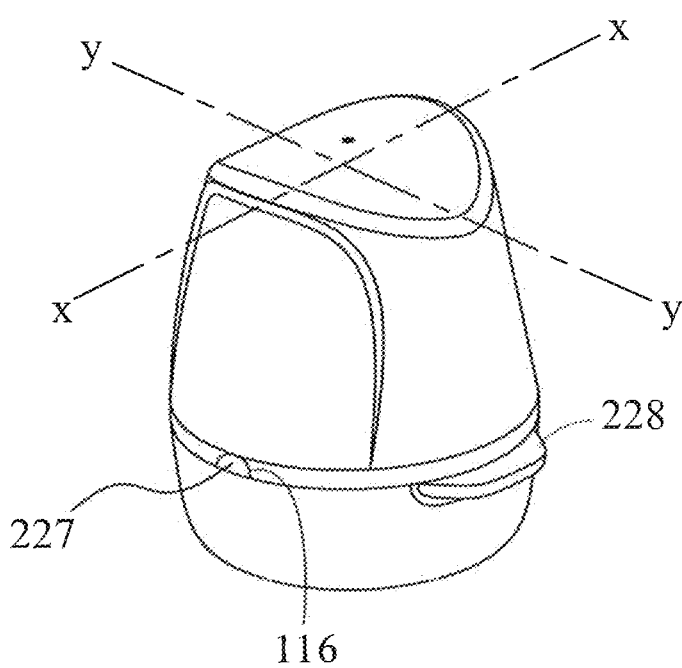
FIG. 2B is a schematic diagram showing a perspective view of the implanting device according to some embodiments of the present invention.
Figure 42:
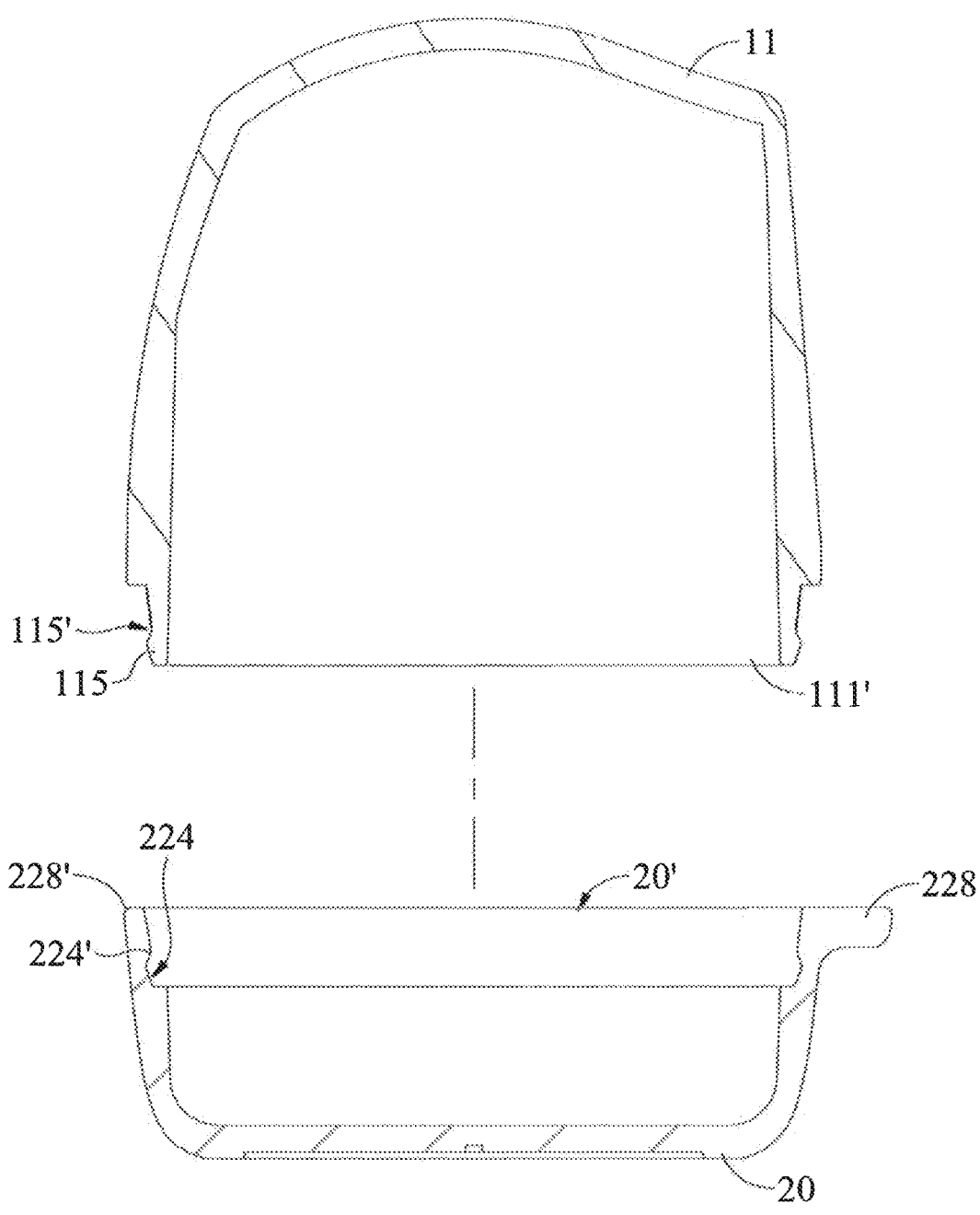
FIG. 42 is a schematic cross-sectional view taken along line y-y of one of the embodiments shown in FIG. 2B, where the housing is separated from the bottom cover.
Figure 43:
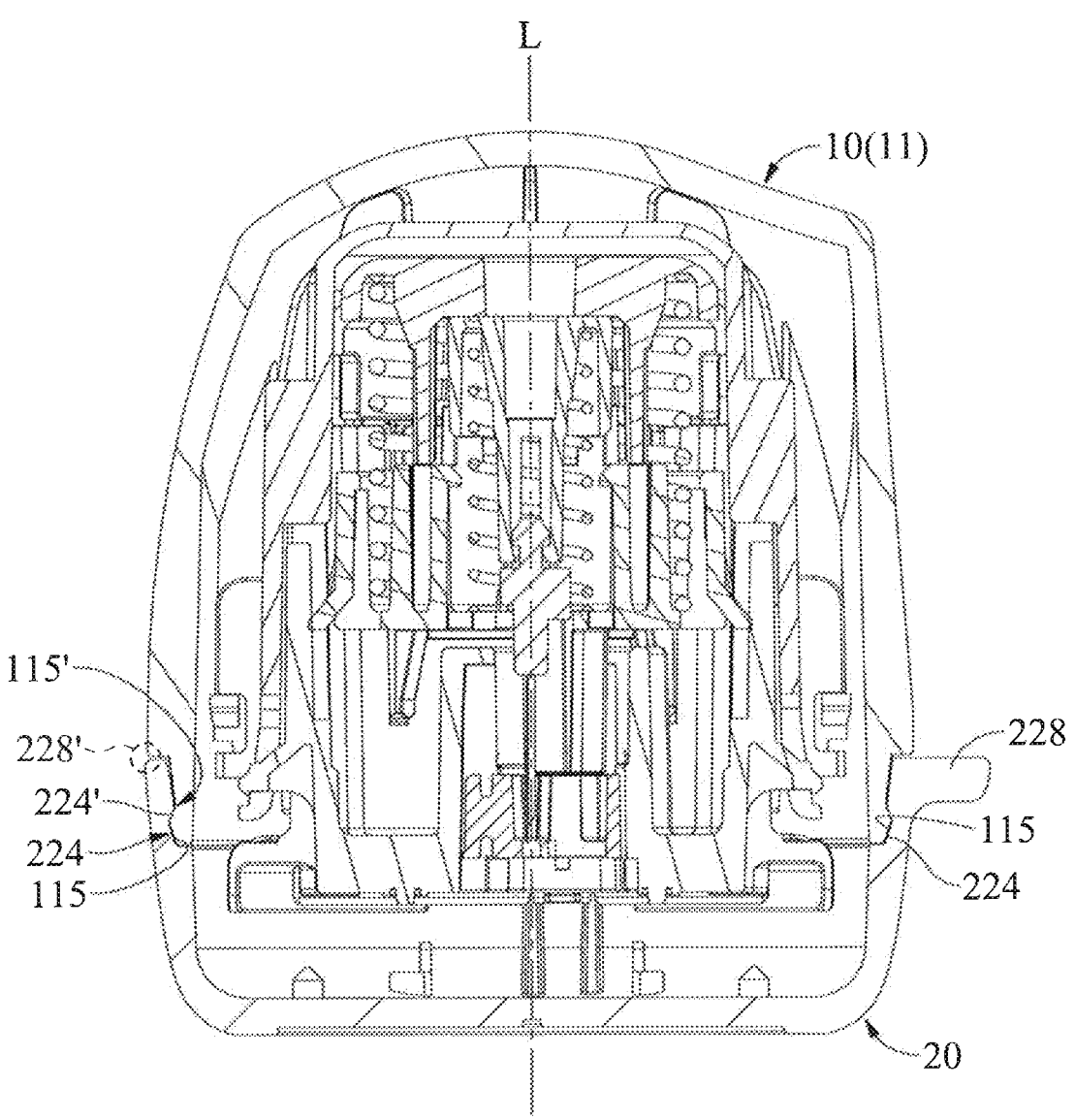
FIG. 43 is a schematic cross-sectional view taken along line y-y of one of the embodiments shown in FIG. 2B.

Please refer to FIGS. 42 and 43, both are regarded as a schematic cross-sectional view along the line y-y of one of the embodiments shown in FIG. 2B, but the housing 11 and the bottom cover 20 in FIG. 42 are separated. A convex ring 115 beside the bottom opening 111' under the housing 11, which is used to combine with the ring groove 224 of the bottom cover 20, so that the bottom cover 20 and the housing 11 can be engaged tightly through hard interference. In FIG. 42, a bottom cover convex ring 224' is formed near the bottom cover opening 20' to abut the convex ring 115, and a housing ring groove 115' is formed on the housing 11 to accommodate the bottom cover convex ring 224'. It can be seen that, in FIG. 43, the bottom cover convex ring 224' is located above the convex ring 115, and the convex ring 115 is also located in the ring groove 224, thus achieving the effect of hard interference and preventing the bottom cover 20 from being separated from the bottom opening 111'. The convex ring 115 and the housing ring groove 115' illustrated in FIGS. 42 and 43 face outward, i.e. opposite to the bottom opening 111', while the ring groove 224 and the bottom cover convex ring 224' face inward, i.e. facing the bottom cover opening 20'. Therefore, if the bottom cover 20 is to be removed from the bottom opening 111', the bottom cover convex ring 224' must pass through the convex ring 115, that is, break through the barrier of the convex ring 115. In addition, a leak-proof ring 13 (referring to FIG. 4) can be additionally provided on the housing ring groove 115', which is not only tightly sealed with the housing ring groove 115', but also tightly sealed with the bottom cover convex ring 224' so as to achieve an airtight and moisture-proof effect. In a different embodiment, the convex ring 115 is disposed on the bottom cover 20 while the ring groove 224 is on the bottom opening 111'.

Figure 44:
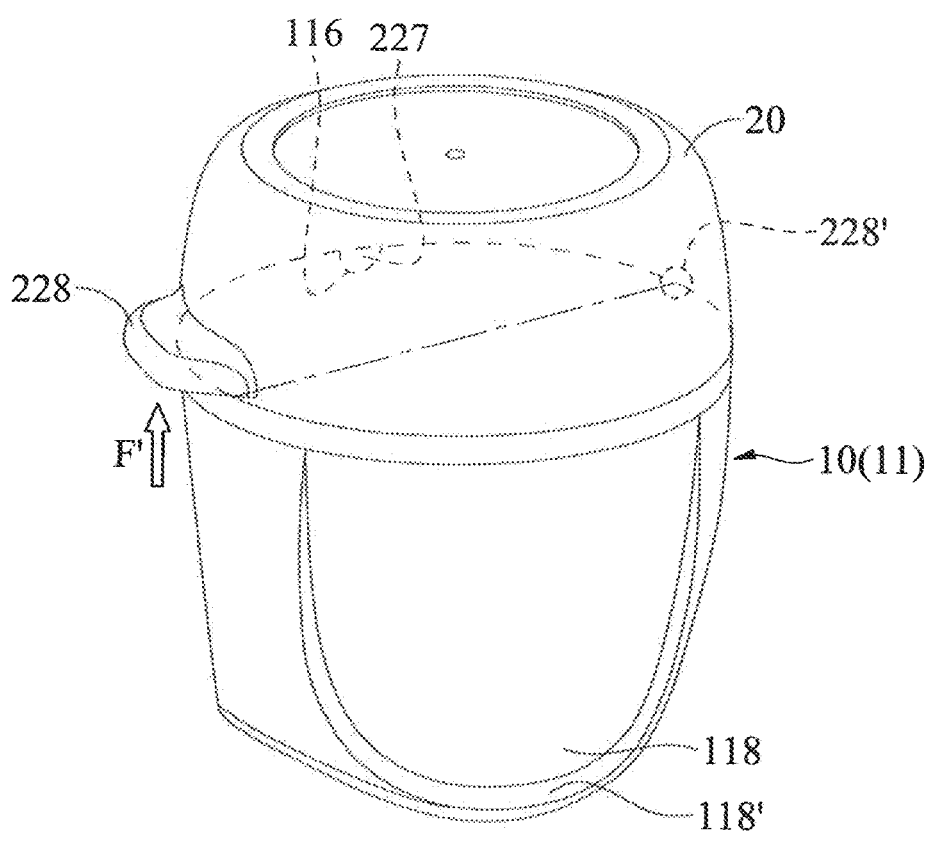
FIG. 44 is a schematic perspective view of the combination of the bottom cover and the housing of the present invention.
Figure 45:
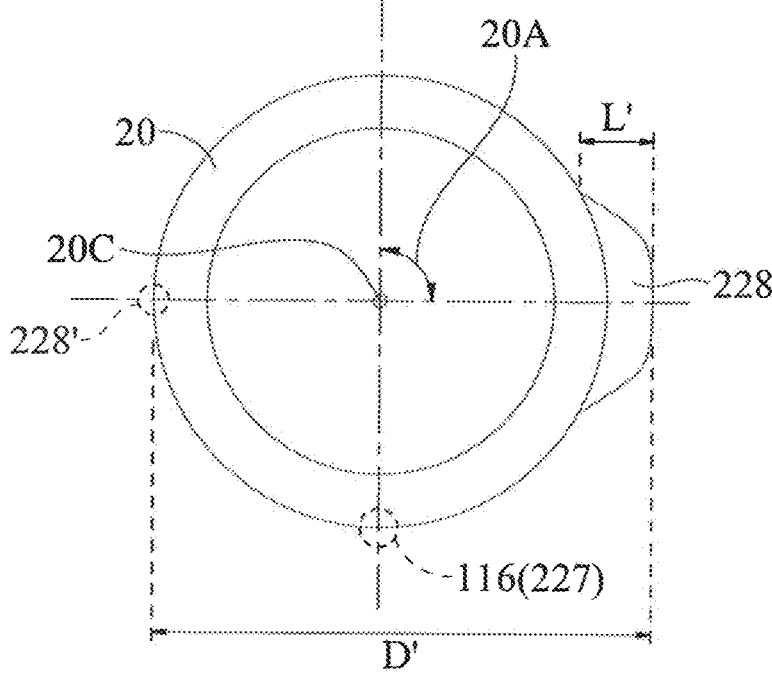
FIG. 45 is a top view of the combination of the bottom cover and the housing according to the FIG. 44.

Please refer to FIGS. 44 and 45, it can be seen that the lateral surface of the housing 11 has a recessed portion 118 and a flange 118', the bottom cover 20 has a operating portion 228, and the opposite end naturally becomes a force support portion 228' providing support in the process when the bottom cover 20 is opened. The principle of force application is that a distance D' from the force support portion 228' to the operating portion 228 and the applied force (F') form a force moment, that is, the "force moment" is equal to the "distance (D')" multiplied by the "applied force (F')". Therefore, the size of the housing 11 and the magnitude of the force required for opening the housing 11 can be adjusted by controlling the distance (D') and the applied force (F').

For example, if the implant device is to have better air-tightness, in principle, the tighter the bottom cover 20 and the housing 11 are, the better, but this also results in excessive force required to open the bottom cover 20, which is extremely inconvenient to use. When the user applies excessive force in order to open the bottom cover 20, the implant device is often thrown out of the hand, causing damage to the internal object. Taking the implantation device of the present invention as an example, the inventor devised a cover-opening moment design of the implantation device that can take both easy opening and air-tightness of the device into account. Considering that the container may accommodate different forms or different sizes of needle implanting mechanisms and/or needle subtracting mechanism, 15~100 mm is a very appropriate distance, and the preferred range is 30~80 mm for the distance D' from the operating portion 228 to the force support portion 228'. Regarding the applied force F', a larger range is 0.2~10 kgf, a common range is 0.5~6 kgf. If one wants to open the bottom cover 20 with a smaller force, the range falls within 1~3 kgf, or the opening force can be less than or equal to 2 kgf.

Therefore, through the arrangement and combination of the range of applied force F' and that of the distance from the support part to the force D', the "applied moment" is approximately 3 to 1000 kgf-mm, a better range is 6 to 800 kgf-mm, an even better range is 15 to 480 kgf-mm, and the much better range is 30 to 240 kgf-mm. If one needs to open the container with smaller force, the moment can be less than or equal to about 200 kgf-mm. When the size of the bottom opening is unchanged, the applied moment can be adjusted by adjusting the size of the operating portion 228. Because the operating portion 228 is a convex portion, the length (L') of the convex portion is no less than 1 millimeter.

As shown in FIGS. 46A to 46D, which is a schematic diagram of the continuous action of opening the bottom cover 20 according to an embodiment of the present invention, when the operation portion 228 is operated, a side opening op between the housing 11 and the bottom cover 20 can be formed due to the applied moment to make the bottom cover 20 leave the bottom opening 111' of the housing 11, so that the housing 11 is in an operable state, and the implantation module 30 can automatically release a force to implant a part of the sensor 72 subcutaneously to measure the physiological signal. In addition, the bottom cover 20 has a positioning piece 227 for matching with the matching portion 116 on the housing 11 (referring to FIG. 1 and FIG. 2B). The bottom cover 20 has a center point 20C. A first imaginary line L1 extends from the center point 20C to the matching portion 116 (the positioning piece 227), and the center point 20C extends a second imaginary line L2 toward the operating portion 228. The first and second imaginary lines (L1, L2) form an angle 20A between 5 and 180 degrees.

Please refer again to FIGS. 46A to 46D, which are schematic diagrams of the continuous action of opening the bottom cover 20 of another embodiment of the present invention. The series of continuous action diagrams are based on the side view of the housing 11 of the present invention combined with the bottom cover 20 facing upward. First, please look at FIG. 46A, which shows that the bottom cover 20 has an operating portion 228, and the opposite end of the operating portion 228 forms a force support portion 228'. When a user tends to open the bottom cover 20, he/she may apply the applied force F' in the direction away from the housing 11 at the operating portion 228. In one embodiment of the present invention, the bottom cover 20 is formed of a relatively elastic material. Because there is a desiccant 60 in the housing 11, when it absorbs moisture, the air pressure inside the housing 11 is slightly reduced to be less than the atmospheric pressure, so the atmospheric pressure provides additional pressure to make the bottom cover 20 fit more closely to the housing 11.

Figure 46A:
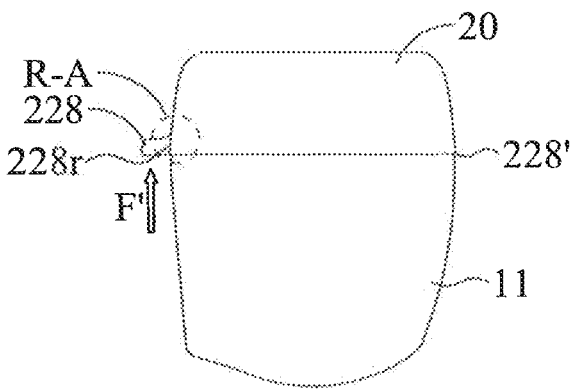
FIG. 46A-46D are schematic diagrams of an continuous action of opening the bottom cover according to one embodiment of the present invention.

In FIG. 46A, when the operating portion 228 is pushed by the applied force F' but the side opening (or partial side opening) OP is not yet formed between the bottom cover 20 and the housing 11, the first abutment R-A is located near the root portion 228_r_ and the outwardly protruding operating portion 228 can provide an additional force arm for the applied force F' to increase the moment for opening the bottom cover 20. Once a slight amount of detachment is generated between the bottom cover 20 and the housing 11, the inflow of external air can balance the internal and external air pressure of the housing 11, so it is easier to detach the bottom cover 20 from the housing 11.

Figure 46B:
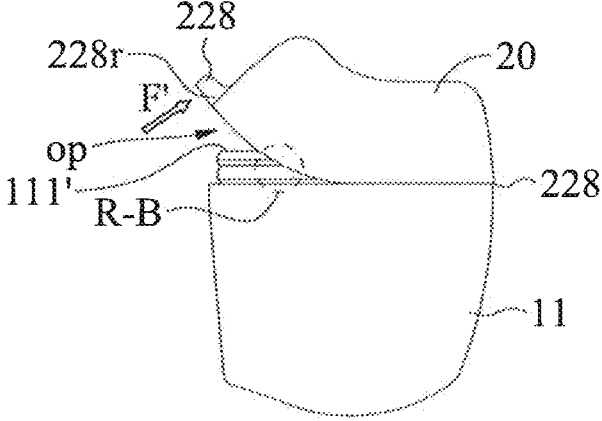
Figure 46C:
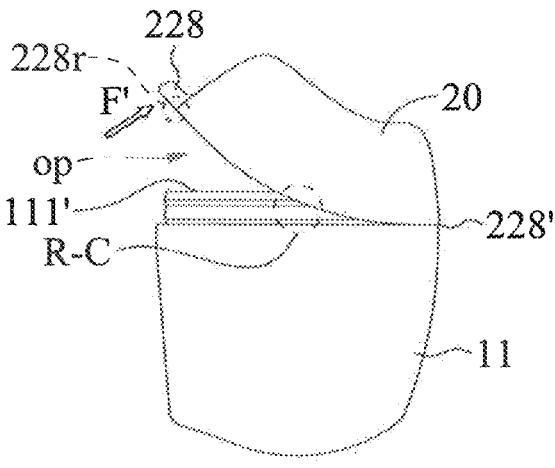
Figure 46D:
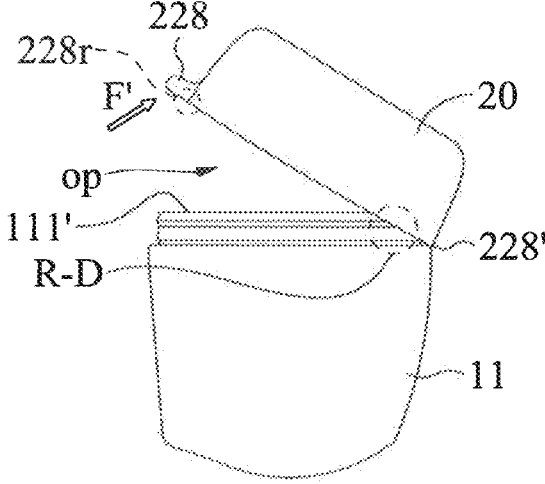

Referring to FIGS. 46B to 46D, as the applied force F' continues to be applied to the operating portion 228, the side opening OP gradually expands, and the position where the resistance force generated due to the combination between the bottom cover 20 and the housing 11 is moved from the first abutment R-A to the second abutment R-B, or, according to a different perspective, from the vicinity of the root portion 228_r_ of the operating portion 228 to the force support portion 228'. As shown in FIG. 46B, the second abutment R-B is farther from the operating portion 228, so the force arm is longer and the moment is greater, and thus the opening operation is easier. Similarly, in FIG. 46C, the distance between the third abutting location R-C and the operating portion 228 is farther than that of the second abutting location R-B and the operating portion 228, so the force arm is longer and the opening application is much easier. Finally, in the situation of FIG. 46D, the bottom cover 20 is about to be fully opened. At this moment, the fourth abutment R-D almost coincides with the force support portion 228', and the length of the entire force arm is close to the diameter of the bottom cover 20 plus the length of the operating portion 228. Although the deformation of the bottom cover 20 in FIGS. 46A to 46D is a bit exaggerated, as a matter of fact, if the bottom cover 20 is made of a stiffer material, the deformation will be quite small when the bottom cover 20 is opened. Nonetheless, the change at the force support portion 228' is still similar as that shown in FIGS. 46A to 46D.

Figure 29:
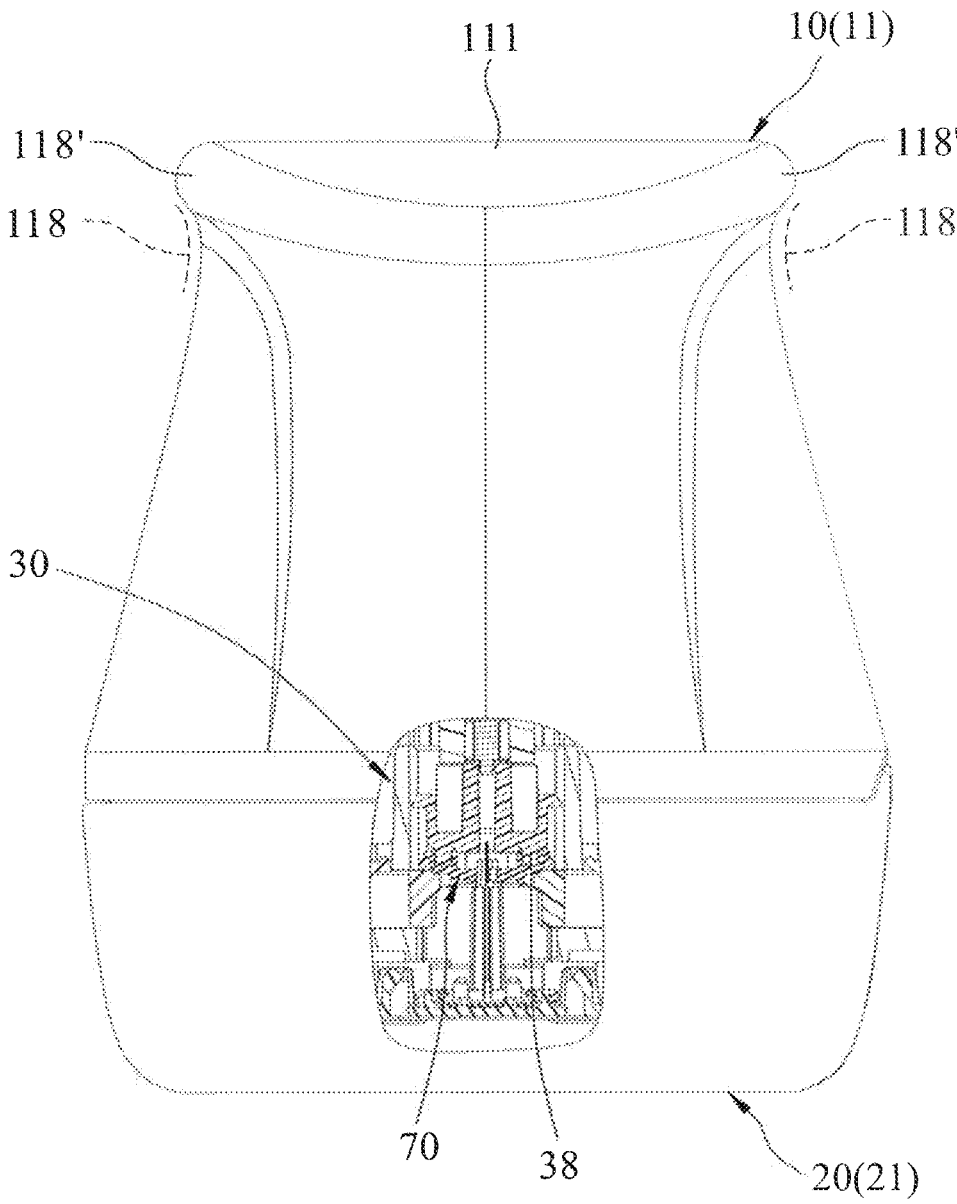
FIG. 29 is a schematic diagram showing an enlarged portion of FIG. 3, illustrating that the sensor assembly is clamped inside the air-tight and desiccating container by a needle implantation support.
Figure 30:
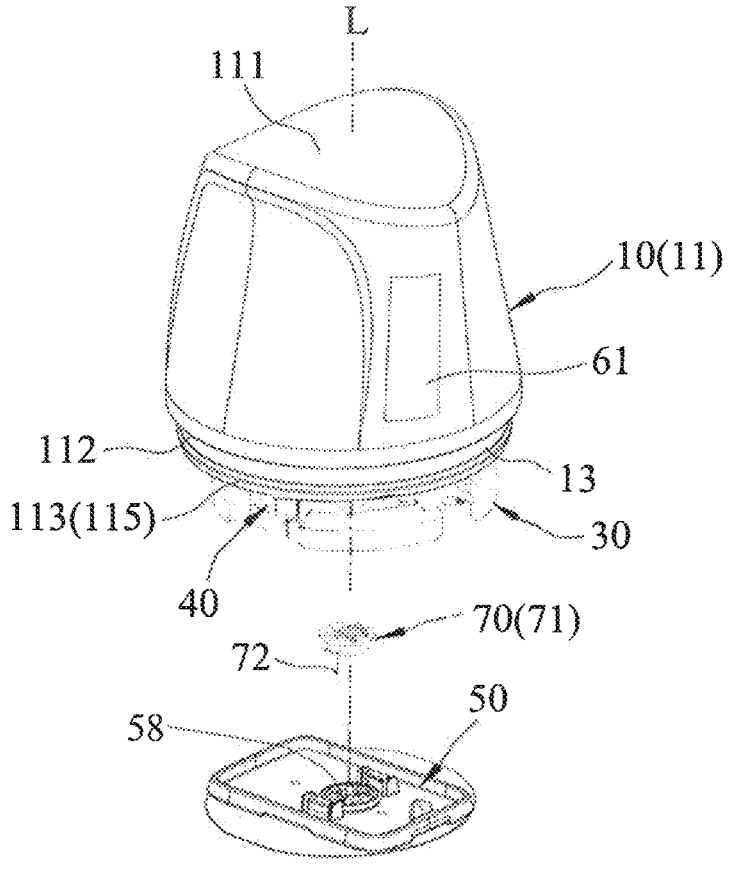
FIG. 30 is an assembly diagram similar to that of FIG. 1.
Figure 47:
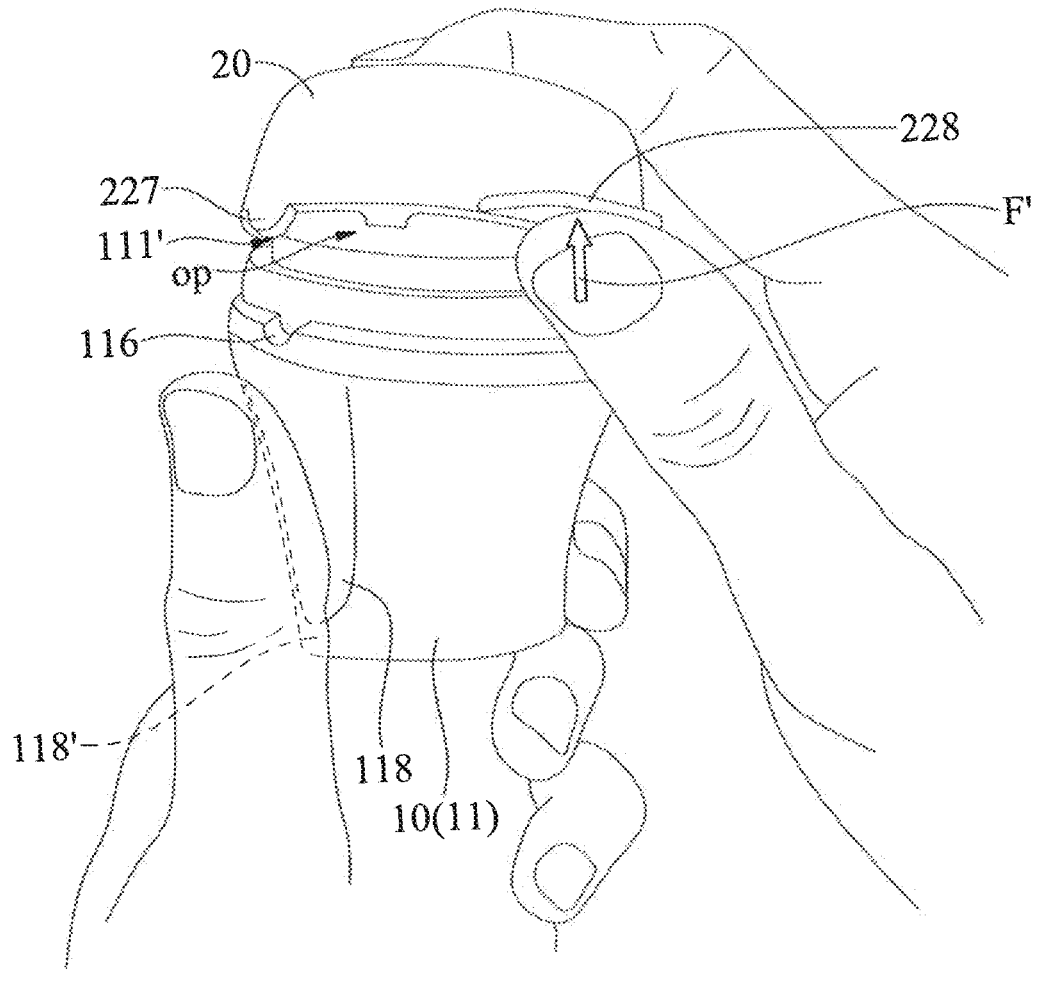
FIG. 47 is a schematic perspective view showing a user to remove the bottom cover from the housing by hands according one embodiment of the present invention.

Please refer to FIG. 47, disclosing that the user holds the housing 11 with one hand, and apply the force F' to pulls the operating portion 228 with the fingers of the other hand to open the bottom cover 20, and a side opening OP between the bottom cover 20 and the housing 11 is formed. The manner for holding the housing 11 can be chosen according to user's convenience. Since the direction of force borne by the force applying portion 228 is away from the bottom opening 111', the clamping between the convex ring 115 and the ring groove 22 during the bottom cover 20 opening process will also cause the applied force F' to give the housing 11 a tendency to move in the direction of the applied force F'. However, the user must be able to hold the housing 11 to resist this tendency so as not to allow the housing 11 to accidentally fly out. The recess 118 of the housing 11 of the present invention (referring to FIG. 29) is configured for the user's hand to hold firmly, and because the flange 118' stops the hand, the housing 11 is not easy to come out of the hand along the axial direction of the housing 11.

Figure 48:
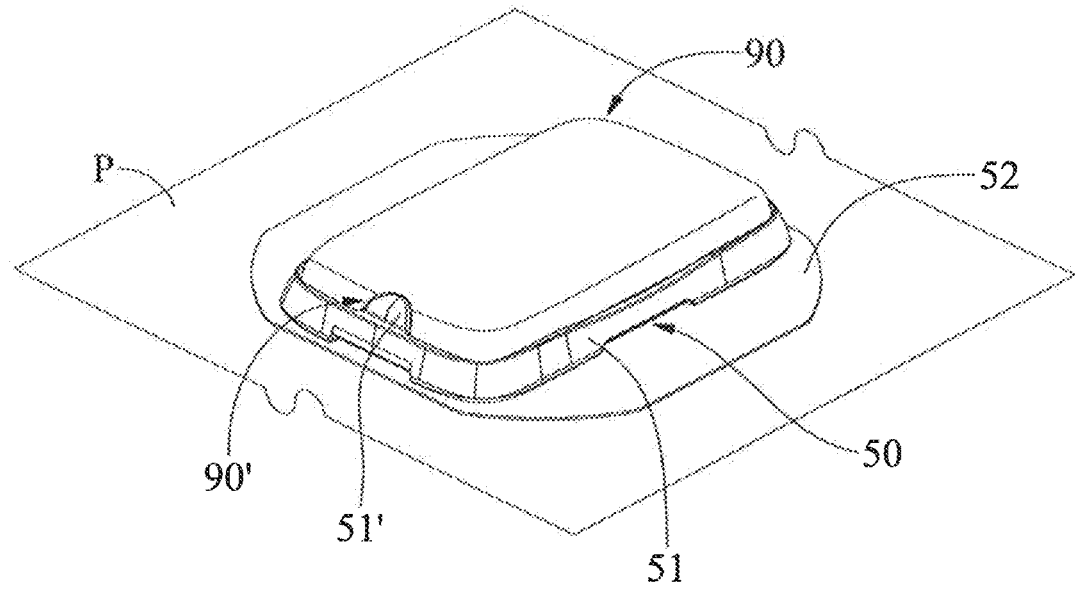
FIG. 48 is a schematic diagram of the combination of the transmitter placed on the base attached to a body surface via the attaching pad according one embodiment of the present invention.
Figure 49:
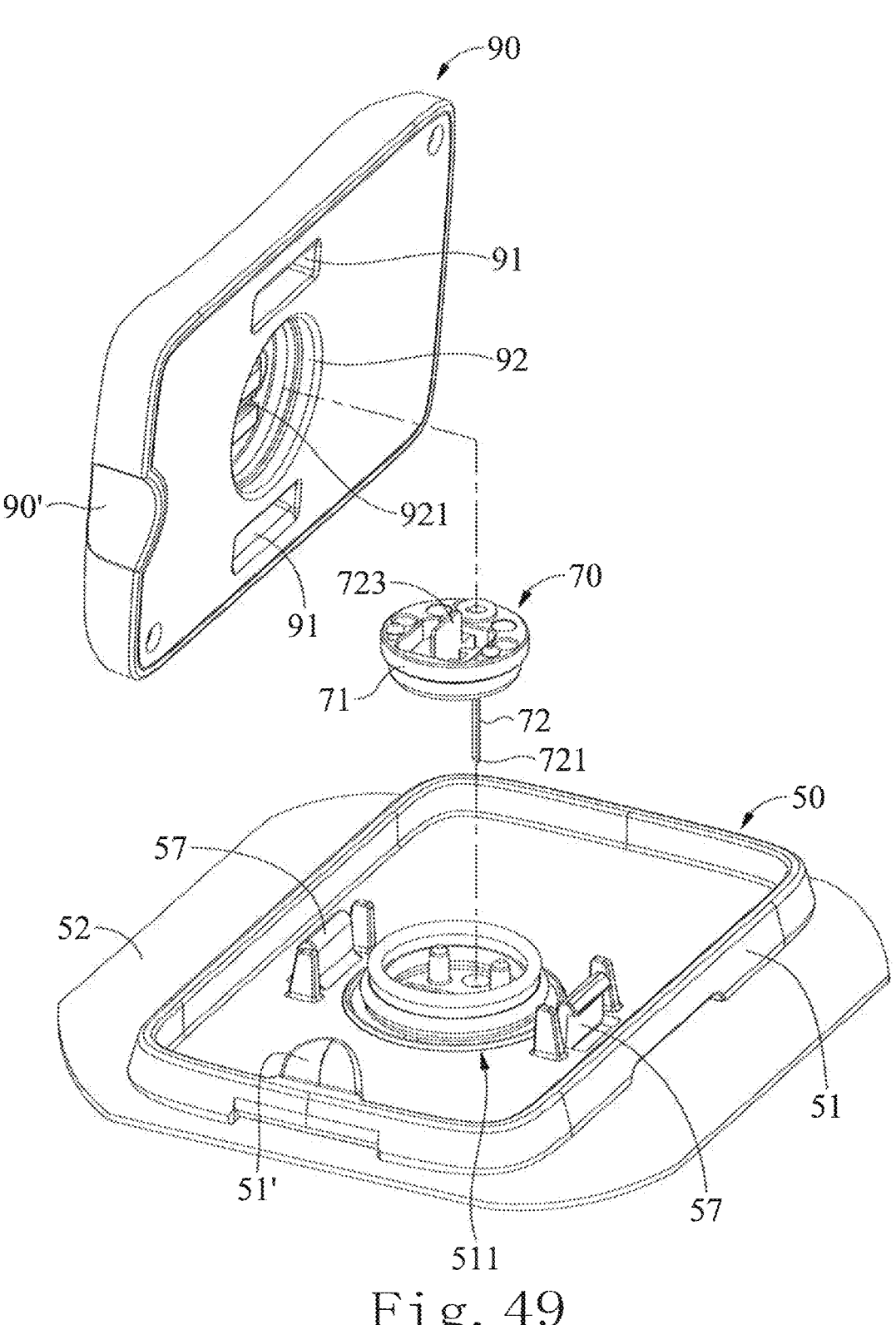
FIG. 49 is an exploded schematic diagram of the transmitter, the base and the sensor assembly of the present invention.

Please refer to FIGS. 48 and 49, where it can be seen that the sensor 90 is disposed on the lower mount base 50, and the second positioning portion 90' of the sensor 90 fits with the first positioning portion 51' of the lower mount base 50, which also has a foolproof effect, that is, if the mounting direction of the sensor 90 is opposite to that in FIG. 48, it cannot be disposed on the lower mount base 50. The sensor assembly 70 is disposed on the sensor assembly positioning portion 511 during the implantation process. Refer to FIG. 28B. The signal sensing end 721 of the sensor 72 is implanted subcutaneously, and the other end of the sensor 72 is the signal output end 723 exposed at the top of the sensor base 71. When the transmitter 90 is covered on the base 50, the signal output end 723 will be electrically connected to the electrical connection port 921 in the input portion 92 of the transmitter 90, and then the transmitter 90 will wirelessly transmit the physiological signal measured by the sensor 72. The transmitter 90 is fixed on the lower mount base 50 through the coupling of its own sensor fixing groove 91 and the sensor fixing buckle 57 on the lower mount base 50. An adhesive pad 52 (see FIG. 48) is provided at the bottom of the base 50, and the sensor module (or detachable module, including the base 50 and the sensor assembly 70) is fixed on the surface P of the biological skin through the adhesive pad 52.

Figure 50:
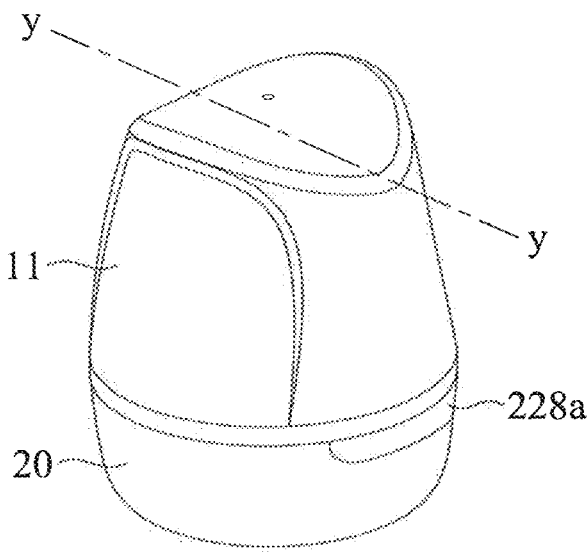
FIG. 50 is a schematic diagram of a housing and a bottom cover of the implantation device according to another embodiment of the present invention.
Figure 51:
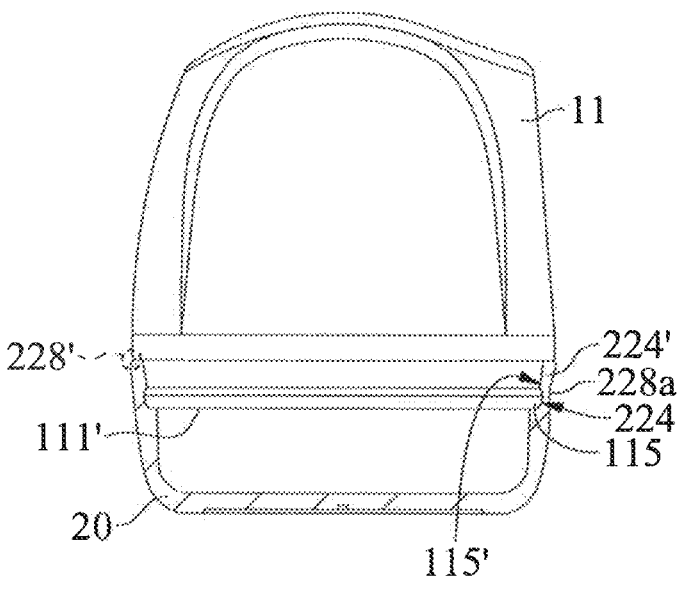
FIG. 51 is a schematic cross-sectional view along the line y-y of the embodiment in FIG. 50.

Please refer to FIGS. 50 and 51, showing that a second operating portion 228_a_ is a recessed structure extending along the outer side wall of the bottom cover 20, and the recessed structure can provide with the fingers greater friction to facilitate the user to detach the bottom cover 20 from the bottom opening 111' in a similar manner. As to the connection relationship among elements such as the convex ring 115, the housing ring groove 115', the ring groove 224, and etc. is the same as the illustration in FIG. 42, there is no need to repeated here.

Figure 52:
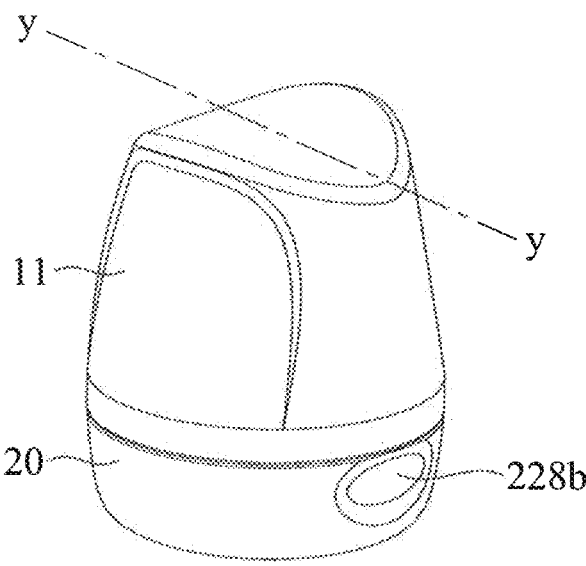
FIG. 52 is a schematic diagram of a housing and a bottom cover of the implantation device according to yet another embodiment of the present invention.
Figure 53:
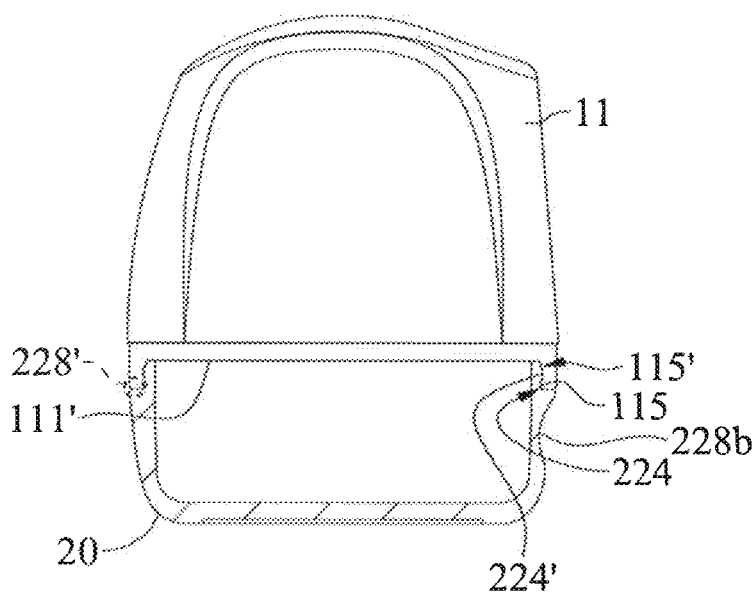
FIG. 53 is a schematic cross-sectional view along the line x-x of the embodiment in FIG. 52.

Please refer to FIGS. 52 and 53, showing that a third operating portion 228_b_ is a concave structure which can provide the fingers with a relatively larger friction force to facilitate the user to detach the bottom cover 20 from the bottom opening 111' in a similar manner. Different from the embodiments in FIGS. 51 and 42, the convex ring 115 and the housing ring groove 115' on the housing 11 face inward, that is, point to the center of the bottom opening 111', while the ring groove 224 and convex ring 224' of the bottom cover 20 face outward, that is, facing the convex ring 115 and the housing ring groove 115'. It can be appreciated that, in the embodiment of FIG. 53, the ring groove 224 and the bottom cover convex ring 224' are surrounded by the convex ring 115 and the housing ring groove 115'. Therefore, when the user squeezes the third operating portion 228_b_, the bottom cover 20 will be slightly concaved inward, so that the ring groove 224 and the convex ring 115 are separated from the contact state, and a gap is created for air to flow in, so that the housing 11 can no longer maintain negative pressure, that is, the air pressure inside and outside the housing 11 is balanced, making it easier for the user to detach the bottom cover 20.

Figure 54:
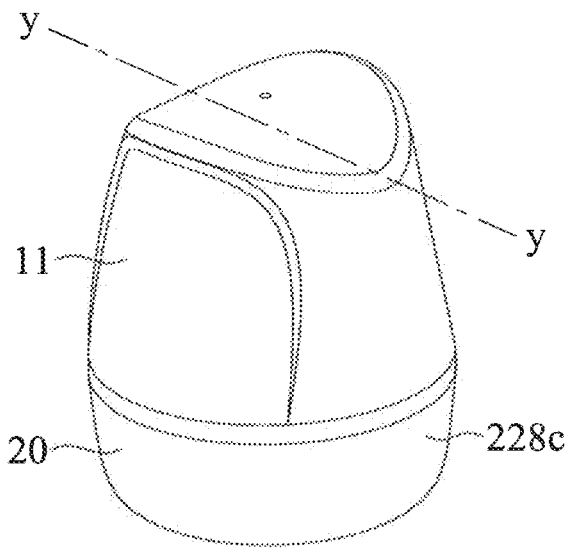
FIG. 54 is a schematic diagram of a bottom cover of the implantation device according to another embodiment of the present invention.
Figure 55:
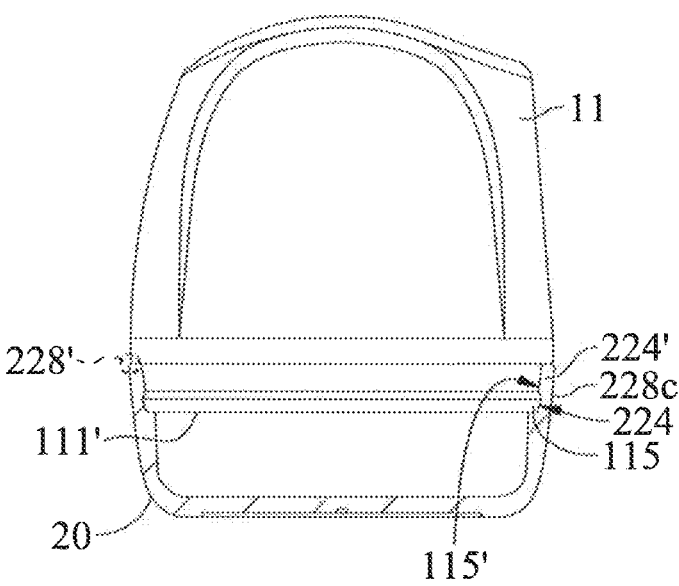
FIG. 55 is a schematic cross-sectional view along the line y-y of the embodiment in FIG. 54.

Please refer to FIGS. 54 and 55, which disclose that the bottom cover outer wall 228_c_ of the bottom cover 20 can directly serve as an operation portion, that is, the user may directly apply a force on the bottom cover outer wall 228_c_ and a force to the bottom cover 20 along the direction away from the housing 11 in order to open the bottom cover 20. Since the entire periphery of the bottom cover outer wall 228c can be used as the operation portion, when the user chooses a location on the bottom cover outer wall 228c to apply the force, the opposite side of this location can be regarded as the force support portion 228'.

Figure 56:
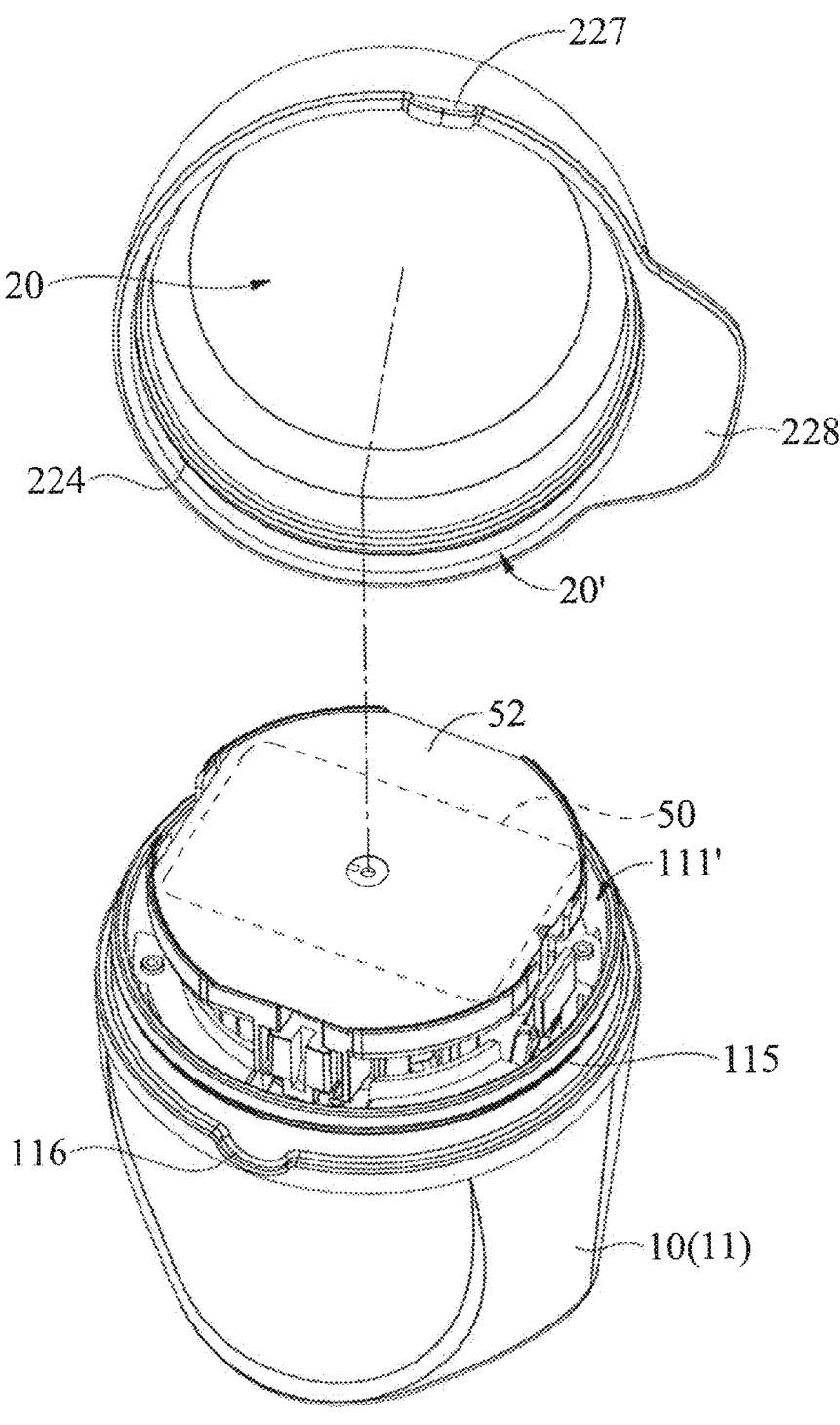
FIG. 56 is a schematic perspective view of the implantation device after the bottom cover has been opened.

Please refer to FIG. 56, a schematic perspective view of one embodiment of the present invention after the bottom cover is detached from the housing, which only takes the protruding operating portion 228 as an example, but the present invention is not limited to this. The embodiments of FIGS. 50 to 53 are substantially the same after the bottom cover 20 has been opened. When the bottom cover 20 is separated from the bottom opening 111', it can be seen that the adhesive pad 52 has an adhesive side, and below it is the lower mount base 50. A convex ring 115 can be seen near the bottom opening 111'. The annular groove 224 can be seen from the bottom cover opening 20' of the bottom cover 20, and the positioning piece 227 has also been disengaged from the matching portion 116. The user may then press the adhesive pad 52 against the living body's skin surface P where the sensor 72 (referring to FIG. 49) and operate the housing 11 to achieve the effect of disposing the sensor.

The main efficacy of the present invention are summarized as below:

First, in the desiccating and air-tight container of the present invention, the bottom cover is air-tightly combined with the housing, so that the housing and the bottom cover form an air-tight space, and in combination with the setting of the desiccant, deliquescence of the chemical reagent on the sensor in the airtight space can be avoided, which ensures the detection accuracy of the sensor. In addition, a drying indication unit can also be added to the outside or inside of the housing (preferably, the drying indication unit can be a drying indication material), with a transparent or translucent portion on the opposite part of the housing, so that the user can identify whether the sensor has been made wet by means of the drying indication unit. The manner and location of the desiccant are not limited by the types disclosed in the examples.

Second, the way of air-tight combination of the air-tight container according to the present invention is through the joining method of the convex ring and the ring groove. When the container is closed, the moisture absorption in the container is no more than 200 mg per day, or no more than 50 mg per day, or no more than 1 mg per day, or no more than 0.5 mg per day, or no more than 0.3 mg per day, or not more than 0.25 mg per day, and the container achieves a store condition at a relative humidity of 0-100% and a temperature of 0-45° C., or storage conditions with relative humidity of 0-100% and temperature of 0-40° C., or storage conditions of relative humidity of 10-90% and temperature of 4-30° C., and can be maintained for at least 2 years or at least 1 year of effectiveness during storage with effects of good air-tightness, easy to open and resistance to negative pressure. The invention can also achieve the effect of air-tight bonding through the way of hard interference.

Third, the detaching module of the present invention does not include a transmitter, and the transmitter and the sensor assembly are separately arranged to ensure that the electronic components in the transmitter will not be damaged due to the high temperature or chemical environment required by the sterilization process, so the production yield of the transmitter can be improved.

Fourth, the implant module of the present invention mainly uses the elastic forces provided by the two pre-compressed elastic members to make the implant module an automatic mechanism sequentially using the first and the second elastic members. The elastic forces for implanting and withdrawing needles are provided by the implant module, so there is no need to rely on the force from the user's hand to press down the needle. It also has the effect of one-step pressing the housing assembly to complete the automatic needle implantation as well as needle withdrawal action. In other words, the present invention can greatly improve the operational certainty, and can effectively solve the problem of the prior art that the smoothness of the implanting and needle extraction can be affected due to the user's proficiency during operation.

Fifth, when the overall assembly of the desiccating and air-tight container according to the present invention is completed and not yet in use, the constraint portion formed by the abutting portion of the bottom cover and the engaging portion of the housing can avoid accidental implanting of the needle due to the container accidentally falling during transportation.

Sixth, the needle piece is extracted into a position between the needle implanting seat and the auxiliary implantation seat to avoid being exposed, which may achieve the effect of hiding the needle piece after use.

Seventh, the main cover compresses and accumulates the first elastic element so that the first elastic element does not directly contact the casing assembly. Therefore, the operator does not need to resist the elastic force from the first elastic element when the casing assembly is pressed down for the needle implantation operation, which renders the implantation operation effortless.

Eighth, due to the restriction relationship formed by the auxiliary implantation seat and the main body before the needle is implanted, the left-right deviation and pulling can be avoided when the needle is implanted under the skin of the living body, which improves the stability of the needle stroke and reduces the pain of the living body or the patient.

Ninth, after the user presses the casing assembly by hand, the implanting module is triggered and automatically uses the elastic force provided by the first and the second elastic elements to sequentially implant and extract the needle, thereby completing the automatic needle implanting and extracting time is no more than 100 ms, or no more than 50 ms, or even less than 8 ms, 6 ms, 4 ms or 2 ms.

Tenth, in the assembly sequence of the components of the present invention, the first elastic element, the needle extracting mount, the second elastic element and the needle implanting seat are previously installed between the main cover and the main body, the needle implanting piece is finally put on the auxiliary implantation seat and the sensor assembly therebetween. The needle implanting piece is used to couple to the needle extracting mount, whereby the sensor assembly and the implant module forming a clutch design, which can not only greatly improve the assembly yield, but also effectively reduce the cost of the sensor assembly.

Eleventh, the sensor assembly of the present invention is pre-assembled with the implanting module through the auxiliary implantation seat, and finally the bottom cover is combined with the housing. In other words, the present invention does not require the operation of grasping the sensor assembly onto the lower base mount by the implanting module.

Twelfth, a protective ring can be sleeved on the bottom of the housing according to one embodiment of the present invention. The lower base mount is disposed on the inner side of the bottom edge of the protective ring before the implantation operation, so when the bottom edge of the protective ring buts against the skin surface of the living body, the lower base mount will not contact the skin surface. The user can move the implantation device to the position to be implanted, and the triggering action of pressing down the casing assembly or the housing is performed afterwards. Therefore, with the aid of the protective ring of this embodiment, it can be adjusted to the required position enforce the needle implantation operation is performed, which is quite convenient to use.

Thirteenth, several embodiments are available for the operating portion. In the first embodiment, the outer side surface of the bottom cover has a operating portion adjacent to the brim and protruding from the outer side surface allowing a user to cause thereby a side detachment between the bottom cover and the housing by the force moment so that the bottom cover can be easily opened. In the second embodiment, a recessed portion on the outer side surface of the bottom cover can be the operating portion for the user's finger or nail to firmly push thereon to avoid the finger from slipping. The user may also directly push the outer side surface of the bottom cover toward a direction away from the housing. The existing of the operating portion makes it easy for the user to open and remove the bottom cover. Furthermore, the operating portion is provided to control the opening force to no more than 2 kilogram force (kgf), so that the container can be easily opened and is resistant to negative pressure, and can be quickly disassembled by the user with less effort. The matching between the positioning piece and the matching portion provides the user with the function of foolproof alignment when operating to open and close the container.

Fourteenth, bottom cover is equipped with a tearing element which can help to tear off the edge of the release layer of the self-adhesive pad, so as to achieve the effect of tearing off the release layer at the same time as the bottom cover is opened, and so that the user does not need to tear off the release layer with bare hands, thus reducing the risk of inaccurate sensing data due to contamination of the sensor, and also avoids the problem of contaminated adhesive pad causing decreased adhesive force.

Through the foregoing embodiments, the storage device and method capable of maintaining a dry state provided by the present invention should be a major innovation in technology field. Obviously, the apparatus and method of the present invention can achieve many effects that are hard to expect by prior arts.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An implantation device for prompt subcutaneous implantation of a sensor to measure a physiological signal of an analyte in a biofluid of a living body having a skin surface, comprising:

a housing having a bottom opening and a lining piece disposed therein, the lining piece having an actuating portion protruding therefrom;

an implantation module including;

a main body, connected to the lining piece, having a slide groove extending along an axial direction, a pair of recessed portions, and a stopping portion adjacent to the pair of recessed portions;

a main cover connected to the main body, defining a displacement space together with the main body, and including a constraint element disposed along the axial direction;

a needle implanting seat movably disposed in the displacement space extendable along the axial direction, and including:

a limiting groove extending parallel to the axial direction, a limiting element disposed on an inner cylindrical member and configured to be restricted by the limiting groove from radial deflection for keeping a needle extracting seat at a constant location relative to the needle implanting seat, and a pair of buckle portions having elasticity and configured for causing bias relative to the axial direction, respectively disposed on an outer cylindrical member and detachably sitting on the stopping portion;

a first elastic element disposed between the needle implanting seat and the lining piece in a first precompressed manner;

the needle extracting seat slidably installed inside the needle implanting seat along the axial direction; and a second elastic element disposed between the needle implanting seat and the needle extracting seat in a second pre-compressed manner; and a detachable module including the sensor detachably engaged with the implantation module, and wherein:

when the implantation module is in a first operating status before the detachable module is attached on the skin surface, the constraint element of the main cover and the limiting groove of the needle implanting seat are kept in a constraint state, when the implantation module is in a second operating status that the detachable module is in a process of being attached on the skin surface, the first elastic element in the first pre-compressed manner is released to a released manner by an external force exerting on the housing through the actuating portion to bias the pair of buckle portions to release the stopping portion so that the constraint element and the limiting groove are not in the constraint state, and when the detachable module has been attached on the skin surface, the needle extracting seat is withdrawn upward so as to release the second elastic element from being in the second pre-compressed manner.

2. The implantation device according to claim 1, further comprising:

a bottom cover detachably coupled to the bottom opening so that the housing and the bottom cover together form an accommodating space.

3. The implantation device according to claim 2, further comprising:

a desiccation indicator disposed at a location visible through a transparent or translucent portion of the housing and configured to provide a visual indication of a dryness within the accommodating space.

4. The implantation device according to claim 2, wherein the detachable module further includes:

an adhesive pad disposed on a base of the detachable module;

a release layer releasably attached to the adhesive pad; and a tearing element connected to the release layer and attached to a chassis portion of the bottom cover, wherein the tearing element is configured to tear away the release layer from the adhesive pad when the bottom cover is separated from the bottom opening by a user.

5. The implantation device according to claim 2, wherein: the bottom cover has a side wall adjacent to the bottom opening, the bottom cover has an operating portion protruding from the side wall to bear a force in a direction away from the housing, wherein the operating portion enables a supporting portion to be formed on an opposite end from the operating portion, a distance between the operating portion and the supporting portion and the force form an operating moment allowing a user to cause a partial side detachment between the bottom cover and the housing, after the bottom cover is separated from the bottom opening by the user, the housing is operated to cause the implantation module to release an action force to cause the detachable module to be detached from the implantation module and to subcutaneously implant a portion of the sensor to measure the physiological signal.

6. The implantation device according to claim 5, wherein the operating portion is a convex portion.

7. The implantation device according to claim 5, wherein the force is in a range of 0.2 kgf and 10 kgf.

8. The implantation device according to claim 5, wherein the distance between the operating portion and the supporting portion is in a range of 15 millimeters to 100 millimeters.

9. The implantation device according to claim 5, wherein: the operating portion is oriented in a first plane;

the bottom cover has a positioning piece that is oriented in a second plane that is substantially perpendicular to the first plane;

the bottom opening has a matching portion oriented in the second plane and configured to abut and align with the positioning piece when the bottom cover and the housing are engaged; and the operating portion is configured to cause a partial side detachment between the bottom cover and the housing, taking advantage of a stress concentration status using the force, and continually applying the force on the operating portion toward a direction away from the housing to enlarge the partial side detachment.

10. The implantation device according to claim 9, wherein the bottom cover defines a reference point, and wherein an angle formed by a first imaginary line extending from the reference point to the positioning piece and a second imaginary line extending from the reference point to the operating portion is in a range of 5 degrees and 180 degrees.

11. The implantation device according to claim 9, wherein:

the partial side detachment is caused by overcoming a resistance force generated due to a combination between the bottom cover and the housing; and during the partial side detachment, the resistance force moves progressively from a first abutment location near the operating portion to a second abutment location farther from the operating portion, wherein the distance in the operating moment increases progressively from a first distance to a second distance greater than the first distance, thereby reducing the force required to maintain the operating moment during the partial side detachment.

12. The implantation device according to claim 2, wherein:

the bottom opening has a first convex ring disposed along an edge of the bottom opening and a first annular groove disposed near the edge of the bottom opening to abut the first convex ring;

the bottom cover has a second convex ring disposed along an edge of the bottom cover and a second annular groove disposed near the edge of the bottom cover to abut the second convex ring;

the first convex ring is fitted into the second annular groove, and the second convex ring is fitted into the first annular groove;

the detachable module further includes a base configured to mount the sensor thereon and having an adhesive pad disposed thereon;

the housing further includes a protective ring sleeved on a bottom portion of the housing and having a lateral opening, wherein the base and the adhesive pad are disposed on an inner side of a bottom edge of the protective ring such that when the bottom edge of the protective ring abuts against the skin surface, wherein the adhesive pad does not contact the skin surface and is visible through the lateral opening before implantation of the sensor;

the implantation module and the detachable module are accommodated in the accommodating space.

13. A physiological signal monitoring system for fast assembly and measuring a physiological signal of an analyte in a living body having a skin surface, comprising:

an implantation device including:

a housing having a bottom opening and a lining piece disposed therein, the lining piece having an actuating portion protruding therefrom;

an implantation module including:

a main body, connected to the lining piece, having a slide groove extending along an axial direction, a pair of recessed portions, and a stopping portion adjacent to the pair of recessed portions;

a main cover connected to the main body, defining a displacement space together with the main body, and including a constraint element disposed along the axial direction;

a needle implanting seat movably disposed in the displacement space extendable along the axial direction, and including:

a limiting groove extending parallel to the axial direction, a limiting element disposed on an inner cylindrical member and configured to be restricted by the limiting groove from radial deflection for keeping a needle extracting seat at a constant location relative to the needle implanting seat, and a pair of buckle portions having elasticity and configured for causing bias relative to the axial direction, respectively disposed on an outer cylindrical member and detachably sitting on the stopping portion;

a first elastic element disposed between the needle implanting seat and the lining piece in a first pre-compressed manner;

the needle extracting seat slidably installed inside the needle implanting seat along the axial direction; and a second elastic element disposed between the needle implanting seat and the needle extracting seat in a second pre-compressed manner; and a detachable module including:

a sensor configured to be detachably partially implanted into the living body; and a base disposing the sensor thereon after the sensor is partially implanted into the living body; and a bottom cover detachably coupled to the bottom opening so that the housing and the bottom cover together form an accommodating space; and a transmitter coupled with the base after the sensor is partially implanted into the living body for transmitting the physiological signal that is measured by the sensor, wherein:

when the implantation module is in a first operating status before the detachable module is attached on the skin surface, the constraint element of the main cover and the limiting groove of the needle implanting seat are kept in a constraint state, when the implantation module is in a second operating status that the detachable module is in a process of being attached on the skin surface, the first elastic element in the first pre-compressed manner is released to a released manner by an external force exerting on the housing through the actuating portion to bias the pair of buckle portions to release the stopping portion so that the constraint element and the limiting groove are not in the constraint state, and when the detachable module has been attached on the skin surface, the needle extracting seat is withdrawn upward so as to release the second elastic element from being in the second pre-compressed manner.

14. The physiological signal monitoring system according to claim 13, wherein:

the bottom cover has a side wall and an operating portion protruding therefrom to bear a force in a direction away from the housing, the operating portion enables a supporting portion to be formed on an opposite end from the operating portion, and the operating portion is a convex portion having a length of no less than 1 millimeter.

15. The physiological signal monitoring system according to claim 13, wherein the bottom opening and the bottom cover have a first joint portion and a second joint portion respectively, the first joint portion is a convex ring disposed along an edge of the bottom opening, the second joint portion is an annular groove disposed along an edge of the bottom cover, and the convex ring is fitted into the annular groove.

16. An implantation device for prompt subcutaneous implantation of a sensor for measuring a physiological signal of a living body having a skin surface, comprising:

a housing having a bottom opening and a lining piece disposed therein, the lining piece having an actuating portion protruding therefrom;

an implantation module, disposed in the housing, including:

a main body, connected to the lining piece, having a slide groove extending along an axial direction, a pair of recessed portions, and a stopping portion adjacent to the pair of recessed portions;

a main cover connected to the main body, defining a displacement space together with the main body, and including a constraint element disposed along the axial direction;

a needle implanting seat movably disposed in the displacement space extendable along the axial direction, and including:

a limiting groove extending parallel to the axial direction, a limiting element disposed on an inner cylindrical member and configured to be restricted by the limiting groove from radial deflection for keeping a needle extracting seat at a constant location relative to the needle implanting seat, and a pair of buckle portions having elasticity and configured for causing bias relative to the axial direction, respectively disposed on an outer cylindrical member and detachably sitting on the stopping portion;

a first elastic element disposed between the needle implanting seat and the lining piece in a first pre-compressed manner;

the needle extracting seat slidably installed inside the needle implanting seat along the axial direction; and a second elastic element disposed between the needle implanting seat and the needle extracting seat in a second pre-compressed manner; and a sensor module detachably disposed in the implantation module to be attached on the skin surface and including a sensor and a base configured to mount the sensor thereon, wherein the base has an adhesive pad disposed thereon, wherein:

when the implantation module is in a first operating status before the sensor module is attached on the skin surface, the constraint element of the main cover and the limiting groove of the needle implanting seat are kept in a constraint state, when the implantation module is in a second operating status that the sensor module is in a process of being attached on the skin surface, the first elastic element in the first pre-compressed manner is released to a released manner by an external force exerting on the housing through the actuating portion to bias the pair of buckle portions to release the stopping portion so that the constraint element and the limiting groove are not in the constraint state, and when the sensor module has been attached on the skin surface, the needle extracting seat is withdrawn upward so as to release the second elastic element from being in the second pre-compressed manner.

17. The implantation device according to claim 16, wherein:

the implantation module further includes a bottom cover detachably coupled with the bottom opening so that the housing and the bottom cover together form an accommodating space, the bottom cover has a side wall adjacent to the bottom opening, the bottom cover has an operating portion protruding from the side wall to bear a force in a direction away from the housing, and enable a supporting portion to be formed on an opposite end from the operating portion, a distance between the operating portion and the supporting portion and the force form an operating moment, the operating portion is configured to initiate a partial side detachment between the bottom cover and the housing, taking advantage of a stress concentration status using the force, to cause the partial side detachment between the bottom cover and the housing, the operating portion is configured to continually bear the force in a direction away from the housing to enlarge the partial side detachment, which causes the bottom cover to be separated from the bottom opening, the housing is put under an operating condition to cause the sensor module to be attached on the skin surface for measuring the physiological signal, the bottom opening and the bottom cover have a first joint portion and a second joint portion, the housing further includes a protective ring sleeved on a bottom portion of the housing and having a lateral opening recessed into a lateral surface of the protective ring, and the implantation module and the sensor module are accommodated in the accommodating space.

18. The implantation device according to claim 17, wherein the accommodating space is an air-tight space.

19. The implantation device according to claim 17, wherein:

the bottom cover further includes:

an inner side surface and a pair of blocking portions protruding from the inner side surface;

the main body further includes:

a pair of fixing members, wherein a fixing member is slidably installed in the slide groove and has a pushing portion corresponding to a respective one of the pair of blocking portions;

the supporting portion opposite to the pushing portion;

a first hook disposed between the pushing portion and the supporting portion; and a guiding portion disposed between the pushing portion and the supporting portion, and having a guide slanting surface;

the needle implanting seat further includes:

a flat plate portion;

the inner cylindrical member connected to the flat plate portion and configured for intersecting therewith; and the outer cylindrical member connected to the flat plate portion, configured for intersecting therewith, and surrounding the inner cylindrical member;

the main cover is disposed between the lining piece and the needle implanting seat, and the first elastic element is disposed between the needle implanting seat and the main cover in the first pre-compressed manner.

20. The implantation device according to claim 17, wherein the base and the adhesive pad of the sensor module are disposed on an inner side of a bottom edge of the protective ring.

* * * * *